(12) United States Patent
Koh et al.

(10) Patent No.: US 12,365,947 B2
(45) Date of Patent: Jul. 22, 2025

(54) METHODS FOR PROFILING AND QUANTITATING CELL-FREE RNA

(71) Applicant: The Board of Trustees of the Leland Stanford Junior University, Stanford, CA (US)

(72) Inventors: Lian Chye Winston Koh, Stanford, CA (US); Stephen R. Quake, Stanford, CA (US); Hei-Mun Christina Fan, Fremont, CA (US); Wenying Pan, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/669,081

(22) Filed: Feb. 10, 2022

(65) Prior Publication Data

US 2022/0213549 A1 Jul. 7, 2022

Related U.S. Application Data

(60) Continuation of application No. 17/497,358, filed on Oct. 8, 2021, which is a continuation of application No. 17/187,298, filed on Feb. 26, 2021, which is a continuation of application No. 16/373,996, filed on Apr. 3, 2019, now abandoned, which is a continuation of application No. 15/377,894, filed on Dec. 13, 2016, now Pat. No. 10,287,632, which is a continuation of application No. 14/861,650, filed on Sep. 22, 2015, now Pat. No. 10,240,200, which is a division of application No. 13/752,131, filed on Jan. 28, 2013, now abandoned.

(60) Provisional application No. 61/591,642, filed on Jan. 27, 2012.

(51) Int. Cl.
| | |
|---|---|
| C12Q 1/68 | (2018.01) |
| C12P 19/34 | (2006.01) |
| C12Q 1/6809 | (2018.01) |
| C12Q 1/6874 | (2018.01) |
| C12Q 1/6876 | (2018.01) |
| C12Q 1/6883 | (2018.01) |
| G16B 25/10 | (2019.01) |
| G16B 40/00 | (2019.01) |
| G16B 40/20 | (2019.01) |
| G16B 50/00 | (2019.01) |
| G16H 10/40 | (2018.01) |
| G16H 50/30 | (2018.01) |
| G06F 18/2135 | (2023.01) |

(52) U.S. Cl.
CPC ......... *C12Q 1/6883* (2013.01); *C12Q 1/6809* (2013.01); *C12Q 1/6874* (2013.01); *C12Q 1/6876* (2013.01); *G16B 25/10* (2019.02); *G16B 40/00* (2019.02); *G16B 40/20* (2019.02); *G16B 50/00* (2019.02); *G16H 10/40* (2018.01); *G16H 50/30* (2018.01); *C12Q 2600/112* (2013.01); *C12Q 2600/158* (2013.01); *G06F 18/2135* (2023.01)

(58) Field of Classification Search
CPC ........ C12Q 2535/122; C12Q 2600/112; C12Q 2600/158

See application file for complete search history.

(56) References Cited

U.S. PATENT DOCUMENTS

| | | |
|---|---|---|
| 5,432,054 A | 7/1995 | Saunders et al. |
| 5,629,147 A | 5/1997 | Asgari et al. |
| 6,664,056 B2 | 12/2003 | Lo et al. |
| 7,235,359 B2 | 6/2007 | Lo et al. |
| 7,713,693 B1 | 5/2010 | Shah |
| 7,829,285 B2 | 11/2010 | Lo et al. |
| 10,155,986 B2 | 12/2018 | Koh et al. |
| 10,240,200 B2 | 3/2019 | Koh et al. |
| 10,240,204 B2 | 3/2019 | Koh et al. |
| 10,287,632 B2 | 5/2019 | Koh et al. |
| 2002/0045176 A1 | 4/2002 | Lo et al. |
| 2003/0108871 A1 | 6/2003 | Kaser |
| 2004/0067507 A1 | 4/2004 | Nolan et al. |
| 2004/0086511 A1 | 5/2004 | Zack et al. |
| 2004/0180048 A1 | 9/2004 | Zack et al. |

(Continued)

FOREIGN PATENT DOCUMENTS

| | | |
|---|---|---|
| AU | 2013211850 | 9/2014 |
| CA | 2838562 | 2/2013 |

(Continued)

OTHER PUBLICATIONS

Winston Koh, et al. "730—Profiling maternal plasma cell-free RNA by RNA-sequencing: a comprehensive approach" American Journal of Obstetrics and Gynecology, vol. 206, Iss 1, Supplement, S324, Jan. 1, 2012. (Year: 2012).*

(Continued)

*Primary Examiner* — Stephen T Kapushoc
(74) *Attorney, Agent, or Firm* — Pamela J. Sherwood; Bozicevic, Field & Francis LLP

(57) ABSTRACT

The invention generally relates to methods for assessing the health of a tissue by characterizing circulating nucleic acids in a biological sample. According to certain embodiments, methods for assessing the health of a tissue include the steps of detecting a sample level of RNA in a biological sample, comparing the sample level of RNA to a reference level of RNA specific to the tissue, determining whether a difference exists between the sample level and the reference level, and characterizing the tissue as abnormal if a difference is detected.

9 Claims, 179 Drawing Sheets

(56) References Cited

U.S. PATENT DOCUMENTS

| | | |
|---|---|---|
| 2006/0003342 A1 | 1/2006 | Bianchi et al. |
| 2006/0166242 A1 | 7/2006 | Pannell et al. |
| 2008/0009467 A1 | 1/2008 | Henderson |
| 2009/0318304 A1 | 12/2009 | Drmanac et al. |
| 2010/0047779 A1 | 2/2010 | Butt et al. |
| 2010/0120787 A1 | 5/2010 | Sutcliffe et al. |
| 2010/0145131 A1 | 6/2010 | Grinberg-Rashi et al. |
| 2011/0003294 A1 | 1/2011 | Liew |
| 2011/0008805 A1 | 1/2011 | Urdea et al. |
| 2011/0144076 A1 | 6/2011 | Williams et al. |
| 2011/0150775 A1 | 6/2011 | Slonim et al. |
| 2011/0263441 A1 | 10/2011 | Golub et al. |
| 2013/0252835 A1 | 9/2013 | Koh et al. |
| 2014/0304845 A1 | 10/2014 | Loboda et al. |
| 2015/0065355 A1 | 3/2015 | Meder et al. |
| 2015/0211070 A1 | 7/2015 | Seligson et al. |
| 2016/0017420 A1 | 1/2016 | Koh et al. |
| 2016/0289762 A1 | 10/2016 | Koh et al. |
| 2017/0145507 A1 | 5/2017 | Koh et al. |
| 2017/0145508 A1 | 5/2017 | Koh et al. |
| 2017/0145509 A1 | 5/2017 | Koh et al. |
| 2018/0357379 A1 | 12/2018 | Koh et al. |

FOREIGN PATENT DOCUMENTS

| | | |
|---|---|---|
| CA | 2863035 | 8/2013 |
| CN | 104334742 | 2/2015 |
| EP | 2807277 | 12/2014 |
| JP | 2010/536372 | 12/2010 |
| JP | 2015511122 | 4/2015 |
| WO | WO2004/065629 | 8/2004 |
| WO | WO2006020005 | 2/2006 |
| WO | WO2009/009457 | 1/2009 |
| WO | WO2009/025852 | 2/2009 |
| WO | WO2009143576 | 5/2009 |
| WO | WO2009/093254 | 7/2009 |
| WO | WO2011/029899 | 3/2011 |
| WO | WO2011/071893 | 6/2011 |
| WO | WO2011/156734 | 12/2011 |
| WO | WO2011156763 A1 | 12/2011 |
| WO | WO2012/004371 | 1/2012 |
| WO | WO2012/012693 | 1/2012 |
| WO | WO2013007708 | 1/2013 |
| WO | WO2013/022953 | 2/2013 |
| WO | WO2013049674 | 4/2013 |
| WO | WO2013/113012 | 8/2013 |
| WO | WO2014150198 | 9/2014 |
| WO | WO2016196945 | 12/2016 |
| WO | WO2017/046181 | 3/2017 |
| WO | WO2017156310 | 9/2017 |

OTHER PUBLICATIONS

Andrew Whitehead et al., "Variation in tissue-specific gene expression among natural populations" Genome Biology 2005, 6:R13 (Year: 2005).*

Vivian G. Cheung, et al., "Natural variation in human gene expression assessed in lymphoblastoid cells" Nature Genetics, vol. 33, Mar. 2003, pp. 422-424. (Year: 2003).*

Tissue gene expression data, HPA RNA-Seq normal tissues, CAMK1G calcium/calmodulin dependent protein kinase IG [ Homo sapiens (human) ], printed from https://www.ncbi.nlm.nih.gov/gene/57172/?report=expression (Year: 2022).*

Kasper Lage, et al. "A large-scale analysis of tissue-specific pathology and gene expression of human disease genes and complexes" PNAS, Dec. 30, 2008, vol. 105, No. 52, pp. 20870-20875 . . . (Year: 2008).*

Parul Gahlan, et al. "De novo sequencing and characterization of Picrorhiza kurrooa transcriptome at two temperatures showed major transcriptome adjustments" BMC Genomics 2012, 13:126 (Year: 2012).*

Kausik Das, et al. "A cell stabilizing reagent in Cell-Free DNA™ BCT is formaldehyde free and has No. adverse effects on DNA integrity", Conference Paper, Jul. 2012, Presented at the AACC annual meeting, 2012, Los Angeles, CA. (Year: 2012).*

M. R. Fernando, et al. "A new methodology to preserve the original proportion and integrity of cell-free fetal DNA in maternal plasma during sample processing and storage" Prenat Diagn 2010; 30: 418-424 (Year: 2010).*

Jeremy D Henson, et al. "DNA C-circles are specific and quantifiable markers of alternative-lengthening-of-telomeres activity" Nature Biotechnology, vol. 27, No. 13, Dec. 2009. (Year: 2009).*

Dmitry V. Semenov, et al.( 2012) "Unbiased approach to profile the variety of small non-coding RNA of human blood plasma with massively parallel sequencing technology", Expert Opinion on Biological Therapy, 12:sup1, S43-S51 (Year: 2012).*

Examination Report for Australian Application No. 2013211850 dated Apr. 14, 2016, 4 pages.

Pawekczky et al., "Spontaneous preterm labor is associated with an increase in the proinflammatory signal transducer TLR4 receptor on maternal blood monocytes", BMC Preg Childbirth, Oct. 21, 2010, pp. 1-9, (10) 66, Springer Nature, Basingstoke, United Kingdom.

Miura et al., "Identification of pregnancy-associated microRNAs in maternal plasma", Clin Chern., Oct. 2010, pp. 1767-1771, 56(11), American Association for Clinical Chemistry, Washington, D.C.

Segal et al., "Module networks: identifying regulatory modules and their condition-specific regulators from gene 9Xpression data", Nature Genetics, Jun. 2003, pp. 166-176, 34(2), Springer Nature, Basingstoke, United Kingdom.

Human Protein Atlas, primary reference Uhlen et al. Proteomics. Tissue-based map of the human proteome. Science, 347:6220 (Jan. 23, 2015), retrieved from the internet on Dec. 6, 2016 (http://www.proteinatlas.org/ humanproteome/tissue+specific.

Human Protein Atlas, (primary reference Uhlen et al. Proteomics. Tissue-based map of the human proteome. Science, 347:6220 (Jan. 23, 2015), retrieved from the internet on Dec. 6, 2016 (http://WININ.proteinatlas.org/search/protein_class:COSMIC%20Somatic%20Mutations).

Goldfarb et al., "A numerically stable dual method for solving strictly convex quadratic programs", Mathematical Programming, Sep. 1983, pp. 1-33, vol. 27, Issue 1, Springer Nature, Basingstoke, United Kingdom.

Hafner et al., "Differential gene expression of Eph receptors and ephrins in benign human tissues and cancers", clinical Chemistry, Feb. 2004, pp. 490-499, 50(3), American Association for Clinical Chemistry, Washington, D.C.

Herzenberg et al., "Fetal cells in the blood of pregnant women: detection and enrichment by fluorescence-Activated cell sorting", Proc. Natl. Acad_ Sci., Mar. 1, 1979 , pp. 1453-1455, 76(3), National Academy of Sciences, Washington, D.C.

Ng et al., The concentration of circulating corticotropin-releasing hormone mRNA in maternal plasma is increased in preeclampsia, Clinical Chemistry, May 2003, pp. 727-731, vol. 49, Issue 5, American Association for Clinical chemistry, Washington, D.C.

Pavlidsis et al., "Analysis of strain and regional variation in gene expression in mouse brain", Genome Biology, Sep. 27, 2001, pp. 1-15, 2 (10), Springer Nature, Basingstoke, United Kingdom.

Spurgeon et al., "High throughout gene expression measurement with real time PCR in a microfluidic dynamic array", PLoS One, Feb. 27, 2008, pp. 1-7, 3(2), PLOS, San Francisco, CA.

ADORA3 information from GeneCards Human Gene Database, printed in Jul. 8, 2017 from www.genecards.org, pp. 1-17.

Bianchi et al., "Isolation of fetal DNA from nucleated erythrocytes in maternal blood", Proc Natl Acad Sci USA, May 1, 990, pp. 3279-3283, 87(9), National Academy of Sciences, Washington, D.C.

Breuleux, "Role of Heregulin in Human Cancer", Cellular and Molecular Life Sciences, Sep. 2007, pp. 2358-2377, vol. 64, Issue 18, Springer Nature, Basingstoke, United Kingdom.

Butt et al., "Overview of circulating nucleic acids in plasma/serum", Annals of the New York Academy of Sciences, Dec. 1, Jul. 2009, pp. 236-242, vol. 1137, Wiley, Hoboken NJ.

Cahoy et al., "A transcriptome database for astrocytes, neurons, and oligodendrocytes: a new resource for understanding brain development and function", Journal of Neuroscience, Jan. 2, 2008, pp. 264-278, 28(1), Society for Neuroscience, Washington, D.C.

(56) References Cited

OTHER PUBLICATIONS

Chan et al., "Aberrant Concentrations of Liver-Derived Plasma Albumin mRNA in Liver Pathologies", Clinical Chemistry, Jan. 2010, pp. 82-S9, vol. 56, Issue 1, American Association for Clinical Chemistry, Washington, DC.
Chaussabel et al., "A modular analysis framework for blood genomics studies: application to systemic lupus erythematosus", Immunity, Jul. 18, 2008, pp. 150-164, 29(1), Elsevier, New York City, NY.
Cheung et al., "Natural variation in human gene expression assessed in lymphoblastoid cells", Nature Genetics, 2003, pp. 422-425, 33, Springer Nature, Basingstoke, United Kingdom.
Chott et al., "Brain Biopsy in Dementia: Clinical Indications and Diagnostic Approach", Acta Neuropathol, 2010, pp. 327-341, vol. 120, Springer Nature, Basingstoke, United Kingdom.
EP13740984.3 The Extended European Search Report dated Jan. 14, 2016.
EP19173751.9 The Extended European Search Report dated Oct. 16, 2019.
Extended European Search Report for PCT/US2013/023471 dated Jan. 16, 2014, 18 pages.
Furneaux et al., "Characterization of a cDNA encoding a 34-kDa Purkinje neuron protein recognized by sera from patients with paraneoplastic cerebellar degeneration", Proc. Natl. Acad. Sci. USA, Apr. 1989, pp. 2873-2877, vol. 86, National Academy of Sciences, Washington, D.C.
Geekiyanage et al., "Blood Serum miRNA: Non-invasive Biomarkers for Alzheimer's Disease", Experimental Neurology, Jun. 2012, pp. 491-496, vol. 235, Issue 2, Elsevier, New York City, NY.
GenBank Accession NM_004352 "*Homo sapiens* Cerebellin 1 Precursor (CBLN1), mRNA", Printed from https://www.ncbi.nlm.nih.gov, Apr. 20, 2010, pp. 1-5, Rockefeller University Press, New York City, NY.
GeneCard for ABHD17B gene, printed Jun. 16, 2017 from wvvvv.genecards.org, pp. 1-14.
GeneCards ZNF717 Gene (protein coding), pritned in Jul. 5, 2017, pp. 1-16, from http://www.genecards.org.
Goldenburg et al., "Biochemical markers for the prediction of preterm birth", Am JOb Gyn, May 2005, pp. S36-S46, vol. 192, Issue 5, Elsevier, New York City, NY.
Gracien et al., "Paraneoplastic cerebellar degeneration mimicking development of secondary progressive multiple sclerosis in a patient with relapsing-remitting multiple sclerosis", Multiple Sclerosis Journal, Dec. 8, 2010, pp. 498-500, vol. 17, Issue 4, Sage Journals, Thousand Oaks, CA.
Guo et al., "Genome-wide Survey of Tissue-Specific microRNA and Transcription Factor Regulatory Networks in 12 Tissues", Scientific Reports, Jun. 3, 2014, pp. 1-9, vol. 4 (5150), Springer Nature, Basingstoke, United Kingdom.
Han, et al., "Janus-like opposing roles of CD47 in autoimmune brain inflammation in humans and mice" J Exp Med., Jun. 25, 2012, pp. 1-10, 209 (7), Rockefeller University Press, New York City, NY.
Heung Dissertation, "Development and Characterization of Circulating RNA Markers", The Chinese University of Hong Kong, Aug. 2009, pp. 1-239, ProQuest LLC, Ann Arbor, MI.
Ho et al., "Gene Expression Profiling of Liver Cancer Stem Cells by RNA-Sequencing", PLoS ONE, May 14, 2012, pp. 1-16, vol. 7, Issue 5, e37159, PLOS, San Francisco, CA.
Hoshikawa et al., "Hypoxia induces different genes in the lungs of rats compared with mice", Physiol Genomics Feb. 6, 2003, pp. 209-219, vol. 12 No. 3, The American Physiological Society, Rockville, MD.
International Application No. PCT/US2017/021637 International Preliminary Report on Patentability Mailed Sep. 11, 2018.
International Application No. PCT/US2017/021637 International Search Report and Written Opinion Mailed Jun. 6, 2017.
International Search Report and Written Opinion mailed on Mar. 5, 2015, for International Patent Application No. PCT/US14/64355, filed Nov. 6, 2014 (10 pages).
International Search Report and Written Opinion for PCT/US13/23471, dated Apr. 11, 2013, 7 pages.
Koh et al., "Noninvasive in vivo monitoring of tissue-specific global gene expression in humans", PNAS, May 20, 2014, pp. 7361-7366, vol. 111, No. 20, National Academy of Sciences, Washington, D.C.
Li et al., "Blood transcriptomics and metabolomics for personalized medicine", Computational and Structural Biotechnology Journal, 2016, pp. 1-7, 14, Elsevier, New York City, NY.
Li et al., "Circulatory miR-34a as an RNA-based, noninvasive biomarker for brain aging", Aging, Oct. 2011, pp. 985-1002, vol. 3, No. 10, Impact Journals, LLC, Orchard Park, NY.
Li et al., "Molecular signatures of antibody responses derived from a systems biology study of five human vaccines", Nature Immunology, Feb. 2014, pp. 195-204, 15(2), Springer Nature, Basingstoke, United Kingdom.
Li et al., "Serum Circulating Human mRNA Profiling and Its Utility for Oral Cancer Detection", Journal of Clinical Oncology, Apr. 10, 2006, pp. 1754-1760, vol. 24, No. 11, American Society of Clinical Oncology, Alexandria, VA.
Lo et al., "Plasma placental RNA allelic ratio permits noninvasive prenatal chromosomal aneuploidy detection", Nature Medicine, Jan. 7, 2007, pp. 218-223, 13(2), Springer Nature, Basingstoke, United Kingdom.
Lo, Noninvasive prenatal detection of fetal chromosomal aneuploidies by maternal plasma nucleic acid analysis: a review of the current state of the art: , BJOG, Dec. 12, 2008, pp. 152-157, 16(2), American Association for clinical Chemistry, Washington, D.C.
Makhseed et al., "Pro-inflammatory maternal cytokine profile in preterm delivery", Amm J Rep Immunol, Apr. 9, 2003, pp. 308-318, 49, Wiley, Hoboken, NJ.
Maron et al., "Gene expression analysis in pregnant women and their infants identifies unique fetal biomarkers that circulate in maternal blood", J Clin Investigation, Oct. 1, 2007, pp. 3007-3019, 117(10), American Society for clinical Investigation, Ann Arbor, MI.
Mitchell et al., "Circulating microRNAs as stable blood-based markers for cancer detection", Proceedings of the National Academy of Sciences, Jul. 29, 2008, pp. 10513-10518, 105 (30), National Academy of Sciences, Washington, D.C.
Miyamoto et al., "Detection of Cell-Free, Liver-Specific mRNAs in Peripheral Blood from Rats with Hepatotoxicity: A Potential Toxicological Biomarker for Safety Evaluation", Toxicological Sciences, Sep. 8, 2003, pp. 538-545,06(2), Oxford University Press, Oxford, United Kingdom.
Morozova et al, "Applications of new sequencing technologies for transcriptome analysis", Ann Rev Gen Hum Gen, Sep. 2009, pp. 135-151, 10 (1), Annual Reviews, Palo Alto, CA.
Morozova et. al: "Applications of New Sequencing Technologies for Transcriptome Analysis" Annual Review .pp. 136-151.
Partial supplementary European Search Report mailed Oct. 12, 2015, for European patent application 13740984.3, which is a regional stage entry of International Patent Application No. PCT/US2013/023471 with International Filing Date Jan. 28, 2013 (9 pages).
Poon et al., "Presence of fetal RNA in maternal plasma", Clinical Chemistry, Nov. 2000, pp. 1832-1834, 46 11), American Association for Clinical Chemistry, Washington, D.C.
Porter et al., A SAGE (serial analysis of gene expression) view of breast tumor progression:, Cancer Res., Aug. 2001, pp. 5697-5702, 61(15), American Association for Cancer Research, Philadelphia, PA.
Rao et al., "MicroRNAs as biomarkers for CNS disease", Frontiers in Molecular Neuroscience, Nov. 26, 2013, pp. 1-13, vol. 6, Article 39, Frontiers Media S.A, Lausanne, Switzerland.
Ravetti et al in "Uncovering Molecular Biomarkers That Correlate Cognitive Decline with the Changes of Hippocampus' Gene Expression Profiles in Alzheimer's Disease", PLOS ONE, Apr. 13, 2010 pp. 1-42, vol. 5, No. 4, PLOS ONE, San Francisco, CA.
Redell et al., "Human Traumatic Brain Injury Alters Plasma microRNA Levels", Journal of Neurotrauma, Dec. 7, 2010, pp. 2147-2156, vol. 27Issue 12, Mary Ann Liebert, Inc., Larchmont, NY.
Rockett, et al. Surrogate tissue analysis: monitoring toxicant exposure and health status of inaccessible tissues through the analysis of accessible tissues and cells. Toxicol Appl Pharmacol. Jan. 15, 2004;194(2):189-99.

(56) References Cited

OTHER PUBLICATIONS

Scherzer, "Chipping away at diagnostics for neurodegenerative diseases", Neurobiology of Disease, Aug. 2009, pp. 148-156, vol. 35, Issue 2, Elsevier, New York City, NY.
Sergueeva et al., "Novel Tissue Types for the Development of Genomic Biomarkers", Chapter of the book Biomarker, Apr. 27, 2012, pp. 271-294, In Tech, Croatia, European Union.
Shigaki et al., "Differentially expressed genes in sporadic amyotrophic lateral sclerosis spinal cords-screening by molecular indexing and subsequent eDNA microarray analysis", FEBS Letters, Nov. 6, 2002, pp. 354-358, vol. 531, Issue 2, Wiley, Hoboken, NJ.
Siegel et al., "Circulating microRNAs involved in multiple sclerosis", Mol Bioi Rep., Jan. 2012, pp. 6219-6225, vol. 39, No. 5, Springer, New York City, NY.
Staal et al., "DNA microarrays for comparison of gene expression profiles between diagnosis and relapse in precursor-B acute lymphoblastic leukemia: choice of technique and purification influence the identification of potential diagnostic markers", Leukemia, Jun. 19, 2003, pp. 1324-1332, 17, Springer Nature, Basingstoke, United Kingdom.
Su et al., "A gene atlas of the mouse and human protein-encoding transcriptomes", Proc Natl Acad Sci USA, Apr. 20, 2004, p. 6062-6067, 101(16), National Academy of Sciences, Washington, D.C.
Swarup, et al."Circulating (cell-free) nucleic acids—a promising, non-invasive tool for early detection of several human diseases" FEBS Lett. Mar. 6, 2007;581(5):795-9.
U.S. Appl. No. 13/752,131 Office Action dated Apr. 9, 2015.
U.S. Appl. No. 13/752,131 Office Action dated Feb. 12, 2014.
U.S. Appl. No. 13/752,131 Office Action dated Jun. 17, 2014.
U.S. Appl. No. 13/752,131 Office Action dated Mar. 7, 2016.
U.S. Appl. No. 13/752,131 Office Action dated Nov. 3, 2015.
U.S. Appl. No. 14/861,650 Notice of Allowance dated Nov. 2, 2018.
U.S. Appl. No. 14/861,650 Office Action dated Apr. 18, 2016.
U.S. Appl. No. 14/861,650 Office Action dated Dec. 8, 2017.
U.S. Appl. No. 14/861,650 Office Action dated Jun. 22, 2017.
U.S. Appl. No. 14/861,650 Office Action dated Oct. 25, 2016.
U.S. Appl. No. 15/377,894 Notice of Allowance dated Dec. 26, 2018.
U.S. Appl. No. 15/377,894 Office Action dated Dec. 22, 2017.
U.S. Appl. No. 15/377,901 Notice of Allowance dated Aug. 6, 2018.
U.S. Appl. No. 15/377,901 Office Action dated Oct. 20, 2017.
U.S. Appl. No. 15/377,904 Notice of Allowance dated Nov. 7, 2018.
U.S. Appl. No. 15/377,904 Office Action dated Dec. 20, 2017.
U.S. Appl. No. 15/377,904 Office Action dated Jul. 19, 2017.
U.S. Appl. No. 15/969,603 Office Action dated Dec. 14, 2018.
Viale et al., "The melanin-concentrating hormone gene in human: flanking region analysis, fine chromosome mapping, and tissue-specific expression", Molecular Brain Research, Jun. 1997, pp. 243-255, vol. 46, Issues—2, Elsevier, New York City, NY.
Villani et al., "Cytokines, Neurotrophins, and Oxidative Stress in Brain Disease From Mucopolysaccharidosis IIIB", Journal of Neuroscience Research, Feb. 15, 2007, pp. 612-622, vol. 85, Issue 3, Wiley, Hoboken, NJ.
Wetmore, et al. "Quantitative analyses and transcriptomic profiling of circulating messenger RNAs as biomarkers of rat liver injury." Hepatology. Jun. 2010;51(6):2127-39.
Wilhelm et al., "RNA-Seq—quantitative measurement of expression through massively parallel RNA-sequencing" Methods, 2009 , pp. 249-257, vol. 48, Issue 3, Elsevier, New York City, NY.
Wu et al., "BioGPS: an extensible and customizable portal for querying and organizing gene annotation Resources", Genome Biology, Nov. 2009, pp. 1-8, 10(11), Springer Nature, Basingstoke, United Kingdom.
Xiao et al., "TiSGeD: a database for tissue-specific genes", Bioinformatics, May 1, 2010, pp. 1273-1275, vol. 26, Issue 9, Oxford University Press, Oxford, United Kingdom.
Bullard et al. (2010) "Evaluation of statistical methods for normalization and differential expression in mRNA-Seq experiments." *BMC bioinformatics*, 11, pp. 1-13.
Kallio et al. (2011) "Chipster: user-friendly analysis software for microarray and other high-throughput data." *BMC genomics*, 12, pp. 1-14.
Hiller et al. (2009)"Identifiability of Isoform Deconvolution from Junction Arrays and RNA-Seq." Bioinformatics 25.23, pp. 3056-3059.
Fehlbaum-Beurdeley, (2010) Pascale, et al. "Toward an Alzheimer's disease diagnosis via high-resolution blood gene expression." *Alzheimer's & Dementia* 6(1): 25-38.
Hanyu, et al. (2022) "Characterization of Alzheimer's Disease Subtypes Based on Magnetic Resonance Imaging and Perfusion Single-Photon Emission Computed Tomography." *Journal of Alzheimer's Disease* 87(2): 781-789.
Hornaday et al. (2022) "Is there a maternal blood biomarker that can predict spontaneous preterm birth prior to labour onset? A systematic review." *PloS one*, 17(4), e0265853.
Purwosunu et al. (2009). "Prediction of preeclampsia by analysis of cell-free messenger RNA in maternal plasma." *American journal of obstetrics and gynecology*, 200(4), 386-e1-386.e7.
Chan. (2014) "Biochemical markers of spontaneous preterm birth in asymptomatic women." *BioMed research international*, 14, pp. 1-8.
Booij et al (2011) "A Gene Expression Pattern in Blood for the Early Detection of Alzheimer's Disease" Journal of Alzheimer's Disease 23, pp. 109-119.
Gong et al. (2011) "Optimal Deconvolution of Transcriptional Profiling Data Using Quadratic Programming with Application to Complex Clinical Blood Samples." PloS one 6(11), (e27156-e27156. Web.
Illumina (2010) "RNA Sequencing Analysis With TopHat Booklet"https://www.illumina.com/documents/products/technotes/RNASeqAnalysisTopHat.pdf.
Illumina (2011) "White Paper: Sequencing: RNA-Seq Data Comparison with Gene Expression Microarrays" rna-seq-to-arrays-comparison-white-paper-470-2011-001. pdf" i llu mina.com/contenUdam/ill u mina-marketing/docu ments/products/ whitepapers/rna-seq-to-arrays-com parison-white-paper-470-2011-001. pdf".
Koschmieder et al. (2011) "Tools for Managing and Analyzing Microarray Data." Briefings in bioinformatics 13.1: 46-60. Web.
Matsui et al. (2007) "Expression of APP pathway mRNAs and proteins in Alzheimer's disease" Brain Research, pp. 116-123.
McGill (2003 ) "Tutorial: RMA Analysis using the Microarray Platform Website" *McGill Genmoe Centre*, pp. 1-12. "https://genomequebec.mcgill.ca/nanuqAdministration/download/MicroarrayRMATutorial_en.pdf".
Pepke et al. (2009) "Computation for Ch IP-Seq and RNA-Seq Studies." Nature methods 6(11), pp. S22-S32. Web.
Schott et al., "Brain Biopsy in Dementia: Clinical Indications and Diagnostic Approach", Acta Neuropathol, 2010, pp. 327-341, vol. 120, Springer Nature, Basingstoke, United Kingdom.
Tani et al. (2007) "Circulating Cell-Free mRNA in Plasma as a Tumor Marker for Patients with Primary and Recurrent Gastric Cancer." Anticancer research 27, pp. 1207-1212. Print.
U.S. Appl. No. 15/377,894 Office Action dated Jul. 13, 2017.
U.S. Appl. No. 15/969,603 Office Action dated Jul. 6, 2018.
Wang et al (2003) "Gene Structure-Based Splice Variant Deconvolution Using a Microarry Platform." Bioinformatics 19(1), pp. i315-i322.Web.
Wang et al. (2009) "RNA-Seq: a revolutionary tool for transcriptomics" Nature Reviews Genetics. 10, pp. 57-63.

\* cited by examiner

| Female Pregnancy Associated Differential Expressed Transcripts | |
|---|---|
| PAPPA | PAPPA antisense RNA (non-protein coding); pregnancy-associated plasma protein A, pappalysin 1 |
| TEAD3 | TEA domain family member 3 |
| ADM | adrenomedullin |
| CSH1 | chorionic somatomammotropin hormone 1 (placental lactogen) |
| CSH2 | chorionic somatomammotropin hormone 2 |
| INSL4 | insulin-like 4 (placenta) |
| PGF | placental growth factor |
| PSG1 | pregnancy specific beta-1-glycoprotein 1 |
| PSG11 | pregnancy specific beta-1-glycoprotein 11 |
| PSG2 | pregnancy specific beta-1-glycoprotein 2 |
| PSG3 | pregnancy specific beta-1-glycoprotein 3 |
| PSG5 | pregnancy specific beta-1-glycoprotein 5 |
| PSG6 | pregnancy specific beta-1-glycoprotein 6 |
| PSG4,PSG8 | pregnancy specific beta-1-glycoprotein 7;pregnancy specific beta-1-glycoprotein 8; pregnancy specific beta-q-glycoprotein 4 |
| PSG9 | pregnancy specific beta-1-glycoprotein 9 |
| PRLR | prolactin receptor |
| SFR4 | secreted frizzled-related protein 4 |
| SPP1 | secreted phosphoprotein 1 |

FIG. 1

| Ranking by Significance | Gene Name |
|---|---|
| 1 | PVALB |
| 2 | CLCN3 |
| 3 | ITGA2B |
| 4 | LTV1 |
| 5 | HIST1H4B |
| 6 | TREML1 |
| 7 | NPTN |
| 8 | LSM2 |
| 9 | SCGB1C1 |
| 10 | NOP10 |
| 11 | MFSD1 |
| 12 | MALAT1 |
| 13 | GDI1 |
| 14 | HIST1H1C |
| 15 | HIST1H4H |
| 16 | CD226 |
| 17 | ITM2B |
| 18 | MLLT6 |
| 19 | ANO6 |
| 20 | ITGB3 |

FIG. 4

| Term | RT | Genes | Count | % | P-Value | Benjamini |
|---|---|---|---|---|---|---|
| cell surface | RT | | 5 | 26.3 | 7.6E-4 | 5.1E-2 |
| platelet alpha granule | RT | | 3 | 15.8 | 2.2E-3 | 7.2E-2 |
| platelet alpha granule membrane | RT | | 2 | 10.5 | 1.2E-2 | 2.5E-1 |
| vesicle membrane | RT | | 3 | 15.8 | 1.5E-2 | 2.3E-1 |
| secretory granule | RT | | 3 | 15.8 | 2.1E-2 | 2.5E-1 |

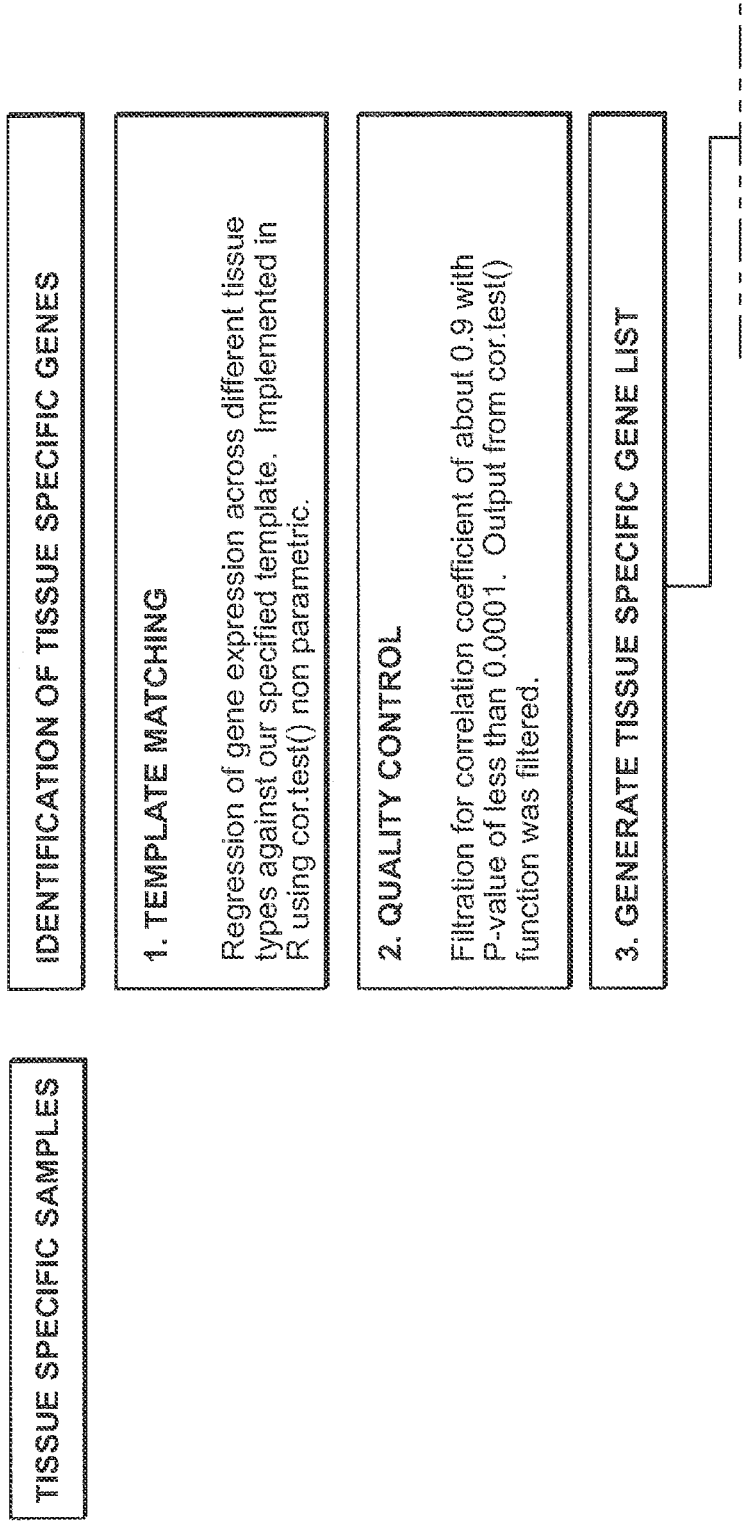

FIG. 8A

List of selected Fetal Tissue Specific Transcripts

| Gene Symbol | Gene Full Name | Tissue |
|---|---|---|
| ACTB | actin, beta | Housekeeping |
| ADAM12 | ADAM metallopeptidase domain 12 | Placenta |
| AFP | alpha-fetoprotein | Fetal liver |
| ALPP | alkaline phosphatase, placental | Placenta |
| APOA4 | apolipoprotein A-IV | Fetal liver |
| BACE2 | beta-site APP-cleaving enzyme 2 | Placenta |
| CALCB | calcitonin-related polypeptide beta | Dorsal root ganglion |
| CGB | chorionic gonadotropin, beta polypeptide | Placenta |
| CRP | C-reactive protein, pentraxin-related | Fetal liver |
| DCX | doublecortin | Fetal brain |
| DLX2 | distal-less homeobox 2 | Fetal brain |
| EPB42 | erythrocyte membrane protein band 4.2 | BM-CD71+Early erythroid |
| EPX | eosinophil peroxidase | Fetal liver |
| EVX1 | even-skipped homeobox 1 | Fetal liver |
| FGA | fibrinogen alpha chain | Fetal liver |
| FOXG1 | forkhead box G1 | Fetal brain |
| GAPDH | glyceraldehyde-3-phosphate dehydrogenase | Housekeeping |
| GH2 | growth hormone 2 | Placenta |

FIG. 8B

| | | |
|---|---|---|
| GNAZ | guanine nucleotide binding protein (G protein), alpha z polypeptide | Fetal brain |
| GPR116 | G protein-coupled receptor 116 | Fetal lung |
| GYPE | glycophorin E (MNS blood group) | BM-CD71+Early erythroid |
| HSD17B1 | hydroxysteroid (17-beta) dehydrogenase 1 | Placenta |
| JUP | junction plakoglobin | Bronchial epithelial cells |
| KRT81 | keratin 81 | Placenta |
| MEF2C | myocyte enhancer factor 2C | Fetal brain |
| MN1 | meningioma (disrupted in balanced translocation) 1 | Fetal brain |
| NPY1R | neuropeptide Y receptor Y1 | Fetal brain |
| NTSR1 | neurotensin receptor 1 (high affinity) | Fetal brain |
| OAZ1 | ornithine decarboxylase antizyme 1 | Housekeeping |
| PSG7 | pregnancy specific beta-1-glycoprotein 7 (gene/pseudogene) | Placenta |
| PTGER3 | prostaglandin E receptor 3 (subtype EP3) | Fetal brain |
| RHCE | Rh blood group, CcEe antigens | BM-CD71+Early erythroid |
| SATB2 | SATB homeobox 2 | Fetal brain |
| SERPINA7 | serpin peptidase inhibitor, clade A (alpha-1 antiproteinase, antitrypsin), member 7 | Cervix |
| SLC4A1 | solute carrier family 4, anion exchanger, member 1 (erythrocyte membrane protein band 3, Diego blood group) | BM-CD71+Early erythroid |
| SLITRK3 | SLIT and NTRK-like family, member 3 | Placenta |
| VGLL1 | vestigial like 1 (Drosophila) | Placenta |
| ZNF238 | zinc finger protein 238 | Fetal brain |

Example of raw qPCR data for fetal brain transcript ZNF238 obtained from subject sample P53 shows the changes across the three trimesters & post-partum.

Example of raw qPCR data for fetal brain transcript ZNF238 obtained from subject sample P53 shows the melting curve of the same experiments of 9A.

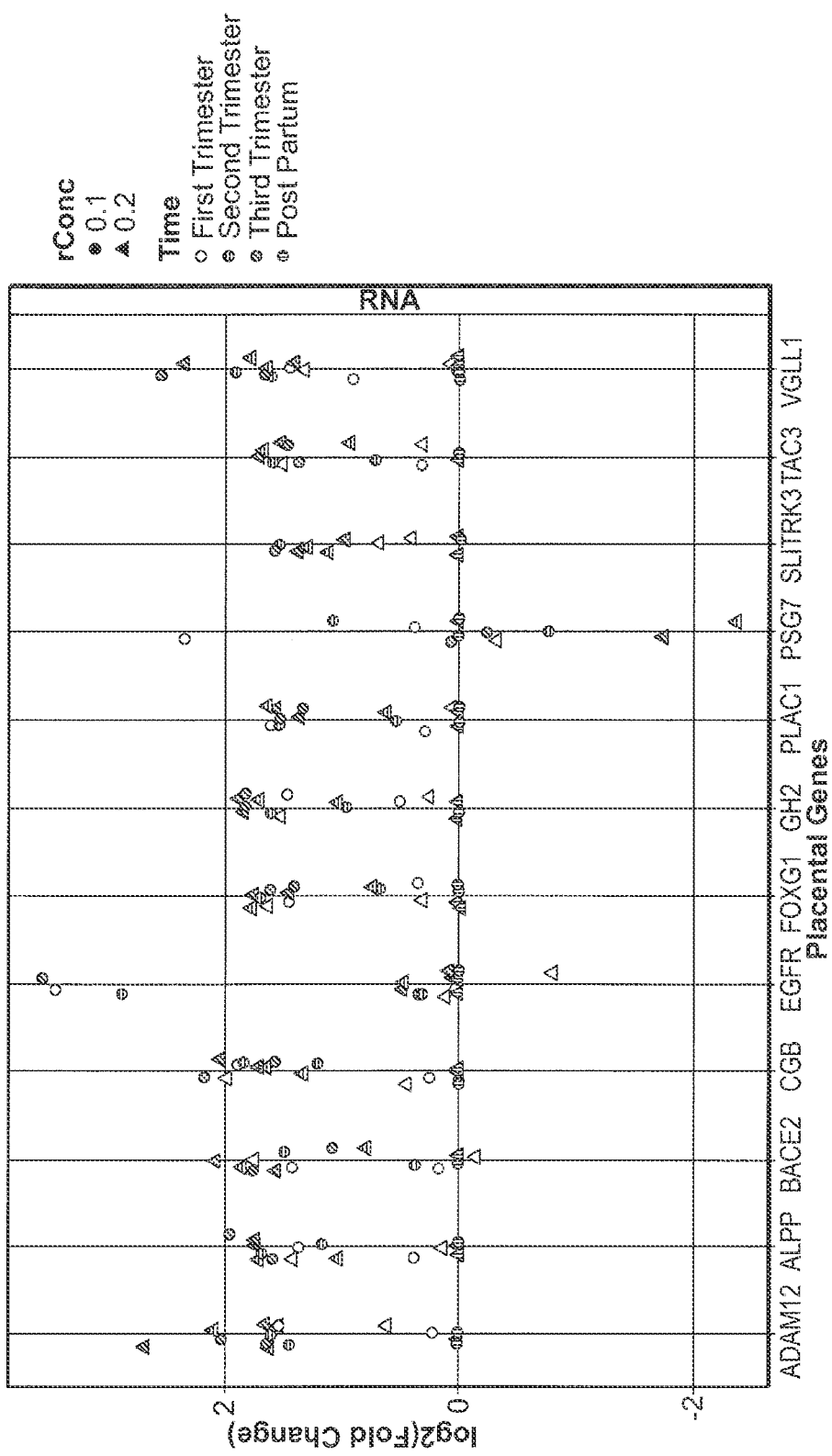

FIG. 13

| Donors | Whole Blood (%) | Bone marrow (%) | Hypothalamus (%) | Smooth Muscle (%) | Lung (%) | Thymus (%) | Lymph node (%) | Thyroid (%) |
|---|---|---|---|---|---|---|---|---|
| d1 | 38.13 | 22.94 | 7.73 | 6.70 | 6.27 | 3.56 | 12.67 | 2.00 |
| d2 | 42.64 | 13.88 | 6.10 | 7.40 | 6.14 | 2.85 | 18.06 | 2.93 |
| d3 | 47.61 | 10.16 | 7.87 | 7.43 | 3.07 | 4.68 | 16.18 | 2.99 |
| d4 | 43.64 | 14.30 | 4.86 | 6.38 | 6.70 | 4.06 | 16.33 | 3.73 |

Relative Composition of different organs contribution towards plasma cell free transcriptome

FIG. 14

| Donors | hypothalamus (%) | spleen (%) |
|---|---|---|
| d1 | 64.85 | 35.15 |
| d2 | 63.13 | 36.87 |
| d3 | 64.56 | 35.44 |
| d4 | 65.29 | 34.71 |

Decomposition of Organ contribution towards cell free transcriptome using RNA-seq data

FIG. 15A

| Gene List of transcripts used for verification with qPCR | |
|---|---|
| Gene | Tissue |
| PMCH | Amygdala |
| HAPLN1 | Bronchial epithelial cells |
| PRDM12 | Cardiac myocytes |
| ARPP-21 | Caudate nucleus |
| GPR88 | Caudate nucleus |
| PDE10A | Caudate nucleus |
| CBLN1 | Cerebellum |
| CDH22 | Cerebellum |
| DGKG | Cerebellum |
| CDR1 | Cerebellum |
| FAT2 | Cerebellum |
| GABRA6 | Cerebellum |
| KCNJ12 | Cerebellum |
| KIAA0802 | Cerebellum |
| NEUROD1 | Cerebellum |
| NRXN3 | Cerebellum |
| PPFIA4 | Cerebellum |
| ZIC1 | Cerebellum |
| SAA4 | Cervix |
| SERPINC1 | Cervix |
| CALML4 | Colon |
| DSC2 | Colon |
| ACTC1 | Heart |
| NKX2-5 | Heart |

FIG. 15B

| | |
|---|---|
| CASQ2 | Heart |
| CKMT2 | Heart |
| HRC | Heart |
| HSPB3 | Heart |
| HSPB7 | Heart |
| ITGB1BP3 | Heart |
| MYL3 | Heart |
| MYL7 | Heart |
| MYOZ2 | Heart |
| NPPB | Heart |
| CSRP3 | Heart |
| MYBPC3 | Heart |
| PGAM2 | Heart |
| TNNI3 | Heart |
| SLC4A3 | Heart |
| TNNT2 | Heart |
| SYNPO2L | Heart |
| AVP | Liver |
| ACTB | Housekeeping |
| GAPDH | Housekeeping |
| MAB21L2 | Housekeeping |
| HCRT | Hypothalamus |
| OXT | Hypothalamus |
| BBOX1 | Kidney |
| AQP2 | Kidney |
| KCNJ1 | Kidney |
| FMO1 | Kidney |
| NAT8 | Kidney |
| XPNPEP2 | Kidney |
| PDZK1IP1 | Kidney |
| PTH1R | Kidney |
| SLC12A1 | Kidney |
| SLC13A3 | Kidney |
| SLC22A6 | Kidney |
| SLC22A8 | Kidney |
| SLC7A9 | Kidney |

FIG. 15C

| | |
|---|---|
| UMOD | Kidney |
| SLC17A3 | Kidney |
| AKR1C4 | Liver |
| C8G | Liver |
| APOF | Liver |
| AQP9 | Liver |
| CYP2A6 | Liver |
| CYP1A2 | Liver |
| CYP2C8 | Liver |
| CYP2D6 | Liver |
| CYP2E1 | Liver |
| ITIH4 | Liver |
| HRG | Liver |
| FTCD | Liver |
| IGFALS | Liver |
| RDH16 | Liver |
| SDS | Liver |
| SLC22A1 | Liver |
| TBX3 | Liver |
| SLC27A5 | Liver |
| KCNK12 | Olfactory bulb |
| MPZ | Olfactory bulb |
| C21ORF7 | Whole blood |
| FFAR2 | Whole blood |
| FCGR3A | Whole blood |
| EMR2 | Whole blood |
| FAM5B | Whole blood |
| FCGR3B | Whole blood |
| FPR2 | Whole blood |
| MLH3 | Whole blood |
| PF4 | Whole blood |
| PF4V1 | Whole blood |

FIG. 15D

| | |
|---|---|
| PPBP | Whole blood |
| TLR1 | Whole blood |
| TNFRSF10C | Whole blood |
| ZDHHC18 | Whole blood |

Heatmap of Delta Ct values as compared to ACTB showing the presence of tissue specific transcripts in Cell-free RNA identified by qPCR

FIG. 18A

| Gene | Tissue |
|---|---|
| A4GALT | Uterus Corpus |
| A4GNT | Superior Cervical Ganglion |
| AADAC | small intestine |
| AASS | Ovary |
| ABCA12 | Tonsil |
| ABCA4 | retina |
| ABCB4 | CD19 Bcells neg. sel. |
| ABCB6 | CD71 Early Erythroid |
| ABCB7 | CD71 Early Erythroid |
| ABCC2 | Pancreatic Islet |
| ABCC3 | Adrenal Cortex |
| ABCC9 | Dorsal Root Ganglion |
| ABCF3 | Adrenal gland |
| ABCG1 | Lung |
| ABCG2 | CD71 Early Erythroid |
| ABHD4 | Adipocyte |
| ABHD5 | Whole Blood |
| ABHD6 | pineal night |
| ABHD8 | Whole Brain |
| ABO | Heart |
| ABT1 | X721 B lymphoblasts |

FIG. 18B

| | |
|---|---|
| ABTB2 | Placenta |
| ACAA1 | Liver |
| ACACB | Adipocyte |
| ACAD8 | Kidney |
| ACADL | Thyroid |
| ACADS | Liver |
| ACADSB | Fetal liver |
| ACAN | Trachea |
| ACBD4 | Liver |
| ACCN3 | Prefrontal Cortex |
| ACE2 | Testis Germ Cell |
| ACHE | CD71 Early Erythroid |
| ACLY | Adipocyte |
| ACOT1 | Adipocyte |
| ACOX2 | Liver |
| ACP2 | Liver |
| ACP5 | Lung |
| ACP6 | CD34 |
| ACPP | Prostate |
| ACR | Testis Intersitial |
| ACRV1 | Testis Intersitial |
| ACSBG2 | Testis Intersitial |
| ACSF2 | Kidney |
| ACSL4 | Fetal liver |

FIG. 18C

| | |
|---|---|
| ACSL5 | small intestine |
| ACSL6 | CD71 Early Erythroid |
| ACSM3 | Leukemia chronic Myelogenous K562 |
| ACSM5 | Liver |
| ACSS3 | Adipocyte |
| ACTA1 | Skeletal Muscle |
| ACTC1 | Heart |
| ACTG1 | CD71 Early Erythroid |
| ACTL7A | Testis Intersitial |
| ACTL7B | Testis Intersitial |
| ACTN3 | Skeletal Muscle |
| ACTR8 | Superior Cervical Ganglion |
| ADA | Leukemia lymphoblastic MOLT 4 |
| ADAM12 | Placenta |
| ADAM17 | CD33 Myeloid |
| ADAM2 | Testis Intersitial |
| ADAM21 | Appendix |
| ADAM23 | Thalamus |
| ADAM28 | CD19 Bcells neg. sel. |
| ADAM30 | Testis Germ Cell |
| ADAM5P | Testis Intersitial |
| ADAM7 | Testis Leydig Cell |
| ADAMTS12 | Atrioventricular Node |

FIG. 18D

| | |
|---|---|
| ADAMTS20 | Appendix |
| ADAMTS3 | CD105 Endothelial |
| ADAMTS8 | Lung |
| ADAMTS9 | Dorsal Root Ganglion |
| ADAMTSL2 | Ciliary Ganglion |
| ADAMTSL3 | retina |
| ADAMTSL4 | Atrioventricular Node |
| ADARB2 | Skeletal Muscle |
| ADAT1 | CD71 Early Erythroid |
| ADCK4 | Ciliary Ganglion |
| ADCY1 | Fetal brain |
| ADCY9 | Lung |
| ADCYAP1 | Pancreatic Islet |
| ADH7 | Tongue |
| ADIPOR1 | Bone marrow |
| ADM2 | Pituitary |
| ADORA3 | Olfactory Bulb |
| ADRA1D | Skeletal Muscle |
| ADRA2A | Lymph node |
| ADRA2B | Superior Cervical Ganglion |
| ADRB1 | pineal night |
| AFF3 | Trigeminal Ganglion |
| AFF4 | Testis Intersitial |
| AGPAT2 | Adipocyte |

FIG. 18E

| | |
|---|---|
| AGPAT3 | CD33 Myeloid |
| AGPAT4 | CD71 Early Erythroid |
| AGPS | Testis Interstitial |
| AGR2 | Trachea |
| AGRN | Colorectal adenocarcinoma |
| AGRP | Superior Cervical Ganglion |
| AGXT | Liver |
| AIFM1 | X721 B lymphoblasts |
| AIM2 | CD19 Bcells neg. sel. |
| AJAP1 | BDCA4 Dentritic Cells |
| AKAP10 | CD33 Myeloid |
| AKAP3 | Testis Interstitial |
| AKAP6 | Medulla Oblongata |
| AKAP7 | Fetal brain |
| AKAP8L | CD71 Early Erythroid |
| AKR1C4 | Liver |
| AKR7A3 | Liver |
| AKT2 | Thyroid |
| ALAD | CD71 Early Erythroid |
| ALDH3B2 | Tongue |
| ALDH6A1 | Kidney |
| ALDH7A1 | Ovary |
| ALDOA | Skeletal Muscle |
| ALG12 | CD4 T cells |

FIG. 18F

| | |
|---|---|
| ALG13 | CD19 Bcells neg. sel. |
| ALG3 | Liver |
| ALOX12 | Whole Blood |
| ALOX12B | Tonsil |
| ALOX15B | Prostate |
| ALPI | small intestine |
| ALPK3 | Skeletal Muscle |
| ALPL | Whole Blood |
| ALPP | Placenta |
| ALPPL2 | Placenta |
| ALX1 | Superior Cervical Ganglion |
| ALX4 | Superior Cervical Ganglion |
| AMBN | pineal day |
| AMDHD2 | BDCA4 Dentritic Cells |
| AMELY | Subthalamic Nucleus |
| AMHR2 | Heart |
| AMPD1 | Skeletal Muscle |
| AMPD2 | pineal night |
| AMPD3 | CD71 Early Erythroid |
| ANAPC1 | X721 B lymphoblasts |
| ANG | Liver |
| ANGEL2 | CD8 T cells |
| ANGPT1 | CD35 |
| ANGPT2 | Ciliary Ganglion |

FIG. 18G

| | |
|---|---|
| ANGPTL2 | Uterus Corpus |
| ANGPTL3 | Fetal liver |
| ANK1 | CD71 Early Erythroid |
| ANKFY1 | CD8 T cells |
| ANKH | Cerebellum Peduncles |
| ANKLE2 | Testis |
| ANKRD1 | Skeletal Muscle |
| ANKRD2 | Skeletal Muscle |
| ANKRD34C | Thalamus |
| ANKRD5 | Skeletal Muscle |
| ANKRD53 | Skeletal Muscle |
| ANKRD57 | Bronchial Epithelial Cells |
| ANKS1B | Superior Cervical Ganglion |
| ANTXR1 | Uterus Corpus |
| ANXA13 | small intestine |
| ANXA2P1 | Bronchial Epithelial Cells |
| ANXA2P3 | Bronchial Epithelial Cells |
| AOC2 | retina |
| AP1G1 | Testis Germ Cell |
| AP1M2 | Kidney |
| AP3S1 | Heart |
| APBA1 | Dorsal Root Ganglion |
| APBB1IP | Whole Blood |
| APBB2 | Superior Cervical Ganglion |

FIG. 18H

| | |
|---|---|
| APC | Fetal brain |
| APEX2 | Colorectal adenocarcinoma |
| APIP | Trachea |
| APOA1 | Liver |
| APOA4 | small intestine |
| APOB48R | Whole Blood |
| APOBEC1 | small intestine |
| APOBEC2 | Skeletal Muscle |
| APOBEC3B | Colorectal adenocarcinoma |
| APOC4 | Liver |
| APOF | Liver |
| APOL5 | Bone marrow |
| APOOL | Superior Cervical Ganglion |
| AQP2 | Kidney |
| AQP5 | Testis Intersitial |
| AQP7 | Adipocyte |
| AR | Liver |
| ARCN1 | Trigeminal Ganglion |
| ARFGAP1 | Lymphoma burkitts Raji |
| ARG1 | Fetal liver |
| ARHGAP11A | Trigeminal Ganglion |
| ARHGAP19 | Olfactory Bulb |
| ARHGAP22 | CD36 |
| ARHGAP28 | Testis Intersitial |

FIG. 18I

| | |
|---|---|
| ARHGAP6 | Prostate |
| ARHGEF1 | CD4 T cells |
| ARHGEF5 | Pancreas |
| ARHGEF7 | Thymus |
| ARID3A | Placenta |
| ARID3B | X721 B lymphoblasts |
| ARL15 | Uterus Corpus |
| ARMC4 | Superior Cervical Ganglion |
| ARMC8 | CD71 Early Erythroid |
| ARMCX5 | small intestine |
| ARR3 | retina |
| ARSA | Liver |
| ARSB | Superior Cervical Ganglion |
| ARSE | Liver |
| ARSF | Globus Pallidus |
| ART1 | Cardiac Myocytes |
| ART3 | Testis |
| ART4 | CD71 Early Erythroid |
| ASB1 | Trigeminal Ganglion |
| ASB7 | Globus Pallidus |
| ASB8 | Superior Cervical Ganglion |
| ASCC2 | CD71 Early Erythroid |
| ASCL2 | Superior Cervical Ganglion |
| ASCL3 | Superior Cervical Ganglion |

FIG. 18J

| | |
|---|---|
| ASF1A | CD71 Early Erythroid |
| ASIP | BDCA4 Dentritic Cells |
| ASL | Liver |
| ASPN | Uterus |
| ASPSCR1 | Colorectal adenocarcinoma |
| ASTE1 | CD8 T cells |
| ASTN2 | pineal day |
| ATF5 | Liver |
| ATG4A | CD71 Early Erythroid |
| ATG7 | CD14 Monocytes |
| ATN1 | Prefrontal Cortex |
| ATOH1 | Superior Cervical Ganglion |
| ATP10A | CD56 NK Cells |
| ATP10D | Placenta |
| ATP11A | Superior Cervical Ganglion |
| ATP12A | Trachea |
| ATP13A3 | Smooth Muscle |
| ATP1B3 | Adrenal Cortex |
| ATP2C2 | Colon |
| ATP4A | Adrenal gland |
| ATP4B | Parietal Lobe |
| ATP5G1 | Heart |
| ATP5G3 | Heart |
| ATP5J2 | Superior Cervical Ganglion |

FIG. 18K

| | |
|---|---|
| ATP6V0A2 | CD37 |
| ATP6V1B1 | Kidney |
| ATP7A | CD71 Early Erythroid |
| ATRIP | CD14 Monocytes |
| ATXN3L | Superior Cervical Ganglion |
| ATXN7L1 | Skeletal Muscle |
| AURKC | Testis Seminiferous Tubule |
| AVEN | Bronchial Epithelial Cells |
| AVIL | Dorsal Root Ganglion |
| AVP | Hypothalamus |
| AXIN1 | CD56 NK Cells |
| AXL | Cardiac Myocytes |
| AZI1 | CD71 Early Erythroid |
| B3GALNT1 | Amygdala |
| B3GALT5 | CD105 Endothelial |
| B3GNT2 | CD71 Early Erythroid |
| B3GNT3 | Placenta |
| B3GNTL1 | CD38 |
| BAAT | Liver |
| BACH2 | Lymphoma burkitts Daudi |
| BAD | Whole Brain |
| BAG2 | Uterus |
| BAG4 | Superior Cervical Ganglion |
| BAI1 | Cingulate Cortex |

FIG. 18L

| | |
|---|---|
| BAIAP2 | Liver |
| BAIAP2L2 | Superior Cervical Ganglion |
| BAMBI | Colorectal adenocarcinoma |
| BANK1 | CD19 Bcells neg. sel. |
| BARD1 | X721 B lymphoblasts |
| BARX1 | Atrioventricular Node |
| BATF3 | X721 B lymphoblasts |
| BBOX1 | Kidney |
| BBS4 | pineal day |
| BCAM | Thyroid |
| BCAR3 | Placenta |
| BCAS3 | X721 B lymphoblasts |
| BCKDK | Liver |
| BCL10 | Colon |
| BCL2L1 | CD71 Early Erythroid |
| BCL2L10 | Trigeminal Ganglion |
| BCL2L13 | pineal day |
| BCL2L14 | Testis |
| BCL3 | Whole Blood |
| BDH1 | Liver |
| BDKRB1 | Smooth Muscle |
| BDKRB2 | Smooth Muscle |
| BDNF | Smooth Muscle |
| BECN1 | Ciliary Ganglion |

FIG. 18M

| | |
|---|---|
| BEST1 | retina |
| BET1L | Superior Cervical Ganglion |
| BHLHB9 | pineal night |
| BIRC3 | CD19 Bcells neg. sel. |
| BLK | CD19 Bcells neg. sel. |
| BLVRA | CD105 Endothelial |
| BMP1 | Placenta |
| BMP2K | CD71 Early Erythroid |
| BMP3 | Temporal Lobe |
| BMP5 | Trigeminal Ganglion |
| BMP8A | Fetal Thyroid |
| BMP8B | Superior Cervical Ganglion |
| BMPR1B | Skeletal Muscle |
| BNC1 | Bronchial Epithelial Cells |
| BNC2 | Uterus |
| BNIP3L | CD71 Early Erythroid |
| BOK | Thalamus |
| BPHL | Kidney |
| BPI | Bone marrow |
| BPY2 | Adrenal gland |
| BRAF | Superior Cervical Ganglion |
| BRAP | Testis Intersitial |
| BRE | Adrenal gland |
| BRS3 | Skeletal Muscle |

FIG. 18N

| | |
|---|---|
| BRSK2 | Cerebellum Peduncles |
| BSDC1 | CD71 Early Erythroid |
| BTBD2 | Prefrontal Cortex |
| BTD | Superior Cervical Ganglion |
| BTN2A3 | Appendix |
| BTN3A1 | CD8 T cells |
| BTRC | CD71 Early Erythroid |
| BUB1 | X721 B lymphoblasts |
| BYSL | Leukemia chronic Myelogenous K563 |
| C10orf118 | Testis Leydig Cell |
| C10orf119 | CD33 Myeloid |
| C10orf28 | Superior Cervical Ganglion |
| C10orf57 | Ciliary Ganglion |
| C10orf72 | Adrenal Cortex |
| C10orf76 | CD19 Bcells neg. sel. |
| C10orf81 | Dorsal Root Ganglion |
| C10orf84 | Superior Cervical Ganglion |
| C10orf88 | Testis Seminiferous Tubule |
| C10orf95 | Superior Cervical Ganglion |
| C11orf41 | Fetal brain |
| C11orf48 | Adipocyte |
| C11orf57 | Appendix |
| C11orf67 | Skeletal Muscle |

FIG. 18O

| | |
|---|---|
| C11orf71 | Thyroid |
| C11orf80 | Leukemia lymphoblastic MOLT 5 |
| C12orf4 | CD71 Early Erythroid |
| C12orf43 | Whole Brain |
| C12orf47 | CD8 T cells |
| C12orf49 | CD56 NK Cells |
| C13orf23 | Placenta |
| C13orf27 | Testis Leydig Cell |
| C13orf34 | CD71 Early Erythroid |
| C14orf106 | CD33 Myeloid |
| C14orf118 | Superior Cervical Ganglion |
| C14orf138 | CD19 Bcells neg. sel. |
| C14orf162 | Cerebellum |
| C14orf169 | Testis |
| C14orf56 | Superior Cervical Ganglion |
| C15orf2 | Cerebellum |
| C15orf29 | Fetal brain |
| C15orf39 | Whole Blood |
| C15orf44 | Testis |
| C15orf5 | Superior Cervical Ganglion |
| C16orf3 | Dorsal Root Ganglion |
| C16orf53 | pineal day |
| C16orf59 | CD71 Early Erythroid |

FIG. 18P

| | |
|---|---|
| C16orf68 | Testis |
| C16orf71 | Testis Seminiferous Tubule |
| C17orf42 | X721 B lymphoblasts |
| C17orf53 | Dorsal Root Ganglion |
| C17orf59 | Dorsal Root Ganglion |
| C17orf68 | CD8 T cells |
| C17orf73 | Cardiac Myocytes |
| C17orf80 | Testis Germ Cell |
| C17orf81 | Testis Intersitial |
| C17orf85 | BDCA4 Dentritic Cells |
| C17orf88 | Superior Cervical Ganglion |
| C19orf29 | Leukemia chronic Myelogenous K564 |
| C19orf61 | Leukemia lymphoblastic MOLT 6 |
| C1GALT1C1 | Superior Cervical Ganglion |
| C1orf103 | Leukemia chronic Myelogenous K565 |
| C1orf105 | Testis Intersitial |
| C1orf106 | small intestine |
| C1orf114 | Testis Intersitial |
| C1orf135 | Testis |
| C1orf14 | Testis Leydig Cell |
| C1orf156 | CD19 Bcells neg. sel. |
| C1orf175 | Testis Intersitial |

FIG. 18Q

| | |
|---|---|
| C1orf222 | Testis |
| C1orf25 | CD71 Early Erythroid |
| C1orf27 | pineal night |
| C1orf35 | CD71 Early Erythroid |
| C1orf50 | Testis |
| C1orf66 | Leukemia chronic Myelogenous K566 |
| C1orf68 | Liver |
| C1orf89 | Atrioventricular Node |
| C1orf9 | CD71 Early Erythroid |
| C1QTNF1 | Smooth Muscle |
| C1QTNF3 | Spinal Cord |
| C2 | Liver |
| C20orf191 | Superior Cervical Ganglion |
| C20orf29 | Superior Cervical Ganglion |
| C21orf45 | CD105 Endothelial |
| C21orf7 | Whole Blood |
| C21orf91 | Testis Intersitial |
| C22orf24 | Superior Cervical Ganglion |
| C22orf26 | Ciliary Ganglion |
| C22orf30 | Trigeminal Ganglion |
| C22orf31 | Uterus Corpus |
| C2CD2 | Adrenal Cortex |
| C2orf18 | Cerebellum |

FIG. 18R

| | |
|---|---|
| C2orf34 | pineal day |
| C2orf42 | Testis |
| C2orf43 | X721 B lymphoblasts |
| C2orf54 | Trigeminal Ganglion |
| C3AR1 | CD14 Monocytes |
| C3orf37 | Lymphoma burkitts Daudi |
| C3orf64 | pineal day |
| C4orf19 | Placenta |
| C4orf23 | Superior Cervical Ganglion |
| C4orf6 | Superior Cervical Ganglion |
| C5 | Fetal liver |
| C5AR1 | Whole Blood |
| C5orf23 | CD39 |
| C5orf28 | Thyroid |
| C5orf4 | CD71 Early Erythroid |
| C5orf42 | Superior Cervical Ganglion |
| C6orf103 | Testis Intersitial |
| C6orf105 | Colon |
| C6orf108 | Lymphoma burkitts Raji |
| C6orf124 | Fetal brain |
| C6orf162 | Pituitary |
| C6orf208 | Superior Cervical Ganglion |
| C6orf25 | Superior Cervical Ganglion |
| C6orf27 | Superior Cervical Ganglion |

FIG. 18S

| | |
|---|---|
| C6orf35 | Appendix |
| C6orf54 | Skeletal Muscle |
| C6orf64 | Testis |
| C7orf10 | Bronchial Epithelial Cells |
| C7orf25 | Superior Cervical Ganglion |
| C7orf58 | Leukemia chronic Myelogenous K567 |
| C8G | Liver |
| C8orf17 | Superior Cervical Ganglion |
| C8orf41 | Leukemia lymphoblastic MOLT 7 |
| C9 | Liver |
| C9orf116 | Testis |
| C9orf27 | Trigeminal Ganglion |
| C9orf3 | Uterus |
| C9orf38 | Superior Cervical Ganglion |
| C9orf40 | CD71 Early Erythroid |
| C9orf46 | Bronchial Epithelial Cells |
| C9orf68 | Skeletal Muscle |
| C9orf86 | CD71 Early Erythroid |
| C9orf9 | Testis Intersitial |
| CA1 | CD71 Early Erythroid |
| CA12 | Kidney |
| CA3 | Thyroid |
| CA4 | Lung |

FIG. 18T

| | |
|---|---|
| CA5A | Liver |
| CA5B | Superior Cervical Ganglion |
| CA6 | Salivary gland |
| CA7 | Atrioventricular Node |
| CA9 | Skin |
| CAB39L | Prostate |
| CABP5 | retina |
| CABYR | Testis Interstitial |
| CACNA1B | Superior Cervical Ganglion |
| CACNA1D | Pancreas |
| CACNA1E | Superior Cervical Ganglion |
| CACNA1F | pineal day |
| CACNA1G | Cerebellum |
| CACNA1H | Adrenal Cortex |
| CACNA1I | Prefrontal Cortex |
| CACNA1S | Skeletal Muscle |
| CACNA2D1 | Superior Cervical Ganglion |
| CACNA2D3 | CD14 Monocytes |
| CACNB1 | Skeletal Muscle |
| CACNG2 | Cerebellum Peduncles |
| CACNG4 | Skeletal Muscle |
| CADM4 | Prostate |
| CADPS2 | Cerebellum Peduncles |
| CALCA | Dorsal Root Ganglion |

FIG. 18U

| | |
|---|---|
| CALCRL | Fetal lung |
| CALML5 | Skin |
| CAMK1G | Whole Brain |
| CAMK4 | Testis Intersitial |
| CAMTA2 | pineal night |
| CAND2 | Heart |
| CANT1 | Prostate |
| CAPN5 | Colon |
| CAPN6 | Placenta |
| CAPN7 | Superior Cervical Ganglion |
| CARD14 | CD71 Early Erythroid |
| CASP10 | CD4 T cells |
| CASP2 | Leukemia lymphoblastic MOLT 8 |
| CASP9 | Adrenal Cortex |
| CASQ2 | Heart |
| CASR | Kidney |
| CASS4 | Cingulate Cortex |
| CATSPERB | Superior Cervical Ganglion |
| CAV3 | Superior Cervical Ganglion |
| CBFA2T3 | BDCA4 Dentritic Cells |
| CBL | Testis Germ Cell |
| CBLC | Bronchial Epithelial Cells |
| CBX2 | Trachea |

FIG. 18V

| | |
|---|---|
| CCBP2 | Superior Cervical Ganglion |
| CCDC132 | Trigeminal Ganglion |
| CCDC19 | Testis Intersitial |
| CCDC21 | CD71 Early Erythroid |
| CCDC25 | CD33 Myeloid |
| CCDC28B | Lymphoma burkitts Raji |
| CCDC33 | Superior Cervical Ganglion |
| CCDC41 | CD40 |
| CCDC46 | Testis Intersitial |
| CCDC51 | Leukemia promyelocytic HL60 |
| CCDC6 | Colon |
| CCDC64 | CD8 T cells |
| CCDC68 | Fetal lung |
| CCDC76 | CD8 T cells |
| CCDC81 | Superior Cervical Ganglion |
| CCDC87 | Testis |
| CCDC88A | BDCA4 Dentritic Cells |
| CCDC88C | CD56 NK Cells |
| CCDC99 | Leukemia lymphoblastic MOLT 9 |
| CCHCR1 | Testis |
| CCIN | Testis Intersitial |
| CCKAR | Uterus Corpus |
| CCL11 | Smooth Muscle |

FIG. 18W

| | |
|---|---|
| CCL13 | small intestine |
| CCL18 | Thymus |
| CCL2 | Smooth Muscle |
| CCL21 | Lymph node |
| CCL22 | X721 B lymphoblasts |
| CCL24 | Uterus Corpus |
| CCL27 | Skin |
| CCL3 | CD33 Myeloid |
| CCL4 | CD56 NK Cells |
| CCL7 | Smooth Muscle |
| CCND1 | Colorectal adenocarcinoma |
| CCNF | CD71 Early Erythroid |
| CCNJ | Ciliary Ganglion |
| CCNJL | Atrioventricular Node |
| CCNL2 | CD4 T cells |
| CCNO | Testis |
| CCR10 | X721 B lymphoblasts |
| CCR3 | Whole Blood |
| CCR5 | CD8 T cells |
| CCR6 | CD19 Bcells neg. sel. |
| CCRL2 | CD71 Early Erythroid |
| CCRN4L | Appendix |
| CCS | CD71 Early Erythroid |
| CCT4 | Superior Cervical Ganglion |

FIG. 18X

| | |
|---|---|
| CD160 | CD56 NK Cells |
| CD180 | CD19 Bcells neg. sel. |
| CD1C | Thymus |
| CD207 | Appendix |
| CD209 | Lymph node |
| CD22 | Lymphoma burkitts Raji |
| CD226 | Superior Cervical Ganglion |
| CD244 | CD56 NK Cells |
| CD248 | Adipocyte |
| CD320 | Heart |
| CD3EAP | Dorsal Root Ganglion |
| CD3G | Thymus |
| CD4 | BDCA4 Dentritic Cells |
| CD40 | Lymphoma burkitts Raji |
| CD40LG | CD41 |
| CD5L | CD105 Endothelial |
| CD79B | Lymphoma burkitts Raji |
| CD80 | X721 B lymphoblasts |
| CD81 | CD71 Early Erythroid |
| CDC14A | Testis |
| CDC25C | Testis Intersitial |
| CDC27 | CD71 Early Erythroid |
| CDC34 | CD71 Early Erythroid |
| CDC42EP2 | Smooth Muscle |

FIG. 18Y

| | |
|---|---|
| CDC6 | Colorectal adenocarcinoma |
| CDC73 | Colon |
| CDCA4 | CD71 Early Erythroid |
| CDCP1 | Bronchial Epithelial Cells |
| CDH13 | Uterus |
| CDH15 | Cerebellum |
| CDH18 | Subthalamic Nucleus |
| CDH20 | Superior Cervical Ganglion |
| CDH22 | Cerebellum Peduncles |
| CDH3 | Bronchial Epithelial Cells |
| CDH4 | Amygdala |
| CDH5 | Placenta |
| CDH6 | Trigeminal Ganglion |
| CDH7 | Skeletal Muscle |
| CDK5R2 | Whole Brain |
| CDK6 | CD42 |
| CDK8 | Colorectal adenocarcinoma |
| CDKL2 | Superior Cervical Ganglion |
| CDKL3 | Superior Cervical Ganglion |
| CDKL5 | Superior Cervical Ganglion |
| CDKN2D | CD71 Early Erythroid |
| CDON | Tonsil |
| CDR1 | Cerebellum |
| CDS1 | small intestine |

FIG. 18Z

| | |
|---|---|
| CDSN | Skin |
| CDX4 | Superior Cervical Ganglion |
| CDYL | CD71 Early Erythroid |
| CEACAM21 | Bone marrow |
| CEACAM3 | Whole Blood |
| CEACAM5 | Colon |
| CEACAM7 | Colon |
| CEACAM8 | Bone marrow |
| CEBPA | Liver |
| CEBPE | Bone marrow |
| CELSR3 | Fetal brain |
| CEMP1 | Skeletal Muscle |
| CENPE | CD71 Early Erythroid |
| CENPI | Appendix |
| CENPQ | Trigeminal Ganglion |
| CENPT | CD71 Early Erythroid |
| CEP170 | Fetal brain |
| CEP55 | X721 B lymphoblasts |
| CEP63 | Whole Blood |
| CEP76 | CD71 Early Erythroid |
| CER1 | Superior Cervical Ganglion |
| CES1 | Liver |
| CES2 | Liver |
| CES3 | Colon |

FIG. 18AA

| | |
|---|---|
| CETN1 | Testis |
| CFHR4 | Liver |
| CFHR5 | Liver |
| CFI | Fetal liver |
| CGB | Placenta |
| CGRRF1 | Testis Intersitial |
| CHAD | Trachea |
| CHAF1A | Leukemia lymphoblastic MOLT 10 |
| CHAF1B | Leukemia lymphoblastic MOLT 11 |
| CHAT | Uterus Corpus |
| CHD3 | Fetal brain |
| CHD8 | Trigeminal Ganglion |
| CHI3L1 | Uterus Corpus |
| CHIA | Lung |
| CHIT1 | Lymph node |
| CHKA | Testis Intersitial |
| CHML | Superior Cervical Ganglion |
| CHMP1B | Superior Cervical Ganglion |
| CHMP6 | Heart |
| CHODL | Testis Germ Cell |
| CHPF | Colorectal adenocarcinoma |
| CHRM2 | Skeletal Muscle |
| CHRM3 | Prefrontal Cortex |

FIG. 18AB

| | |
|---|---|
| CHRM4 | Superior Cervical Ganglion |
| CHRM5 | Skeletal Muscle |
| CHRNA2 | Heart |
| CHRNA4 | Skeletal Muscle |
| CHRNA5 | Appendix |
| CHRNA6 | Temporal Lobe |
| CHRNA9 | Appendix |
| CHRNB3 | Superior Cervical Ganglion |
| CHST10 | Whole Brain |
| CHST12 | CD56 NK Cells |
| CHST3 | Testis Germ Cell |
| CHST4 | Uterus Corpus |
| CHST7 | Ovary |
| CHSY1 | Placenta |
| CIB2 | BDCA4 Dentritic Cells |
| CIDEA | Ciliary Ganglion |
| CIDEB | Liver |
| CIDEC | Adipocyte |
| CISH | Leukemia chronic Myelogenous K568 |
| CKAP2 | CD71 Early Erythroid |
| CKM | Skeletal Muscle |
| CLCA4 | Colon |
| CLCF1 | Uterus Corpus |

FIG. 18AC

| | |
|---|---|
| CLCN1 | Skeletal Muscle |
| CLCN2 | Olfactory Bulb |
| CLCN5 | Appendix |
| CLCN6 | Whole Brain |
| CLCNKA | Kidney |
| CLCNKB | Kidney |
| CLDN10 | Kidney |
| CLDN11 | Heart |
| CLDN15 | small intestine |
| CLDN4 | Colorectal adenocarcinoma |
| CLDN7 | Colon |
| CLDN8 | Salivary gland |
| CLEC11A | CD43 |
| CLEC16A | Lymphoma burkitts Raji |
| CLEC4M | Lymph node |
| CLEC5A | CD33 Myeloid |
| CLGN | Testis Intersitial |
| CLIC2 | CD71 Early Erythroid |
| CLIC5 | Skeletal Muscle |
| CLMN | Testis Intersitial |
| CLN3 | Placenta |
| CLN5 | Thyroid |
| CLN6 | pineal day |
| CLPB | Testis Intersitial |

FIG. 18AD

| | |
|---|---|
| CLTCL1 | Testis |
| CLUL1 | retina |
| CMA1 | Adrenal Cortex |
| CMAH | Uterus |
| CMAS | CD71 Early Erythroid |
| CMKLR1 | BDCA4 Dentritic Cells |
| CNGA1 | Uterus Corpus |
| CNIH3 | Amygdala |
| CNNM1 | Prefrontal Cortex |
| CNNM4 | pineal day |
| CNR1 | Fetal brain |
| CNR2 | Uterus Corpus |
| CNTFR | Cardiac Myocytes |
| CNTLN | Trigeminal Ganglion |
| CNTN2 | Thalamus |
| COBLL1 | Placenta |
| COG7 | Prostate |
| COL11A1 | Adipocyte |
| COL13A1 | Cardiac Myocytes |
| COL14A1 | Uterus |
| COL17A1 | Bronchial Epithelial Cells |
| COL19A1 | Trigeminal Ganglion |
| COL7A1 | Skin |
| COL8A2 | retina |

FIG. 18AE

| | |
|---|---|
| COL9A1 | pineal night |
| COL9A2 | retina |
| COLEC10 | Appendix |
| COLEC11 | Liver |
| COMP | Adipocyte |
| COMT | Liver |
| COQ4 | Thyroid |
| COQ6 | Testis |
| CORIN | Superior Cervical Ganglion |
| CORO1B | CD14 Monocytes |
| CORO2A | Bronchial Epithelial Cells |
| COX6B1 | Superior Cervical Ganglion |
| CP | Fetal liver |
| CPA3 | CD44 |
| CPM | Adipocyte |
| CPN2 | Liver |
| CPNE6 | Amygdala |
| CPNE7 | Leukemia chronic Myelogenous K569 |
| CPOX | Fetal liver |
| CPT1A | X721 B lymphoblasts |
| CPZ | Placenta |
| CR1 | Whole Blood |
| CREBZF | CD8 T cells |

FIG. 18AF

| | |
|---|---|
| CRH | Placenta |
| CRHR1 | Cerebellum Peduncles |
| CRIM1 | Placenta |
| CRISP2 | Testis Intersitial |
| CRLF1 | Adipocyte |
| CRLF2 | Skeletal Muscle |
| CRTAC1 | Lung |
| CRTAP | Adipocyte |
| CRY2 | pineal night |
| CRYAA | Kidney |
| CRYBA2 | Pancreatic Islet |
| CRYBA4 | Superior Cervical Ganglion |
| CRYBB1 | Superior Cervical Ganglion |
| CRYBB2 | retina |
| CRYBB3 | Superior Cervical Ganglion |
| CSAD | Fetal brain |
| CSAG2 | Leukemia chronic Myelogenous K570 |
| CSDC2 | Heart |
| CSF2 | Colorectal adenocarcinoma |
| CSF2RA | BDCA4 Dentritic Cells |
| CSF3 | Smooth Muscle |
| CSF3R | Whole Blood |
| CSN3 | Salivary gland |

FIG. 18AG

| | |
|---|---|
| CSNK1G3 | CD19 Bcells neg. sel. |
| CSPG4 | Trigeminal Ganglion |
| CST2 | Salivary gland |
| CST4 | Salivary gland |
| CST5 | Salivary gland |
| CST7 | CD56 NK Cells |
| CSTF2T | CD105 Endothelial |
| CTAG2 | X721 B lymphoblasts |
| CTBS | Whole Blood |
| CTDSPL | Colorectal adenocarcinoma |
| CTF1 | Superior Cervical Ganglion |
| CTLA4 | Superior Cervical Ganglion |
| CTNNA3 | Testis Intersitial |
| CTPS2 | Ciliary Ganglion |
| CTSD | Lung |
| CTSG | Bone marrow |
| CTSK | Uterus Corpus |
| CTTNBP2NL | CD8 T cells |
| CUBN | Kidney |
| CUEDC1 | BDCA4 Dentritic Cells |
| CUL1 | Testis Intersitial |
| CUL7 | Smooth Muscle |
| CXCL1 | Smooth Muscle |
| CXCL3 | Smooth Muscle |

FIG. 18AH

| | |
|---|---|
| CXCL5 | Smooth Muscle |
| CXCL6 | Smooth Muscle |
| CXCR3 | BDCA4 Dentritic Cells |
| CXCR5 | CD19 Bcells neg. sel. |
| CXorf1 | pineal day |
| CXorf40A | Adrenal Cortex |
| CXorf56 | Superior Cervical Ganglion |
| CXorf57 | Hypothalamus |
| CYB561 | Prostate |
| CYLC1 | Testis Seminiferous Tubule |
| CYLD | CD4 T cells |
| CYorf15B | CD4 T cells |
| CYP19A1 | Placenta |
| CYP1A1 | Lung |
| CYP1A2 | Liver |
| CYP20A1 | BDCA4 Dentritic Cells |
| CYP26A1 | Fetal brain |
| CYP27A1 | Liver |
| CYP27B1 | Bronchial Epithelial Cells |
| CYP2A6 | Liver |
| CYP2A7 | Liver |
| CYP2B7P1 | Superior Cervical Ganglion |
| CYP2C19 | Atrioventricular Node |
| CYP2C8 | Liver |

FIG. 18AI

| | |
|---|---|
| CYP2C9 | Liver |
| CYP2D6 | Liver |
| CYP2E1 | Liver |
| CYP2F1 | Superior Cervical Ganglion |
| CYP2W1 | Skin |
| CYP3A43 | Liver |
| CYP3A5 | small intestine |
| CYP3A7 | Fetal liver |
| CYP4F11 | Liver |
| CYP4F2 | Liver |
| CYP4F8 | Prostate |
| CYP7B1 | Ciliary Ganglion |
| DACT1 | Fetal brain |
| DAGLA | Amygdala |
| DAO | Kidney |
| DAPK2 | Atrioventricular Node |
| DAZ1 | Testis Leydig Cell |
| DAZL | Testis |
| DBI | CD71 Early Erythroid |
| DBNDD1 | Trigeminal Ganglion |
| DBP | Thyroid |
| DCBLD2 | Trigeminal Ganglion |
| DCC | Testis Seminiferous Tubule |
| DCHS2 | Cerebellum |

FIG. 18AJ

| | |
|---|---|
| DCI | Liver |
| DCLRE1A | X721 B lymphoblasts |
| DCP1A | CD4 T cells |
| DCT | retina |
| DCUN1D1 | CD71 Early Erythroid |
| DCUN1D2 | Heart |
| DCX | Fetal brain |
| DDX10 | Leukemia promyelocytic HL61 |
| DDX17 | Heart |
| DDX23 | Thymus |
| DDX25 | Testis Leydig Cell |
| DDX28 | CD14 Monocytes |
| DDX31 | Superior Cervical Ganglion |
| DDX43 | Testis Seminiferous Tubule |
| DDX5 | Liver |
| DDX51 | BDCA4 Dentritic Cells |
| DDX52 | Colorectal adenocarcinoma |
| DECR2 | Liver |
| DEFA4 | Bone marrow |
| DEFA5 | small intestine |
| DEFA6 | small intestine |
| DEFB126 | Testis Germ Cell |
| DEGS1 | Skin |

FIG. 18AK

| | |
|---|---|
| DENND1A | X721 B lymphoblasts |
| DENND2A | Atrioventricular Node |
| DENND3 | CD33 Myeloid |
| DENND4A | pineal night |
| DEPDC5 | Lymphoma burkitts Raji |
| DES | Skeletal Muscle |
| DGAT1 | small intestine |
| DGCR14 | Testis Intersitial |
| DGCR6L | Trigeminal Ganglion |
| DGCR8 | Leukemia chronic Myelogenous K571 |
| DGKA | CD4 T cells |
| DGKB | Caudate nucleus |
| DGKE | Superior Cervical Ganglion |
| DGKG | Cerebellum |
| DGKQ | Superior Cervical Ganglion |
| DHDDS | pineal day |
| DHODH | Liver |
| DHRS1 | Liver |
| DHRS12 | Liver |
| DHRS2 | Colorectal adenocarcinoma |
| DHRS9 | Trachea |
| DHTKD1 | Liver |
| DHX29 | CD71 Early Erythroid |

FIG. 18AL

| | |
|---|---|
| DHX35 | Leukemia lymphoblastic MOLT 12 |
| DHX38 | CD56 NK Cells |
| DHX57 | Testis Seminiferous Tubule |
| DIAPH2 | Testis Germ Cell |
| DIDO1 | CD8 T cells |
| DIO2 | Thyroid |
| DIO3 | Cerebellum Peduncles |
| DKFZP434L187 | Atrioventricular Node |
| DKK2 | Ciliary Ganglion |
| DKK4 | Pancreas |
| DLAT | Adipocyte |
| DLEU2 | CD71 Early Erythroid |
| DLG3 | Fetal brain |
| DLK2 | Testis Leydig Cell |
| DLL3 | Fetal brain |
| DLX2 | Fetal brain |
| DLX4 | Placenta |
| DLX5 | Placenta |
| DMC1 | Superior Cervical Ganglion |
| DMD | Olfactory Bulb |
| DMPK | Heart |
| DMWD | Atrioventricular Node |
| DNA2 | X721 B lymphoblasts |

FIG. 18AM

| | |
|---|---|
| DNAH17 | Testis |
| DNAH2 | Atrioventricular Node |
| DNAH9 | Cardiac Myocytes |
| DNAI1 | Testis |
| DNAI2 | Testis |
| DNAJC1 | CD56 NK Cells |
| DNAJC9 | CD71 Early Erythroid |
| DNAL4 | Testis |
| DNALI1 | Testis Intersitial |
| DNASE1L1 | CD14 Monocytes |
| DNASE1L2 | Tonsil |
| DNASE1L3 | BDCA4 Dentritic Cells |
| DNASE2B | Salivary gland |
| DND1 | Testis |
| DNM2 | BDCA4 Dentritic Cells |
| DNMT3A | Superior Cervical Ganglion |
| DNMT3B | Leukemia chronic Myelogenous K572 |
| DNMT3L | Liver |
| DOC2B | Adrenal gland |
| DOCK5 | Superior Cervical Ganglion |
| DOCK6 | Lung |
| DOK2 | CD14 Monocytes |
| DOK3 | Superior Cervical Ganglion |

FIG. 18AN

| | |
|---|---|
| DOK4 | Fetal brain |
| DOK5 | Fetal brain |
| DOLK | Testis |
| DOPEY2 | Skeletal Muscle |
| DOT1L | Superior Cervical Ganglion |
| DPAGT1 | X721 B lymphoblasts |
| DPEP3 | Testis |
| DPF3 | Cerebellum |
| DPH2 | Skeletal Muscle |
| DPM2 | CD71 Early Erythroid |
| DPP4 | Smooth Muscle |
| DPPA4 | CD45 |
| DPT | Adipocyte |
| DPY19L2P2 | Leukemia lymphoblastic MOLT 13 |
| DRD2 | Caudate nucleus |
| DSC1 | Skin |
| DSG1 | Skin |
| DTL | CD105 Endothelial |
| DTX2 | Skeletal Muscle |
| DTYMK | CD105 Endothelial |
| DUSP10 | X721 B lymphoblasts |
| DUSP26 | Skeletal Muscle |
| DUSP4 | Placenta |

FIG. 18AO

| | |
|---|---|
| DUSP7 | Bronchial Epithelial Cells |
| DVL3 | Placenta |
| DYNC2H1 | Pituitary |
| DYRK2 | CD8 T cells |
| DYRK4 | Testis Intersitial |
| DYSF | Whole Blood |
| E2F1 | CD71 Early Erythroid |
| E2F2 | CD71 Early Erythroid |
| E2F4 | CD71 Early Erythroid |
| E2F5 | Lymphoma burkitts Daudi |
| E2F8 | CD71 Early Erythroid |
| E4F1 | CD4 T cells |
| EAF2 | CD19 Bcells neg. sel. |
| EBI3 | Placenta |
| ECHDC1 | Adipocyte |
| ECHS1 | Liver |
| ECM1 | Tongue |
| ECSIT | Heart |
| EDA | Trigeminal Ganglion |
| EDA2R | Superior Cervical Ganglion |
| EDC3 | Testis |
| EDIL3 | Occipital Lobe |
| EDN2 | Superior Cervical Ganglion |
| EDN3 | retina |

FIG. 18AP

| | |
|---|---|
| EDNRA | Uterus |
| EFCAB1 | Superior Cervical Ganglion |
| EFHC1 | Testis Intersitial |
| EFHC2 | Appendix |
| EFNA4 | Prostate |
| EFNB1 | Colorectal adenocarcinoma |
| EFNB3 | Fetal brain |
| EGF | Kidney |
| EGFR | Placenta |
| EGLN1 | Whole Blood |
| EIF1AY | CD71 Early Erythroid |
| EIF2AK1 | CD71 Early Erythroid |
| EIF2B4 | Testis |
| EIF2C2 | CD71 Early Erythroid |
| EIF2C3 | Pituitary |
| EIF3K | Superior Cervical Ganglion |
| EIF4G2 | Liver |
| EIF5A2 | Ciliary Ganglion |
| ELF3 | Colon |
| ELL2 | Pancreatic Islet |
| ELMO3 | CD71 Early Erythroid |
| ELOVL6 | Adipocyte |
| ELSPBP1 | Testis Leydig Cell |
| ELTD1 | Smooth Muscle |

FIG. 18AQ

| | |
|---|---|
| EMID1 | Fetal brain |
| EMILIN2 | Superior Cervical Ganglion |
| EML1 | Fetal brain |
| EMR3 | Whole Blood |
| EMX2 | Uterus |
| EN1 | Adipocyte |
| ENDOG | Liver |
| ENO3 | Skeletal Muscle |
| ENOX1 | Fetal brain |
| ENPP1 | Thyroid |
| ENTPD1 | X721 B lymphoblasts |
| ENTPD2 | Superior Cervical Ganglion |
| ENTPD3 | Caudate nucleus |
| ENTPD4 | Smooth Muscle |
| ENTPD7 | Bone marrow |
| EPB41 | CD71 Early Erythroid |
| EPB41L4A | Trigeminal Ganglion |
| EPHA1 | Liver |
| EPHA3 | Fetal brain |
| EPHA5 | Fetal brain |
| EPN2 | CD71 Early Erythroid |
| EPN3 | Thalamus |
| EPS15L1 | Appendix |
| EPS8L1 | Placenta |

FIG. 18AR

| | |
|---|---|
| EPS8L3 | Pancreas |
| EPX | Bone marrow |
| EPYC | Placenta |
| ERCC1 | Heart |
| ERCC4 | Superior Cervical Ganglion |
| ERCC6 | Ovary |
| ERCC8 | Uterus Corpus |
| EREG | CD46 |
| ERF | Ciliary Ganglion |
| ERG | CD47 |
| ERICH1 | Superior Cervical Ganglion |
| ERLIN2 | Thyroid |
| ERMAP | CD71 Early Erythroid |
| ERMP1 | CD56 NK Cells |
| ERN1 | Liver |
| ERO1LB | Pancreatic Islet |
| ESM1 | CD105 Endothelial |
| ESR1 | Uterus |
| ETFB | Liver |
| ETNK1 | Colon |
| ETNK2 | Liver |
| ETV3 | Superior Cervical Ganglion |
| ETV4 | Colorectal adenocarcinoma |
| EVPL | Tongue |

FIG. 18AS

| | |
|---|---|
| EXOSC1 | Trigeminal Ganglion |
| EXOSC2 | X721 B lymphoblasts |
| EXOSC4 | Testis |
| EXOSC5 | X721 B lymphoblasts |
| EXPH5 | Placenta |
| EXT2 | Smooth Muscle |
| EXTL3 | Subthalamic Nucleus |
| EYA3 | Cardiac Myocytes |
| EYA4 | Skin |
| F10 | Liver |
| F11 | Pancreas |
| F12 | Liver |
| F13B | Fetal liver |
| F2R | Cardiac Myocytes |
| F2RL1 | Colon |
| FAAH | pineal night |
| FABP6 | small intestine |
| FABP7 | Fetal brain |
| FADS1 | Adipocyte |
| FAH | Liver |
| FAIM | Colorectal adenocarcinoma |
| FAM105A | BDCA4 Dentritic Cells |
| FAM106A | Atrioventricular Node |
| FAM108B1 | Whole Brain |

FIG. 18AT

| | |
|---|---|
| FAM110B | Trigeminal Ganglion |
| FAM118A | CD33 Myeloid |
| FAM119B | Uterus Corpus |
| FAM120C | Ovary |
| FAM125B | Spinal Cord |
| FAM127B | Thyroid |
| FAM135A | Appendix |
| FAM149A | pineal day |
| FAM48A | Testis Intersitial |
| FAM50B | Whole Brain |
| FAM55D | Colon |
| FAM5C | Amygdala |
| FAM63A | Whole Blood |
| FAM86A | Pituitary |
| FAM86B1 | Skeletal Muscle |
| FAM86C | Leukemia promyelocytic HL62 |
| FANCE | Lymphoma burkitts Daudi |
| FANCG | Leukemia lymphoblastic MOLT 14 |
| FARP2 | Testis |
| FARS2 | Heart |
| FAS | Whole Blood |
| FASLG | CD56 NK Cells |
| FASTK | Heart |

FIG. 18AU

| | |
|---|---|
| FASTKD2 | X721 B lymphoblasts |
| FAT4 | Fetal brain |
| FBLN2 | Adipocyte |
| FBN2 | Placenta |
| FBP1 | Liver |
| FBP2 | Skeletal Muscle |
| FBXL12 | Thymus |
| FBXL15 | Whole Brain |
| FBXL4 | CD71 Early Erythroid |
| FBXL6 | Pancreas |
| FBXL8 | X721 B lymphoblasts |
| FBXO17 | Leukemia chronic Myelogenous K573 |
| FBXO38 | CD8 T cells |
| FBXO4 | Trigeminal Ganglion |
| FBXO46 | X721 B lymphoblasts |
| FCGR2A | Whole Blood |
| FCGR2B | Placenta |
| FCHO1 | Lymphoma burkitts Raji |
| FCN2 | Liver |
| FCRL2 | CD19 Bcells neg. sel. |
| FECH | CD71 Early Erythroid |
| FEM1B | Testis Intersitial |
| FEM1C | Cerebellum |

FIG. 18AV

| | |
|---|---|
| FER1L4 | Trigeminal Ganglion |
| FETUB | Liver |
| FEZF2 | Amygdala |
| FFAR2 | Whole Blood |
| FFAR3 | Temporal Lobe |
| FGD1 | Fetal brain |
| FGD2 | CD33 Myeloid |
| FGF12 | Occipital Lobe |
| FGF14 | Cerebellum |
| FGF17 | Cingulate Cortex |
| FGF2 | Smooth Muscle |
| FGF22 | Ovary |
| FGF23 | Superior Cervical Ganglion |
| FGF3 | Colorectal adenocarcinoma |
| FGF4 | Olfactory Bulb |
| FGF5 | Superior Cervical Ganglion |
| FGF8 | Superior Cervical Ganglion |
| FGF9 | Cerebellum Peduncles |
| FGFR1OP | Testis Intersitial |
| FGFR4 | Liver |
| FGL1 | Fetal liver |
| FGL2 | CD14 Monocytes |
| FHIT | CD4 T cells |
| FHL3 | Skeletal Muscle |

FIG. 18AW

| | |
|---|---|
| FHL5 | Testis Intersitial |
| FILIP1L | Uterus |
| FKBP10 | Smooth Muscle |
| FKBP14 | Smooth Muscle |
| FKBP6 | Testis |
| FKBPL | CD105 Endothelial |
| FKRP | Superior Cervical Ganglion |
| FLG | Skin |
| FLJ20712 | Temporal Lobe |
| FLNC | Skeletal Muscle |
| FLOT2 | Whole Blood |
| FLT1 | Superior Cervical Ganglion |
| FLT4 | Placenta |
| FMO2 | Lung |
| FMO3 | Liver |
| FMO6P | Appendix |
| FN3K | Superior Cervical Ganglion |
| FNBP1L | Fetal brain |
| FNDC8 | Testis Intersitial |
| FOLH1 | Prostate |
| FOSL1 | Colorectal adenocarcinoma |
| FOXA1 | Prostate |
| FOXA2 | Pancreatic Islet |
| FOXB1 | Superior Cervical Ganglion |

FIG. 18AX

| | |
|---|---|
| FOXC1 | Salivary gland |
| FOXC2 | Superior Cervical Ganglion |
| FOXD3 | Superior Cervical Ganglion |
| FOXD4 | Globus Pallidus |
| FOXE1 | Thyroid |
| FOXE3 | Superior Cervical Ganglion |
| FOXK2 | Adrenal Cortex |
| FOXL1 | Liver |
| FOXN1 | Superior Cervical Ganglion |
| FOXN2 | Appendix |
| FOXP3 | Adrenal Cortex |
| FPGS | Ovary |
| FPGT | pineal day |
| FPR2 | Whole Blood |
| FPR3 | Superior Cervical Ganglion |
| FRAT1 | Whole Blood |
| FRAT2 | Whole Blood |
| FRK | Superior Cervical Ganglion |
| FRMD8 | Superior Cervical Ganglion |
| FRS2 | Pituitary |
| FRS3 | Testis |
| FRZB | retina |
| FSHB | Pituitary |
| FSHR | Superior Cervical Ganglion |

FIG. 18AY

| | |
|---|---|
| FST | Bronchial Epithelial Cells |
| FSTL3 | Placenta |
| FSTL4 | Appendix |
| FTCD | Liver |
| FTSJ1 | Bronchial Epithelial Cells |
| FXC1 | Superior Cervical Ganglion |
| FXN | CD105 Endothelial |
| FXYD2 | Kidney |
| FYCO1 | Tongue |
| FZD4 | Adipocyte |
| FZD5 | Colon |
| FZD7 | Cerebellum |
| FZD8 | Superior Cervical Ganglion |
| FZD9 | Appendix |
| FZR1 | CD71 Early Erythroid |
| G6PC | Liver |
| G6PC2 | Superior Cervical Ganglion |
| GAB1 | Superior Cervical Ganglion |
| GABRA4 | Caudate nucleus |
| GABRA5 | Amygdala |
| GABRB2 | Skin |
| GABRE | Placenta |
| GABRG3 | Subthalamic Nucleus |
| GABRP | Tonsil |

FIG. 18AZ

| | |
|---|---|
| GABRQ | Skeletal Muscle |
| GAD2 | Caudate nucleus |
| GADD45G | Placenta |
| GADD45GIP1 | Heart |
| GAL3ST1 | Spinal Cord |
| GALK1 | Liver |
| GALK2 | Leukemia chronic Myelogenous K574 |
| GALNS | CD33 Myeloid |
| GALNT12 | Colon |
| GALNT14 | Kidney |
| GALNT4 | CD71 Early Erythroid |
| GALNT6 | CD71 Early Erythroid |
| GALNT8 | Trigeminal Ganglion |
| GALR2 | Superior Cervical Ganglion |
| GALT | Liver |
| GAMT | Liver |
| GAPDHS | Testis Intersitial |
| GAPVD1 | CD71 Early Erythroid |
| GARNL3 | Appendix |
| GAST | Cerebellum |
| GATA4 | Heart |
| GATAD1 | Leukemia chronic Myelogenous K575 |
| GATC | Superior Cervical Ganglion |

FIG. 18AAA

| Gene | Tissue |
|---|---|
| GBA | Placenta |
| GBX1 | Bone marrow |
| GCAT | Liver |
| GCDH | Liver |
| GCGR | Liver |
| GCHFR | Liver |
| GCKR | Liver |
| GCLC | CD71 Early Erythroid |
| GCLM | CD71 Early Erythroid |
| GCM1 | Placenta |
| GCM2 | Skeletal Muscle |
| GCNT1 | CD19 Bcells neg. sel. |
| GCNT2 | CD71 Early Erythroid |
| GDAP1L1 | Fetal brain |
| GDF11 | retina |
| GDF15 | Placenta |
| GDF2 | Subthalamic Nucleus |
| GDF5 | Fetal liver |
| GDF9 | Testis Leydig Cell |
| GDPD3 | Colon |
| GEM | Uterus Corpus |
| GEMIN4 | Testis Intersitial |
| GEMIN8 | Skeletal Muscle |
| GFOD2 | Superior Cervical Ganglion |

FIG. 18AAB

| | |
|---|---|
| GFRA3 | Liver |
| GFRA4 | Pons |
| GGTLC1 | Lung |
| GH2 | Placenta |
| GHRHR | Pituitary |
| GHSR | Superior Cervical Ganglion |
| GIF | Superior Cervical Ganglion |
| GIMAP4 | Whole Blood |
| GINS4 | X721 B lymphoblasts |
| GIP | small intestine |
| GIPC2 | small intestine |
| GJA3 | Superior Cervical Ganglion |
| GJA4 | Lung |
| GJA5 | Superior Cervical Ganglion |
| GJA8 | Skeletal Muscle |
| GJB1 | Liver |
| GJB3 | Bronchial Epithelial Cells |
| GJB5 | Bronchial Epithelial Cells |
| GJC1 | Superior Cervical Ganglion |
| GJC2 | Spinal Cord |
| GK | Whole Blood |
| GK2 | Testis Intersitial |
| GK3P | Testis Germ Cell |
| GKN1 | small intestine |

FIG. 18AAC

| | |
|---|---|
| GLE1 | Testis Intersitial |
| GLI1 | Atrioventricular Node |
| GLMN | Skeletal Muscle |
| GLP2R | Superior Cervical Ganglion |
| GLRA1 | Superior Cervical Ganglion |
| GLRA2 | Uterus Corpus |
| GLS2 | Liver |
| GLT8D2 | Smooth Muscle |
| GLTP | Tonsil |
| GLTPD1 | Heart |
| GMDS | Colon |
| GMEB1 | CD56 NK Cells |
| GML | Trigeminal Ganglion |
| GNA13 | BDCA4 Dentritic Cells |
| GNA14 | Superior Cervical Ganglion |
| GNAT1 | retina |
| GNAZ | Fetal brain |
| GNB1L | Leukemia chronic Myelogenous K576 |
| GNG4 | Superior Cervical Ganglion |
| GNLY | CD56 NK Cells |
| GNRHR | Pituitary |
| GOLT1B | Smooth Muscle |
| GON4L | Leukemia chronic Myelogenous K577 |

FIG. 18AAD

| | |
|---|---|
| GP5 | Trigeminal Ganglion |
| GP6 | Superior Cervical Ganglion |
| GP9 | Whole Blood |
| GPATCH1 | CD8 T cells |
| GPATCH2 | Testis Seminiferous Tubule |
| GPATCH3 | CD14 Monocytes |
| GPATCH4 | Atrioventricular Node |
| GPATCH8 | CD56 NK Cells |
| GPC4 | Pituitary |
| GPC5 | pineal day |
| GPD1 | Adipocyte |
| GPI | CD71 Early Erythroid |
| GPKOW | CD71 Early Erythroid |
| GPR124 | retina |
| GPR137 | Testis |
| GPR143 | retina |
| GPR153 | Fetal brain |
| GPR157 | Globus Pallidus |
| GPR161 | Uterus |
| GPR17 | Whole Brain |
| GPR172B | Placenta |
| GPR176 | Smooth Muscle |
| GPR18 | CD19 Bcells neg. sel. |
| GPR182 | Superior Cervical Ganglion |

FIG. 18AAE

| | |
|---|---|
| GPR20 | Trigeminal Ganglion |
| GPR21 | Globus Pallidus |
| GPR31 | Superior Cervical Ganglion |
| GPR32 | Superior Cervical Ganglion |
| GPR35 | Pancreas |
| GPR37L1 | Amygdala |
| GPR39 | Superior Cervical Ganglion |
| GPR4 | Lung |
| GPR44 | Thymus |
| GPR50 | Superior Cervical Ganglion |
| GPR52 | Superior Cervical Ganglion |
| GPR6 | Caudate nucleus |
| GPR64 | Testis Leydig Cell |
| GPR65 | CD56 NK Cells |
| GPR68 | Skeletal Muscle |
| GPR87 | Bronchial Epithelial Cells |
| GPR98 | Medulla Oblongata |
| GPRIN2 | Superior Cervical Ganglion |
| GPT | Liver |
| GPX5 | Testis Leydig Cell |
| GRAMD1C | Appendix |
| GRB7 | Liver |
| GREM1 | Smooth Muscle |
| GRID2 | Superior Cervical Ganglion |

FIG. 18AAF

| | |
|---|---|
| GRIK3 | Superior Cervical Ganglion |
| GRIK4 | Olfactory Bulb |
| GRIN2A | Subthalamic Nucleus |
| GRIN2B | Skeletal Muscle |
| GRIN2C | Thyroid |
| GRIN2D | Superior Cervical Ganglion |
| GRIP1 | Superior Cervical Ganglion |
| GRIP2 | CD48 |
| GRK1 | Superior Cervical Ganglion |
| GRK4 | Testis |
| GRM1 | Cerebellum |
| GRM2 | Heart |
| GRM4 | Cerebellum Peduncles |
| GRRP1 | Globus Pallidus |
| GRTP1 | Superior Cervical Ganglion |
| GSR | X721 B lymphoblasts |
| GSTCD | Atrioventricular Node |
| GSTM1 | Liver |
| GSTM2 | Liver |
| GSTM4 | small intestine |
| GSTT2 | Whole Brain |
| GSTTP1 | Testis Interstitial |
| GSTZ1 | Liver |
| GTF2IRD1 | Colorectal adenocarcinoma |

FIG. 18AAG

| | |
|---|---|
| GTF3C5 | Heart |
| GTPBP1 | CD71 Early Erythroid |
| GUCY1A2 | Superior Cervical Ganglion |
| GUCY1B2 | Superior Cervical Ganglion |
| GUCY2C | Colon |
| GUCY2D | BDCA4 Dentritic Cells |
| GUF1 | Superior Cervical Ganglion |
| GULP1 | Placenta |
| GYG2 | Adipocyte |
| GYPE | CD71 Early Erythroid |
| GYS1 | Heart |
| GZMK | CD8 T cells |
| H2AFB1 | Testis |
| HAAO | Liver |
| HAL | Fetal liver |
| HAMP | Liver |
| HAO1 | Liver |
| HAO2 | Kidney |
| HAPLN1 | Cardiac Myocytes |
| HAPLN2 | Spinal Cord |
| HAS2 | Skeletal Muscle |
| HBE1 | Leukemia chronic Myelogenous K578 |
| HBQ1 | CD71 Early Erythroid |

FIG. 18AAH

| | |
|---|---|
| HBS1L | CD71 Early Erythroid |
| HBXIP | Kidney |
| HCCS | CD71 Early Erythroid |
| HCFC2 | Testis Intersitial |
| HCG4 | Superior Cervical Ganglion |
| HCG9 | Liver |
| HCN4 | Testis Leydig Cell |
| HCRT | Hypothalamus |
| HCRTR1 | Bone marrow |
| HCRTR2 | Atrioventricular Node |
| HDAC11 | Testis |
| HDGF | CD71 Early Erythroid |
| HEATR6 | Atrioventricular Node |
| HECTD3 | CD71 Early Erythroid |
| HECW1 | Atrioventricular Node |
| HEPH | Leukemia chronic Myelogenous K579 |
| HEXIM1 | CD71 Early Erythroid |
| HEY2 | retina |
| HGC6.3 | Skeletal Muscle |
| HGF | Smooth Muscle |
| HGFAC | Liver |
| HHAT | BDCA4 Dentritic Cells |
| HHIPL2 | Testis Intersitial |

FIG. 18AAI

| | |
|---|---|
| HHLA1 | Adrenal gland |
| HHLA3 | Liver |
| HIC1 | Superior Cervical Ganglion |
| HIC2 | Leukemia chronic Myelogenous K580 |
| HIF3A | Superior Cervical Ganglion |
| HIGD1B | Lung |
| HIP1R | CD19 Bcells neg. sel. |
| HIPK3 | CD33 Myeloid |
| HIST1H1E | Leukemia chronic Myelogenous K581 |
| HIST1H1T | Dorsal Root Ganglion |
| HIST1H2AB | CD19 Bcells neg. sel. |
| HIST1H2BC | Leukemia chronic Myelogenous K582 |
| HIST1H2BG | CD8 T cells |
| HIST1H2BJ | Ciliary Ganglion |
| HIST1H2BM | Superior Cervical Ganglion |
| HIST1H2BN | small intestine |
| HIST1H3F | Uterus Corpus |
| HIST1H3I | Cardiac Myocytes |
| HIST1H3J | Atrioventricular Node |
| HIST1H4A | CD71 Early Erythroid |
| HIST1H4E | Superior Cervical Ganglion |
| HIST1H4G | Skeletal Muscle |

FIG. 18AAJ

| | |
|---|---|
| HIST3H2A | Leukemia chronic Myelogenous K583 |
| HIVEP2 | Fetal brain |
| HKDC1 | pineal night |
| HLA-DOB | CD19 Bcells neg. sel. |
| HLCS | Thyroid |
| HMBS | CD71 Early Erythroid |
| HMGA2 | Bronchial Epithelial Cells |
| HMGB3 | Placenta |
| HMGCL | Liver |
| HMGCS2 | Liver |
| HMHB1 | Skeletal Muscle |
| HNF4G | Ovary |
| HNRNPA2B1 | Liver |
| HOOK1 | Testis Interstitial |
| HOOK2 | Thyroid |
| HOXA1 | Leukemia chronic Myelogenous K584 |
| HOXA10 | Uterus |
| HOXA3 | Superior Cervical Ganglion |
| HOXA6 | Kidney |
| HOXA7 | Adrenal Cortex |
| HOXA9 | Colorectal adenocarcinoma |
| HOXB1 | Cingulate Cortex |
| HOXB13 | Prostate |

FIG. 18AAK

| | |
|---|---|
| HOXB5 | Colorectal adenocarcinoma |
| HOXB6 | Colorectal adenocarcinoma |
| HOXB7 | Colorectal adenocarcinoma |
| HOXB8 | Superior Cervical Ganglion |
| HOXC11 | Superior Cervical Ganglion |
| HOXC5 | Liver |
| HOXC8 | Skeletal Muscle |
| HOXD1 | Trigeminal Ganglion |
| HOXD10 | Uterus |
| HOXD11 | Appendix |
| HOXD12 | Skeletal Muscle |
| HOXD3 | Uterus |
| HOXD4 | Uterus |
| HOXD9 | Uterus |
| HP | Liver |
| HPGD | Placenta |
| HPN | Liver |
| HPR | Liver |
| HPS1 | CD71 Early Erythroid |
| HPS4 | CD105 Endothelial |
| HR | pineal day |
| HRC | Heart |
| HRG | Liver |
| HRK | CD19 Bcells neg. sel. |

FIG. 18AAL

| | |
|---|---|
| HS1BP3 | CD14 Monocytes |
| HS3ST1 | Ovary |
| HS3ST3B1 | Heart |
| HS6ST1 | Superior Cervical Ganglion |
| HSD11B1 | Liver |
| HSD17B1 | Placenta |
| HSD17B2 | Placenta |
| HSD17B6 | Liver |
| HSD17B8 | Liver |
| HSD3B1 | Placenta |
| HSF1 | Heart |
| HSFX1 | Cardiac Myocytes |
| HSP90AA1 | Heart |
| HSPA1L | Testis Intersitial |
| HSPA4L | Testis Intersitial |
| HSPA6 | Whole Blood |
| HSPB2 | Heart |
| HSPB3 | Heart |
| HSPC159 | Superior Cervical Ganglion |
| HTN1 | Salivary gland |
| HTR1A | Liver |
| HTR1B | Heart |
| HTR1D | Skeletal Muscle |
| HTR1E | pineal night |

FIG. 18AAM

| | |
|---|---|
| HTR1F | Appendix |
| HTR2A | Prefrontal Cortex |
| HTR2C | Caudate nucleus |
| HTR3A | Dorsal Root Ganglion |
| HTR3B | Skin |
| HTR5A | Skeletal Muscle |
| HTR7 | Cardiac Myocytes |
| HTRA2 | CD71 Early Erythroid |
| HUS1 | Superior Cervical Ganglion |
| HYAL2 | Lung |
| HYAL4 | Superior Cervical Ganglion |
| ICAM4 | CD71 Early Erythroid |
| ICAM5 | Amygdala |
| ICOSLG | Skeletal Muscle |
| IDE | Testis Germ Cell |
| IDH3G | Heart |
| IER3IP1 | Smooth Muscle |
| IFI44 | CD33 Myeloid |
| IFIT1 | Whole Blood |
| IFIT2 | Whole Blood |
| IFIT5 | Whole Blood |
| IFNA21 | Testis Seminiferous Tubule |
| IFNA4 | Dorsal Root Ganglion |
| IFNA5 | Superior Cervical Ganglion |

FIG. 18AAN

| | |
|---|---|
| IFNA6 | Superior Cervical Ganglion |
| IFNAR1 | Superior Cervical Ganglion |
| IFNG | CD56 NK Cells |
| IFNW1 | Ovary |
| IFT140 | Thyroid |
| IFT52 | CD71 Early Erythroid |
| IFT81 | Testis Leydig Cell |
| IGF1R | Prostate |
| IGF2AS | Subthalamic Nucleus |
| IGFALS | Liver |
| IGLL1 | CD49 |
| IGLV6-57 | Lymph node |
| IHH | Heart |
| IKZF3 | CD8 T cells |
| IKZF5 | CD8 T cells |
| IL10 | Atrioventricular Node |
| IL11 | Smooth Muscle |
| IL11RA | CD4 T cells |
| IL12A | Uterus Corpus |
| IL12RB2 | CD56 NK Cells |
| IL13 | Testis Intersitial |
| IL13RA2 | Testis Intersitial |
| IL15 | pineal night |
| IL17B | Olfactory Bulb |

FIG. 18AAO

| | |
|---|---|
| IL17RA | CD33 Myeloid |
| IL17RB | Kidney |
| IL18RAP | CD56 NK Cells |
| IL19 | Trachea |
| IL1B | Smooth Muscle |
| IL1F6 | Superior Cervical Ganglion |
| IL1F7 | Skeletal Muscle |
| IL1F9 | Superior Cervical Ganglion |
| IL1RAPL1 | Prefrontal Cortex |
| IL1RAPL2 | Superior Cervical Ganglion |
| IL1RL1 | Placenta |
| IL2 | Heart |
| IL20RA | Ciliary Ganglion |
| IL21 | Superior Cervical Ganglion |
| IL22 | Superior Cervical Ganglion |
| IL24 | Smooth Muscle |
| IL25 | Pons |
| IL2RA | Superior Cervical Ganglion |
| IL2RB | CD56 NK Cells |
| IL3RA | BDCA4 Dentritic Cells |
| IL4 | Atrioventricular Node |
| IL4R | CD19 Bcells neg. sel. |
| IL5 | Atrioventricular Node |
| IL5RA | Ciliary Ganglion |

FIG. 18AAP

| | |
|---|---|
| IL9 | Leukemia promyelocytic HL63 |
| IL9R | Testis Intersitial |
| ILVBL | Heart |
| IMPG1 | retina |
| INCENP | Leukemia lymphoblastic MOLT 15 |
| INE1 | Atrioventricular Node |
| ING1 | CD19 Bcells neg. sel. |
| INHA | Testis Germ Cell |
| INHBA | Placenta |
| INHBE | Liver |
| INPP5B | X721 B lymphoblasts |
| INSIG2 | X721 B lymphoblasts |
| INSL4 | Placenta |
| INSL6 | Superior Cervical Ganglion |
| INSRR | Superior Cervical Ganglion |
| INTS12 | BDCA4 Dentritic Cells |
| INTS5 | Liver |
| IPO8 | CD4 T cells |
| IQCB1 | Lymphoma burkitts Daudi |
| IRF2 | Whole Blood |
| IRF6 | Bronchial Epithelial Cells |
| IRS4 | Skeletal Muscle |
| IRX4 | Skin |

FIG. 18AAQ

| | |
|---|---|
| IRX5 | Lung |
| ISCA1 | CD71 Early Erythroid |
| ISL1 | Pancreatic Islet |
| ISOC2 | Liver |
| ISYNA1 | Testis Germ Cell |
| ITCH | Testis Intersitial |
| ITFG2 | CD4 T cells |
| ITGA2 | Bronchial Epithelial Cells |
| ITGA3 | Bronchial Epithelial Cells |
| ITGA9 | Testis Seminiferous Tubule |
| ITGB1BP3 | Heart |
| ITGB5 | Colorectal adenocarcinoma |
| ITGB6 | Bronchial Epithelial Cells |
| ITGB8 | Appendix |
| ITGBL1 | Adipocyte |
| ITIH4 | Liver |
| ITIH5 | Placenta |
| ITM2B | X721 B lymphoblasts |
| ITPKA | Whole Brain |
| ITSN1 | CD71 Early Erythroid |
| IVL | Tongue |
| JAKMIP2 | Prefrontal Cortex |
| JMJD5 | Liver |
| JPH2 | Superior Cervical Ganglion |

FIG. 18AAR

| | |
|---|---|
| KAL1 | Spinal Cord |
| KAZALD1 | Skeletal Muscle |
| KCNA1 | Superior Cervical Ganglion |
| KCNA10 | Skeletal Muscle |
| KCNA2 | Skeletal Muscle |
| KCNA3 | Dorsal Root Ganglion |
| KCNA4 | Superior Cervical Ganglion |
| KCNAB1 | Caudate nucleus |
| KCNAB3 | Subthalamic Nucleus |
| KCNB2 | Trigeminal Ganglion |
| KCNC3 | Lymphoma burkitts Daudi |
| KCND1 | Thyroid |
| KCND2 | Cerebellum Peduncles |
| KCNE1 | Pancreas |
| KCNE1L | Superior Cervical Ganglion |
| KCNE4 | Uterus Corpus |
| KCNG1 | CD19 Bcells neg. sel. |
| KCNG2 | Superior Cervical Ganglion |
| KCNH1 | Appendix |
| KCNH2 | CD105 Endothelial |
| KCNH4 | Superior Cervical Ganglion |
| KCNJ1 | Kidney |
| KCNJ10 | Occipital Lobe |
| KCNJ13 | Superior Cervical Ganglion |

FIG. 18AAS

| | |
|---|---|
| KCNJ14 | Appendix |
| KCNJ2 | Whole Blood |
| KCNJ3 | Superior Cervical Ganglion |
| KCNJ6 | Cingulate Cortex |
| KCNJ9 | Cerebellum |
| KCNK10 | BDCA4 Dentritic Cells |
| KCNK12 | Olfactory Bulb |
| KCNK2 | Atrioventricular Node |
| KCNK7 | Superior Cervical Ganglion |
| KCNMA1 | Uterus |
| KCNMB3 | Testis Intersitial |
| KCNN2 | Adrenal gland |
| KCNN4 | CD71 Early Erythroid |
| KCNS3 | Lung |
| KCNV2 | retina |
| KCTD14 | Adrenal gland |
| KCTD15 | Kidney |
| KCTD17 | pineal day |
| KCTD20 | CD71 Early Erythroid |
| KCTD5 | BDCA4 Dentritic Cells |
| KCTD7 | pineal night |
| KDELC1 | Cardiac Myocytes |
| KDELR3 | Smooth Muscle |
| KDSR | Olfactory Bulb |

FIG. 18AAT

| KIAA0040 | CD19 Bcells neg. sel. |
|---|---|
| KIAA0087 | Trigeminal Ganglion |
| KIAA0090 | Placenta |
| KIAA0100 | BDCA4 Dentritic Cells |
| KIAA0141 | Superior Cervical Ganglion |
| KIAA0196 | CD14 Monocytes |
| KIAA0319 | Fetal brain |
| KIAA0556 | pineal day |
| KIAA0586 | Testis Intersitial |
| KIAA1024 | Adrenal Cortex |
| KIAA1199 | Smooth Muscle |
| KIAA1310 | Uterus Corpus |
| KIAA1324 | Prostate |
| KIAA1539 | CD71 Early Erythroid |
| KIAA1609 | Bronchial Epithelial Cells |
| KIAA1751 | Superior Cervical Ganglion |
| KIF17 | Cingulate Cortex |
| KIF18A | X721 B lymphoblasts |
| KIF18B | Leukemia lymphoblastic MOLT 16 |
| KIF21B | Fetal brain |
| KIF22 | CD71 Early Erythroid |
| KIF25 | Superior Cervical Ganglion |
| KIF26B | Ciliary Ganglion |

FIG. 18AAU

| | |
|---|---|
| KIF5A | Whole Brain |
| KIFC1 | CD71 Early Erythroid |
| KIR2DL2 | CD56 NK Cells |
| KIR2DL3 | CD56 NK Cells |
| KIR2DL4 | CD56 NK Cells |
| KIR2DS4 | CD56 NK Cells |
| KIR3DL1 | CD56 NK Cells |
| KIR3DL2 | CD56 NK Cells |
| KIRREL | Superior Cervical Ganglion |
| KISS1 | Placenta |
| KL | Kidney |
| KLF12 | CD8 T cells |
| KLF15 | Liver |
| KLF3 | CD71 Early Erythroid |
| KLF8 | Spinal Cord |
| KLHDC4 | CD56 NK Cells |
| KLHL11 | Temporal Lobe |
| KLHL12 | Testis Intersitial |
| KLHL18 | CD105 Endothelial |
| KLHL21 | Heart |
| KLHL25 | Atrioventricular Node |
| KLHL26 | Whole Brain |
| KLHL29 | Uterus Corpus |
| KLHL3 | Cerebellum |

FIG. 18AAV

| | |
|---|---|
| KLHL4 | Fetal brain |
| KLK10 | Tongue |
| KLK12 | Tongue |
| KLK13 | Tongue |
| KLK14 | Atrioventricular Node |
| KLK15 | Pancreas |
| KLK2 | Prostate |
| KLK3 | Prostate |
| KLK5 | Testis Intersitial |
| KLK7 | Pancreas |
| KLK8 | Tongue |
| KLRC3 | CD56 NK Cells |
| KLRF1 | CD56 NK Cells |
| KLRK1 | CD8 T cells |
| KNTC1 | Leukemia lymphoblastic MOLT 17 |
| KPNA4 | X721 B lymphoblasts |
| KPTN | Cerebellum |
| KRT1 | Skin |
| KRT10 | Skin |
| KRT12 | Liver |
| KRT17 | Tongue |
| KRT2 | Skin |
| KRT23 | Colorectal adenocarcinoma |

FIG. 18AAW

| | |
|---|---|
| KRT3 | Superior Cervical Ganglion |
| KRT33A | Superior Cervical Ganglion |
| KRT34 | Skin |
| KRT36 | Superior Cervical Ganglion |
| KRT38 | Atrioventricular Node |
| KRT6B | Tongue |
| KRT84 | Superior Cervical Ganglion |
| KRT86 | Placenta |
| KRT9 | Superior Cervical Ganglion |
| KRTAP1-1 | Superior Cervical Ganglion |
| KRTAP1-3 | Ciliary Ganglion |
| KRTAP4-7 | Superior Cervical Ganglion |
| KRTAP5-9 | Superior Cervical Ganglion |
| L1TD1 | Dorsal Root Ganglion |
| L2HGDH | Superior Cervical Ganglion |
| LACTB2 | small intestine |
| LAD1 | Bronchial Epithelial Cells |
| LAIR1 | BDCA4 Dentritic Cells |
| LAIR2 | CD56 NK Cells |
| LALBA | Ovary |
| LAMA2 | Adipocyte |
| LAMA3 | Bronchial Epithelial Cells |
| LAMA4 | Smooth Muscle |
| LAMA5 | Colorectal adenocarcinoma |

FIG. 18AAX

| | |
|---|---|
| LAMB3 | Bronchial Epithelial Cells |
| LAMC2 | Bronchial Epithelial Cells |
| LANCL2 | Testis |
| LAT | CD4 T cells |
| LAX1 | CD4 T cells |
| LCAT | Liver |
| LCMT2 | CD105 Endothelial |
| LCT | Trigeminal Ganglion |
| LDB1 | CD105 Endothelial |
| LDB3 | Skeletal Muscle |
| LDHAL6B | Testis |
| LDHB | Liver |
| LDLR | Adrenal Cortex |
| LECT1 | CD105 Endothelial |
| LEF1 | Thymus |
| LEFTY1 | Colon |
| LEFTY2 | Uterus Corpus |
| LENEP | Salivary gland |
| LEP | Placenta |
| LETM1 | Thymus |
| LFNG | Liver |
| LGALS13 | Placenta |
| LGALS14 | Placenta |
| LGR4 | Colon |

FIG. 18AAY

| | |
|---|---|
| LHB | Pituitary |
| LHCGR | Superior Cervical Ganglion |
| LHX2 | Fetal brain |
| LHX5 | Superior Cervical Ganglion |
| LHX6 | Fetal brain |
| LIG3 | Leukemia lymphoblastic MOLT 18 |
| LILRB4 | BDCA4 Dentritic Cells |
| LILRB5 | Skeletal Muscle |
| LIM2 | CD56 NK Cells |
| LIMS2 | Uterus |
| LIPF | small intestine |
| LIPG | Thyroid |
| LIPT1 | CD8 T cells |
| LMCD1 | Skeletal Muscle |
| LMF1 | Liver |
| LMO1 | retina |
| LMTK2 | Superior Cervical Ganglion |
| LMX1B | Superior Cervical Ganglion |
| LOC1720 | Superior Cervical Ganglion |
| LOC388796 | Lymphoma burkitts Raji |
| LOC390561 | Uterus Corpus |
| LOC390940 | Superior Cervical Ganglion |
| LOC399904 | Temporal Lobe |

FIG. 18AAZ

| | |
|---|---|
| LOC441204 | Appendix |
| LOC442421 | Superior Cervical Ganglion |
| LOC51145 | Appendix |
| LOC93432 | Ovary |
| LOH3CR2A | Appendix |
| LOR | Skin |
| LPAL2 | Uterus Corpus |
| LPAR3 | Testis Germ Cell |
| LPIN2 | CD71 Early Erythroid |
| LRAT | Pons |
| LRCH3 | CD8 T cells |
| LRDD | Pancreas |
| LRFN3 | Superior Cervical Ganglion |
| LRFN4 | Fetal brain |
| LRIT1 | Superior Cervical Ganglion |
| LRP1B | Amygdala |
| LRP2 | Thyroid |
| LRP5L | Superior Cervical Ganglion |
| LRRC16A | Testis Germ Cell |
| LRRC17 | Smooth Muscle |
| LRRC2 | Thyroid |
| LRRC20 | Skeletal Muscle |
| LRRC3 | Skeletal Muscle |
| LRRC31 | Colon |

FIG. 18AAAA

| | |
|---|---|
| LRRC32 | Lung |
| LRRC36 | Testis Intersitial |
| LRRC37A4 | Cerebellum |
| LRRK1 | Lymphoma burkitts Daudi |
| LST1 | Whole Blood |
| LST-3TM12 | Fetal liver |
| LTB4R | CD33 Myeloid |
| LTB4R2 | Temporal Lobe |
| LTBP4 | Thyroid |
| LTC4S | Lung |
| LTK | BDCA4 Dentritic Cells |
| LUC7L | Whole Blood |
| LY6D | Tongue |
| LY6E | Lung |
| LY6G5C | CD71 Early Erythroid |
| LY6G6D | Pancreas |
| LY6G6E | Ovary |
| LY6H | Amygdala |
| LY96 | Whole Blood |
| LYL1 | CD71 Early Erythroid |
| LYPD1 | Smooth Muscle |
| LYST | Whole Blood |
| LYVE1 | Fetal lung |
| LYZL6 | Testis Intersitial |

FIG. 18AAAB

| | |
|---|---|
| LZTFL1 | Leukemia lymphoblastic MOLT 19 |
| LZTS1 | Skeletal Muscle |
| MACROD1 | Heart |
| MAF | small intestine |
| MAFF | Placenta |
| MAFK | Superior Cervical Ganglion |
| MAGEA1 | X721 B lymphoblasts |
| MAGEA2 | Leukemia chronic Myelogenous K585 |
| MAGEA5 | X721 B lymphoblasts |
| MAGEA8 | Placenta |
| MAGEB1 | Testis Germ Cell |
| MAGEC1 | Leukemia chronic Myelogenous K586 |
| MAGEC2 | Skeletal Muscle |
| MAGED4 | Fetal brain |
| MAGEL2 | Hypothalamus |
| MAGI1 | Globus Pallidus |
| MAGIX | Superior Cervical Ganglion |
| MAGOHB | CD105 Endothelial |
| MALL | small intestine |
| MAML3 | Ovary |
| MAMLD1 | Testis Germ Cell |
| MAN1A2 | Placenta |

FIG. 18AAAC

| | |
|---|---|
| MAN1C1 | Placenta |
| MAN2C1 | CD8 T cells |
| MAP2K3 | CD71 Early Erythroid |
| MAP2K5 | Globus Pallidus |
| MAP2K7 | Atrioventricular Node |
| MAP3K12 | Cerebellum |
| MAP3K14 | CD19 Bcells neg. sel. |
| MAP3K6 | Lung |
| MAP4K2 | X721 B lymphoblasts |
| MAPK4 | Skeletal Muscle |
| MAPK7 | CD56 NK Cells |
| MAPKAP1 | X721 B lymphoblasts |
| MAPKAPK3 | Heart |
| MARK2 | Globus Pallidus |
| MARK3 | CD71 Early Erythroid |
| MAS1 | Appendix |
| MASP1 | Heart |
| MASP2 | Liver |
| MAST1 | Fetal brain |
| MATK | CD56 NK Cells |
| MATN1 | Trachea |
| MATN4 | Lymphoma burkitts Raji |
| MBNL3 | CD71 Early Erythroid |
| MBTPS1 | pineal night |

FIG. 18AAAD

| | |
|---|---|
| MBTPS2 | Dorsal Root Ganglion |
| MC2R | Adrenal Cortex |
| MC3R | Superior Cervical Ganglion |
| MC4R | Superior Cervical Ganglion |
| MCCC2 | X721 B lymphoblasts |
| MCF2 | pineal day |
| MCM10 | CD105 Endothelial |
| MCM9 | CD19 Bcells neg. sel. |
| MCOLN3 | Adrenal Cortex |
| MCPH1 | Thymus |
| MCTP1 | Caudate nucleus |
| MCTP2 | Whole Blood |
| ME1 | Adipocyte |
| MECR | Heart |
| MED1 | Thymus |
| MED15 | CD8 T cells |
| MED22 | CD19 Bcells neg. sel. |
| MED31 | Cerebellum |
| MED7 | Testis Intersitial |
| MEGF6 | Lung |
| MEGF8 | Skeletal Muscle |
| MEOX2 | Fetal lung |
| MEP1B | small intestine |
| MET | Bronchial Epithelial Cells |

FIG. 18AAAE

| | |
|---|---|
| METTL4 | CD8 T cells |
| METTL8 | CD19 Bcells neg. sel. |
| MEX3D | Subthalamic Nucleus |
| MFAP5 | Adipocyte |
| MFI2 | Uterus Corpus |
| MFN1 | Lymphoma burkitts Raji |
| MFSD7 | Ovary |
| MGA | CD8 T cells |
| MGAT4A | CD8 T cells |
| MGAT5 | Temporal Lobe |
| MGC29506 | Thymus |
| MGC4294 | Superior Cervical Ganglion |
| MGC5590 | Cardiac Myocytes |
| MGMT | Liver |
| MGST3 | Lymphoma burkitts Daudi |
| MIA2 | Superior Cervical Ganglion |
| MIA3 | BDCA4 Dentritic Cells |
| MICALL2 | Colorectal adenocarcinoma |
| MIER2 | Lung |
| MIPEP | Kidney |
| MITF | Uterus |
| MKS1 | Superior Cervical Ganglion |
| MLANA | retina |
| MLF1 | Testis Intersitial |

FIG. 18AAAF

| | |
|---|---|
| MLH3 | Whole Blood |
| MLL2 | Liver |
| MLLT1 | Superior Cervical Ganglion |
| MLLT10 | Dorsal Root Ganglion |
| MLLT3 | CD8 T cells |
| MLN | Liver |
| MLNR | Superior Cervical Ganglion |
| MMACHC | Liver |
| MME | Adipocyte |
| MMP10 | Uterus Corpus |
| MMP11 | Placenta |
| MMP12 | Tonsil |
| MMP15 | Thyroid |
| MMP24 | Cerebellum Peduncles |
| MMP26 | Skeletal Muscle |
| MMP28 | Lung |
| MMP3 | Smooth Muscle |
| MMP8 | Bone marrow |
| MMP9 | Bone marrow |
| MN1 | Fetal brain |
| MNDA | Whole Blood |
| MOBKL3 | Adrenal Cortex |
| MOCOS | Adrenal gland |
| MOCS3 | Atrioventricular Node |

FIG. 18AAAG

| | |
|---|---|
| MOGAT2 | Liver |
| MON1B | Prostate |
| MORC4 | Placenta |
| MORF4L2 | Heart |
| MORN1 | Cingulate Cortex |
| MOS | Superior Cervical Ganglion |
| MOSC2 | Kidney |
| MOSPD2 | CD33 Myeloid |
| MPL | Skeletal Muscle |
| MPP3 | Cerebellum |
| MPP5 | Placenta |
| MPP6 | Testis Germ Cell |
| MPPED1 | Fetal brain |
| MPPED2 | Thyroid |
| MPZL1 | Smooth Muscle |
| MPZL2 | Colorectal adenocarcinoma |
| MRAS | Heart |
| MREG | pineal day |
| MRPL17 | X721 B lymphoblasts |
| MRPL46 | X721 B lymphoblasts |
| MRPS18A | Heart |
| MRPS18C | Atrioventricular Node |
| MRS2 | X721 B lymphoblasts |
| MRTO4 | Leukemia promyelocytic |

FIG. 18AAAH

|  | HL64 |
|---|---|
| MS4A12 | Colon |
| MS4A2 | Ciliary Ganglion |
| MS4A4A | Placenta |
| MS4A5 | Testis Intersitial |
| MSC | X721 B lymphoblasts |
| MSH4 | Uterus Corpus |
| MSLN | Lung |
| MSRA | Kidney |
| MST1 | Liver |
| MST1R | Colorectal adenocarcinoma |
| MSX1 | Colorectal adenocarcinoma |
| MT4 | Lymphoma burkitts Raji |
| MTERFD1 | CD105 Endothelial |
| MTERFD2 | CD8 T cells |
| MTF1 | CD33 Myeloid |
| MTHFSD | Testis |
| MTMR10 | CD71 Early Erythroid |
| MTMR12 | CD71 Early Erythroid |
| MTMR3 | CD71 Early Erythroid |
| MTMR4 | Placenta |
| MTMR7 | Superior Cervical Ganglion |
| MTMR8 | Skeletal Muscle |
| MTNR1A | Superior Cervical Ganglion |

FIG. 18AAAI

| | |
|---|---|
| MTNR1B | Superior Cervical Ganglion |
| MTTP | small intestine |
| MUC1 | Lung |
| MUC13 | Pancreas |
| MUC16 | Trachea |
| MUC2 | Colon |
| MUC5B | Trachea |
| MUM1 | Testis |
| MUSK | Skeletal Muscle |
| MUTYH | Leukemia lymphoblastic MOLT 20 |
| MVD | Adipocyte |
| MXD1 | Whole Blood |
| MYBPC1 | Skeletal Muscle |
| MYBPC3 | Heart |
| MYBPH | Superior Cervical Ganglion |
| MYCN | Fetal brain |
| MYCT1 | Trigeminal Ganglion |
| MYF5 | Superior Cervical Ganglion |
| MYF6 | Skeletal Muscle |
| MYH1 | Skeletal Muscle |
| MYH13 | Skeletal Muscle |
| MYH15 | Appendix |
| MYH7B | Superior Cervical Ganglion |

FIG. 18AAAJ

| | |
|---|---|
| MYL7 | Heart |
| MYNN | Trigeminal Ganglion |
| MYO16 | Fetal brain |
| MYO1A | small intestine |
| MYO1B | Bronchial Epithelial Cells |
| MYO5A | Superior Cervical Ganglion |
| MYO5C | Salivary gland |
| MYO7B | Liver |
| MYOC | retina |
| MYST2 | Testis |
| MYT1 | pineal night |
| N4BP1 | Whole Blood |
| N6AMT1 | Trigeminal Ganglion |
| NAALAD2 | Pituitary |
| NAALADL1 | Liver |
| NAB2 | Cerebellum |
| NAPG | Superior Cervical Ganglion |
| NARF | CD71 Early Erythroid |
| NAT1 | Colon |
| NAT2 | Colon |
| NAT8 | Kidney |
| NAT8B | Kidney |
| NAV2 | Fetal brain |
| NAV3 | Fetal brain |

FIG. 18AAAK

| | |
|---|---|
| NBEA | Fetal brain |
| NBEAL2 | Lymphoma burkitts Raji |
| NCAM2 | Superior Cervical Ganglion |
| NCAPG2 | CD71 Early Erythroid |
| NCBP1 | X721 B lymphoblasts |
| NCLN | BDCA4 Dentritic Cells |
| NCOA2 | Whole Blood |
| NCR1 | CD56 NK Cells |
| NCR2 | Lymphoma burkitts Raji |
| NCR3 | CD56 NK Cells |
| NDP | Amygdala |
| NDUFA4L2 | Pancreas |
| NDUFB2 | Heart |
| NDUFB7 | Heart |
| NECAB2 | Caudate nucleus |
| NEIL3 | Leukemia lymphoblastic MOLT 21 |
| NEK11 | Uterus Corpus |
| NEK3 | Pancreas |
| NEK4 | Testis Germ Cell |
| NELF | Colorectal adenocarcinoma |
| NELL1 | Whole Brain |
| NES | Olfactory Bulb |
| NETO2 | Fetal brain |

FIG. 18AAAL

| | |
|---|---|
| NEU3 | Atrioventricular Node |
| NEUROD6 | Fetal brain |
| NEUROG3 | Superior Cervical Ganglion |
| NFATC1 | CD19 Bcells neg. sel. |
| NFATC3 | Thymus |
| NFE2 | CD71 Early Erythroid |
| NFE2L3 | Colorectal adenocarcinoma |
| NFKB2 | Lymphoma burkitts Raji |
| NFKBIB | Testis |
| NFKBIL2 | Atrioventricular Node |
| NFX1 | BDCA4 Dentritic Cells |
| NFYA | Cardiac Myocytes |
| NGB | CD71 Early Erythroid |
| NGF | Ciliary Ganglion |
| NGFR | Colorectal adenocarcinoma |
| NHLH2 | Hypothalamus |
| NINJ1 | Whole Blood |
| NIPSNAP3B | Superior Cervical Ganglion |
| NKAIN1 | Fetal brain |
| NKX2-2 | Spinal Cord |
| NKX2-5 | Heart |
| NKX2-8 | Superior Cervical Ganglion |
| NKX3-2 | Colon |
| NKX6-1 | Skeletal Muscle |

FIG. 18AAAM

| | |
|---|---|
| NLE1 | Lymphoma burkitts Raji |
| NMBR | Superior Cervical Ganglion |
| NMD3 | Bronchial Epithelial Cells |
| NME5 | Testis Intersitial |
| NMU | Leukemia chronic Myelogenous K587 |
| NMUR1 | CD56 NK Cells |
| NOC2L | Lymphoma burkitts Raji |
| NOC3L | X721 B lymphoblasts |
| NOC4L | Testis |
| NOL10 | Superior Cervical Ganglion |
| NOL3 | Heart |
| NOS1 | Uterus Corpus |
| NOS3 | Placenta |
| NOTCH1 | Leukemia lymphoblastic MOLT 22 |
| NOX1 | Colon |
| NOX3 | CD105 Endothelial |
| NOX4 | Kidney |
| NPAS2 | Smooth Muscle |
| NPAT | CD8 T cells |
| NPC1L1 | Fetal liver |
| NPFFR1 | Subthalamic Nucleus |
| NPHP4 | CD50 |
| NPHS2 | Kidney |

FIG. 18AAAN

| | |
|---|---|
| NPM3 | Bronchial Epithelial Cells |
| NPPA | Heart |
| NPPB | Heart |
| NPPC | Superior Cervical Ganglion |
| NPTXR | Skeletal Muscle |
| NPY | Prostate |
| NPY1R | Fetal brain |
| NPY2R | Superior Cervical Ganglion |
| NQO2 | Kidney |
| NR0B2 | Liver |
| NR1D1 | pineal day |
| NR1H2 | Lung |
| NR1H4 | Fetal liver |
| NR1I3 | Liver |
| NR2C1 | Superior Cervical Ganglion |
| NR2C2 | Testis Leydig Cell |
| NR2E1 | Amygdala |
| NR2E3 | retina |
| NR4A1 | Adrenal Cortex |
| NR4A2 | Adrenal Cortex |
| NR4A3 | Adrenal Cortex |
| NR5A1 | Globus Pallidus |
| NR6A1 | Testis |
| NRAP | Heart |

FIG. 18AAAO

| | |
|---|---|
| NRAS | BDCA4 Dentritic Cells |
| NRBF2 | Whole Blood |
| NRG2 | Superior Cervical Ganglion |
| NRIP2 | Olfactory Bulb |
| NRL | retina |
| NRP2 | Skeletal Muscle |
| NRTN | Superior Cervical Ganglion |
| NRXN3 | Cerebellum Peduncles |
| NSUN3 | CD71 Early Erythroid |
| NSUN6 | CD4 T cells |
| NT5DC3 | Fetal brain |
| NT5M | CD71 Early Erythroid |
| NTAN1 | CD71 Early Erythroid |
| NTHL1 | Liver |
| NTN1 | Superior Cervical Ganglion |
| NTNG1 | Uterus Corpus |
| NTSR1 | Colorectal adenocarcinoma |
| NUDT1 | CD71 Early Erythroid |
| NUDT15 | Colorectal adenocarcinoma |
| NUDT18 | CD19 Bcells neg. sel. |
| NUDT4 | CD71 Early Erythroid |
| NUDT6 | Leukemia lymphoblastic MOLT 23 |
| NUDT7 | Superior Cervical Ganglion |

FIG. 18AAAP

| | |
|---|---|
| NUFIP1 | CD105 Endothelial |
| NUMB | Whole Blood |
| NUP155 | Testis Interstitial |
| NUPL1 | Fetal brain |
| NUPL2 | Colorectal adenocarcinoma |
| NXPH3 | Cerebellum |
| OAS1 | CD14 Monocytes |
| OAS2 | Lymphoma burkitts Daudi |
| OAS3 | CD33 Myeloid |
| OASL | Whole Blood |
| OAZ3 | Testis Interstitial |
| OBFC2A | Uterus Corpus |
| OBSCN | Temporal Lobe |
| OCEL1 | CD14 Monocytes |
| OCLM | Superior Cervical Ganglion |
| OCLN | Skeletal Muscle |
| ODF1 | Testis Interstitial |
| ODZ4 | Fetal brain |
| OGFRL1 | Whole Blood |
| OLAH | Placenta |
| OLFM4 | small intestine |
| OLFML3 | Adipocyte |
| OLR1 | Placenta |
| OMD | Superior Cervical Ganglion |

FIG. 18AAAQ

| | |
|---|---|
| OMP | Superior Cervical Ganglion |
| ONECUT1 | Liver |
| OPA3 | Colorectal adenocarcinoma |
| OPLAH | Heart |
| OPN1LW | retina |
| OPN1SW | Superior Cervical Ganglion |
| OPRD1 | Thalamus |
| OPRL1 | Lymphoma burkitts Raji |
| OR10C1 | Superior Cervical Ganglion |
| OR10H1 | Trigeminal Ganglion |
| OR10H3 | Pons |
| OR10J1 | Superior Cervical Ganglion |
| OR11A1 | Superior Cervical Ganglion |
| OR1A1 | Superior Cervical Ganglion |
| OR2B2 | Superior Cervical Ganglion |
| OR2B6 | Superior Cervical Ganglion |
| OR2C1 | Superior Cervical Ganglion |
| OR2H1 | Skeletal Muscle |
| OR2J3 | Superior Cervical Ganglion |
| OR2S2 | Uterus Corpus |
| OR2W1 | Superior Cervical Ganglion |
| OR3A2 | Superior Cervical Ganglion |
| OR52A1 | Testis Seminiferous Tubule |
| OR5I1 | Lymphoma burkitts Raji |

FIG. 18AAAR

| | |
|---|---|
| OR6A2 | Superior Cervical Ganglion |
| OR7A5 | Appendix |
| OR7C1 | Testis Seminiferous Tubule |
| OR7E19P | Superior Cervical Ganglion |
| ORAI2 | CD19 Bcells neg. sel. |
| ORM1 | Liver |
| OSBP2 | CD71 Early Erythroid |
| OSBPL10 | CD19 Bcells neg. sel. |
| OSBPL3 | Colorectal adenocarcinoma |
| OSBPL7 | Tonsil |
| OSGEPL1 | CD4 T cells |
| OSM | CD71 Early Erythroid |
| OSR2 | Uterus |
| OTUD3 | Prefrontal Cortex |
| OTUD7B | Heart |
| OXCT2 | Testis Interstitial |
| OXSM | X721 B lymphoblasts |
| OXT | Hypothalamus |
| P2RX2 | Superior Cervical Ganglion |
| P2RX3 | CD71 Early Erythroid |
| P2RX6 | Skeletal Muscle |
| P2RY10 | CD19 Bcells neg. sel. |
| P2RY2 | Bronchial Epithelial Cells |
| P2RY4 | Superior Cervical Ganglion |

FIG. 18AAAS

| | |
|---|---|
| PADI3 | Pons |
| PAEP | Uterus |
| PAFAH2 | Thymus |
| PAGE1 | X721 B lymphoblasts |
| PAK1IP1 | Prostate |
| PAK7 | Fetal brain |
| PALB2 | X721 B lymphoblasts |
| PALMD | Fetal liver |
| PANK4 | Lymphoma burkitts Raji |
| PANX1 | Bronchial Epithelial Cells |
| PAPOLG | Fetal brain |
| PAPPA2 | Placenta |
| PAQR3 | Testis Germ Cell |
| PARD3 | Bronchial Epithelial Cells |
| PARG | Superior Cervical Ganglion |
| PARN | X721 B lymphoblasts |
| PARP11 | Appendix |
| PARP16 | Atrioventricular Node |
| PARP3 | X721 B lymphoblasts |
| PART1 | Prostate |
| PAWR | Uterus |
| PAX1 | Thymus |
| PAX2 | Kidney |
| PAX4 | Superior Cervical Ganglion |

FIG. 18AAAT

| | |
|---|---|
| PAX7 | Atrioventricular Node |
| PCCA | Colon |
| PCDH1 | Placenta |
| PCDH11X | Fetal brain |
| PCDH17 | Testis Intersitial |
| PCDH7 | Prefrontal Cortex |
| PCDHB1 | Superior Cervical Ganglion |
| PCDHB11 | Uterus Corpus |
| PCDHB13 | Pancreatic Islet |
| PCDHB3 | Testis |
| PCDHB6 | Superior Cervical Ganglion |
| PCK2 | Liver |
| PCNP | Liver |
| PCNT | Skeletal Muscle |
| PCNX | CD8 T cells |
| PCNXL2 | Prefrontal Cortex |
| PCOLCE | Liver |
| PCOLCE2 | Adipocyte |
| PCSK1 | Pancreatic Islet |
| PCYOX1 | Adipocyte |
| PCYT1A | Testis |
| PDC | retina |
| PDCD1 | Pons |
| PDCD1LG2 | Superior Cervical Ganglion |

FIG. 18AAAU

| | |
|---|---|
| PDE10A | Caudate nucleus |
| PDE1B | Caudate nucleus |
| PDE1C | pineal night |
| PDE3B | CD8 T cells |
| PDE6A | retina |
| PDE6G | retina |
| PDE7B | Trigeminal Ganglion |
| PDE9A | Prostate |
| PDGFRL | Fetal Thyroid |
| PDHA2 | Testis Interstitial |
| PDIA2 | Pancreas |
| PDK3 | X721 B lymphoblasts |
| PDLIM3 | Skeletal Muscle |
| PDLIM4 | Colorectal adenocarcinoma |
| PDPN | Placenta |
| PDPR | Superior Cervical Ganglion |
| PDSS1 | Leukemia lymphoblastic MOLT 24 |
| PDX1 | Heart |
| PDXP | CD14 Monocytes |
| PDZD3 | Superior Cervical Ganglion |
| PDZK1IP1 | Kidney |
| PDZRN4 | Atrioventricular Node |
| PECR | Liver |

FIG. 18AAAV

| | |
|---|---|
| PEPD | Kidney |
| PER3 | retina |
| PET112L | Heart |
| PEX11A | Prostate |
| PEX13 | Testis Intersitial |
| PEX19 | Adipocyte |
| PEX3 | X721 B lymphoblasts |
| PEX5L | Superior Cervical Ganglion |
| PF4 | Whole Blood |
| PF4V1 | Whole Blood |
| PFKFB1 | Liver |
| PFKFB2 | Pancreatic Islet |
| PFKFB3 | Skeletal Muscle |
| PGA3 | small intestine |
| PGAM1 | CD71 Early Erythroid |
| PGAP1 | Adrenal Cortex |
| PGGT1B | Ciliary Ganglion |
| PGK2 | Testis Intersitial |
| PGLYRP4 | Superior Cervical Ganglion |
| PGM3 | Smooth Muscle |
| PGPEP1 | Kidney |
| PGR | Uterus |
| PHACTR4 | X721 B lymphoblasts |
| PHC1 | Testis Germ Cell |

FIG. 18AAAW

| | |
|---|---|
| PHEX | BDCA4 Dentritic Cells |
| PHF7 | Testis Intersitial |
| PHKG1 | Superior Cervical Ganglion |
| PHKG2 | Testis |
| PHLDA2 | Placenta |
| PHOX2A | Uterus Corpus |
| PI15 | Testis Leydig Cell |
| PI3 | Tonsil |
| PI4K2A | CD71 Early Erythroid |
| PIAS2 | Testis Intersitial |
| PIAS3 | pineal day |
| PIAS4 | Whole Brain |
| PIBF1 | Testis Intersitial |
| PICK1 | Cerebellum Peduncles |
| PIGB | X721 B lymphoblasts |
| PIGL | Colorectal adenocarcinoma |
| PIGR | Trachea |
| PIGV | Testis |
| PIGZ | Pancreas |
| PIK3C2B | Thymus |
| PIK3CA | CD8 T cells |
| PIK3R2 | Fetal brain |
| PIK3R5 | CD56 NK Cells |
| PIP5K1B | CD71 Early Erythroid |

FIG. 18AAAX

| | |
|---|---|
| PIPOX | Liver |
| PIR | Bronchial Epithelial Cells |
| PITPNM3 | Superior Cervical Ganglion |
| PITX1 | Tongue |
| PITX2 | retina |
| PITX3 | Adrenal gland |
| PKD2 | Uterus |
| PKDREJ | CD14 Monocytes |
| PKLR | Liver |
| PKMYT1 | CD71 Early Erythroid |
| PKP2 | Colon |
| PLA1A | X721 B lymphoblasts |
| PLA2G12A | CD105 Endothelial |
| PLA2G2E | Superior Cervical Ganglion |
| PLA2G2F | Trigeminal Ganglion |
| PLA2G3 | Skeletal Muscle |
| PLA2G4A | Smooth Muscle |
| PLA2G7 | CD14 Monocytes |
| PLAA | X721 B lymphoblasts |
| PLAC1 | Placenta |
| PLAC4 | Placenta |
| PLAG1 | Trigeminal Ganglion |
| PLAGL2 | Testis |
| PLCB2 | CD14 Monocytes |

FIG. 18AAAY

| | |
|---|---|
| PLCB3 | small intestine |
| PLCB4 | Thalamus |
| PLCXD1 | X721 B lymphoblasts |
| PLD1 | X721 B lymphoblasts |
| PLEK2 | Bronchial Epithelial Cells |
| PLEKHA2 | Superior Cervical Ganglion |
| PLEKHA6 | Placenta |
| PLEKHA8 | CD56 NK Cells |
| PLEKHF2 | CD19 Bcells neg. sel. |
| PLEKHH3 | Superior Cervical Ganglion |
| PLK1 | X721 B lymphoblasts |
| PLK3 | CD33 Myeloid |
| PLK4 | CD71 Early Erythroid |
| PLN | Uterus |
| PLOD2 | Smooth Muscle |
| PLS1 | Colon |
| PLSCR2 | Testis Interstitial |
| PLUNC | Trachea |
| PLXNA1 | Fetal brain |
| PLXNC1 | Whole Blood |
| PMCH | Hypothalamus |
| PMCHL1 | Hypothalamus |
| PMEPA1 | Prostate |
| PNMT | Adrenal Cortex |

FIG. 18AAAZ

| | |
|---|---|
| PNPLA2 | Adipocyte |
| PNPLA3 | Atrioventricular Node |
| PNPLA4 | Bronchial Epithelial Cells |
| POF1B | Skin |
| POFUT2 | Smooth Muscle |
| POLE2 | Leukemia lymphoblastic MOLT 25 |
| POLL | CD71 Early Erythroid |
| POLM | CD19 Bcells neg. sel. |
| POLQ | Lymphoma burkitts Daudi |
| POLR1C | Leukemia promyelocytic HL65 |
| POLR2D | Testis |
| POLR2J | Trigeminal Ganglion |
| POLR3B | X721 B lymphoblasts |
| POLR3C | CD71 Early Erythroid |
| POLR3D | X721 B lymphoblasts |
| POLR3G | Leukemia promyelocytic HL66 |
| POLRMT | Testis |
| POM121L2 | Superior Cervical Ganglion |
| POMC | Pituitary |
| POMGNT1 | Heart |
| POMT1 | Testis |
| POMZP3 | Testis Germ Cell |

FIG. 18AAAAA

| | |
|---|---|
| PON3 | Liver |
| POP1 | Dorsal Root Ganglion |
| POPDC2 | Heart |
| POSTN | Cardiac Myocytes |
| POU2F3 | Trigeminal Ganglion |
| POU3F3 | Superior Cervical Ganglion |
| POU3F4 | Ciliary Ganglion |
| POU4F2 | Superior Cervical Ganglion |
| POU5F1 | Pituitary |
| POU5F1P3 | Uterus Corpus |
| POU5F1P4 | Ciliary Ganglion |
| PP14571 | Placenta |
| PPA1 | Heart |
| PPARD | Placenta |
| PPARG | Adipocyte |
| PPARGC1A | Salivary gland |
| PPAT | X721 B lymphoblasts |
| PPBPL2 | Superior Cervical Ganglion |
| PPCDC | X721 B lymphoblasts |
| PPEF2 | retina |
| PPFIA2 | pineal day |
| PPFIBP1 | Colorectal adenocarcinoma |
| PPIL2 | Leukemia chronic Myelogenous K588 |

FIG. 18AAAAB

| | |
|---|---|
| PPIL6 | Liver |
| PPM1D | CD51 |
| PPM1H | Cerebellum |
| PPOX | CD71 Early Erythroid |
| PPP1R12B | Uterus |
| PPP1R13B | Thyroid |
| PPP1R3D | Whole Blood |
| PPP2R2D | Whole Brain |
| PPP3R1 | Whole Blood |
| PPP5C | X721 B lymphoblasts |
| PPRC1 | CD105 Endothelial |
| PPT2 | Olfactory Bulb |
| PPY | Pancreatic Islet |
| PPY2 | Superior Cervical Ganglion |
| PQLC2 | Skeletal Muscle |
| PRAME | Leukemia chronic Myelogenous K589 |
| PRDM1 | Superior Cervical Ganglion |
| PRDM11 | CD52 |
| PRDM12 | Cardiac Myocytes |
| PRDM13 | Superior Cervical Ganglion |
| PRDM16 | Superior Cervical Ganglion |
| PRDM5 | Skeletal Muscle |
| PRDM8 | Superior Cervical Ganglion |

FIG. 18AAAAC

| | |
|---|---|
| PREP | X721 B lymphoblasts |
| PRF1 | CD56 NK Cells |
| PRG3 | Bone marrow |
| PRICKLE3 | X721 B lymphoblasts |
| PRKAA1 | Testis Intersitial |
| PRKAB1 | CD71 Early Erythroid |
| PRKAB2 | Dorsal Root Ganglion |
| PRKCG | Superior Cervical Ganglion |
| PRKCH | CD56 NK Cells |
| PRKRIP1 | Colorectal adenocarcinoma |
| PRKY | CD4 T cells |
| PRL | Pituitary |
| PRLH | Trigeminal Ganglion |
| PRM2 | Testis Leydig Cell |
| PRMT3 | Leukemia promyelocytic HL67 |
| PRMT7 | BDCA4 Dentritic Cells |
| PRND | Testis Germ Cell |
| PRO1768 | Trigeminal Ganglion |
| PRO2012 | Appendix |
| PROC | Liver |
| PROCR | Placenta |
| PROL1 | Salivary gland |
| PROP1 | Trigeminal Ganglion |

FIG. 18AAAAD

| | |
|---|---|
| PROZ | Superior Cervical Ganglion |
| PRPS2 | Ovary |
| PRR3 | Leukemia lymphoblastic MOLT 26 |
| PRR5 | CD71 Early Erythroid |
| PRR7 | X721 B lymphoblasts |
| PRRC1 | BDCA4 Dentritic Cells |
| PRRG1 | Spinal Cord |
| PRRG2 | Parietal Lobe |
| PRRG3 | Salivary gland |
| PRRX1 | Adipocyte |
| PRSS12 | Superior Cervical Ganglion |
| PRSS16 | Thymus |
| PRSS21 | Testis |
| PRSS8 | Placenta |
| PSCA | Prostate |
| PSD | Subthalamic Nucleus |
| PSG1 | Placenta |
| PSG11 | Placenta |
| PSG2 | Placenta |
| PSG3 | Placenta |
| PSG4 | Placenta |
| PSG5 | Placenta |
| PSG6 | Placenta |

FIG. 18AAAAE

| | |
|---|---|
| PSG7 | Placenta |
| PSG9 | Placenta |
| PSKH1 | Testis |
| PSMB4 | Superior Cervical Ganglion |
| PSMD5 | Leukemia chronic Myelogenous K590 |
| PSPH | Lymphoma burkitts Raji |
| PSPN | Trigeminal Ganglion |
| PSTPIP2 | Bone marrow |
| PTCH2 | Fetal brain |
| PTDSS2 | Lymphoma burkitts Raji |
| PTER | Kidney |
| PTGDR | CD56 NK Cells |
| PTGER2 | CD56 NK Cells |
| PTGES2 | X721 B lymphoblasts |
| PTGES3 | Superior Cervical Ganglion |
| PTGFR | Uterus |
| PTGIR | CD14 Monocytes |
| PTGS1 | Smooth Muscle |
| PTGS2 | Smooth Muscle |
| PTH2R | Superior Cervical Ganglion |
| PTHLH | Bronchial Epithelial Cells |
| PTK7 | BDCA4 Dentritic Cells |
| PTPLA | CD53 |

FIG. 18AAAAF

| | |
|---|---|
| PTPN1 | CD19 Bcells neg. sel. |
| PTPN21 | Testis |
| PTPN3 | Thalamus |
| PTPN9 | Appendix |
| PTPRG | Adipocyte |
| PTPRH | Pancreas |
| PTPRS | BDCA4 Dentritic Cells |
| PURG | Skeletal Muscle |
| PUS3 | Skeletal Muscle |
| PUS7L | Superior Cervical Ganglion |
| PVALB | Cerebellum |
| PVRL3 | Placenta |
| PXDN | Smooth Muscle |
| PXMP2 | Liver |
| PXMP4 | Lung |
| PYGM | Skeletal Muscle |
| PYGO1 | Skeletal Muscle |
| PYHIN1 | Superior Cervical Ganglion |
| PYY | Colon |
| PZP | Skin |
| QPRT | Liver |
| QRSL1 | CD19 Bcells neg. sel. |
| QTRT1 | Thyroid |
| RAB11B | Thyroid |

FIG. 18AAAAG

| | |
|---|---|
| RAB11FIP3 | Kidney |
| RAB17 | Liver |
| RAB23 | Uterus |
| RAB25 | Tongue |
| RAB30 | Liver |
| RAB33A | Whole Brain |
| RAB38 | Bronchial Epithelial Cells |
| RAB3D | Atrioventricular Node |
| RAB40A | Dorsal Root Ganglion |
| RAB40C | Superior Cervical Ganglion |
| RAB4B | BDCA4 Dentritic Cells |
| RABL2A | Fetal brain |
| RAC3 | Whole Brain |
| RAD51L1 | Superior Cervical Ganglion |
| RAD52 | Lymphoma burkitts Raji |
| RAD9A | CD105 Endothelial |
| RAG1 | Thymus |
| RALGPS1 | Fetal brain |
| RAMP1 | Uterus |
| RAMP2 | Lung |
| RAMP3 | Lung |
| RANBP10 | CD71 Early Erythroid |
| RANBP17 | Colorectal adenocarcinoma |
| RAP2C | Uterus |

FIG. 18AAAAH

| | |
|---|---|
| RAPGEF1 | Uterus Corpus |
| RAPGEF4 | Amygdala |
| RAPGEFL1 | Whole Brain |
| RAPSN | Skeletal Muscle |
| RARA | Whole Blood |
| RARB | Superior Cervical Ganglion |
| RARS2 | Uterus Corpus |
| RASA1 | Placenta |
| RASA2 | CD8 T cells |
| RASA3 | CD56 NK Cells |
| RASAL1 | Lymphoma burkitts Raji |
| RASGRF1 | Cerebellum |
| RASGRP3 | CD19 Bcells neg. sel. |
| RASSF7 | Pancreas |
| RASSF8 | Testis Intersitial |
| RASSF9 | Appendix |
| RAVER2 | Ciliary Ganglion |
| RAX | Cerebellum Peduncles |
| RBBP5 | CD14 Monocytes |
| RBM19 | Superior Cervical Ganglion |
| RBM4B | Fetal brain |
| RBM7 | Whole Blood |
| RBMY1A1 | Testis |
| RBP4 | Liver |

FIG. 18AAAAI

| | |
|---|---|
| RBPJL | Pancreas |
| RBX1 | CD71 Early Erythroid |
| RC3H2 | BDCA4 Dentritic Cells |
| RCAN3 | Prostate |
| RCBTB2 | Leukemia lymphoblastic MOLT 27 |
| RCN3 | Smooth Muscle |
| RDH11 | Prostate |
| RDH16 | Liver |
| RDH8 | retina |
| RECQL4 | CD105 Endothelial |
| RECQL5 | Skeletal Muscle |
| RELB | Lymphoma burkitts Raji |
| REN | Ovary |
| RENBP | Kidney |
| RERGL | Uterus |
| RETSAT | Adipocyte |
| REV3L | Uterus |
| REXO4 | CD19 Bcells neg. sel. |
| RFC1 | Leukemia lymphoblastic MOLT 28 |
| RFC2 | X721 B lymphoblasts |
| RFNG | Liver |
| RFPL3 | Superior Cervical Ganglion |
| RFWD3 | CD105 Endothelial |

FIG. 18AAAAJ

| RFX1 | Superior Cervical Ganglion |
|---|---|
| RFX3 | Trigeminal Ganglion |
| RFXAP | Pituitary |
| RGN | Adrenal gland |
| RGPD5 | Testis Intersitial |
| RGR | retina |
| RGS14 | Caudate nucleus |
| RGS17 | Pancreatic Islet |
| RGS3 | Heart |
| RGS6 | pineal night |
| RGS9 | Caudate nucleus |
| RHAG | CD71 Early Erythroid |
| RHBDF1 | Olfactory Bulb |
| RHBDL1 | Lymphoma burkitts Raji |
| RHBG | Atrioventricular Node |
| RHCE | CD71 Early Erythroid |
| RHD | CD71 Early Erythroid |
| RHO | retina |
| RHOBTB1 | Placenta |
| RHOBTB2 | Lung |
| RHOD | Bronchial Epithelial Cells |
| RIBC2 | Testis Intersitial |
| RIC3 | Cingulate Cortex |
| RIC8B | Caudate nucleus |

FIG. 18AAAAK

| | |
|---|---|
| RIN3 | CD14 Monocytes |
| RINT1 | Superior Cervical Ganglion |
| RIOK2 | Smooth Muscle |
| RIT1 | Whole Blood |
| RIT2 | Fetal brain |
| RLBP1 | retina |
| RLN1 | Prostate |
| RLN2 | Superior Cervical Ganglion |
| RMI1 | X721 B lymphoblasts |
| RMND1 | Trigeminal Ganglion |
| RMND5A | CD71 Early Erythroid |
| RMND5B | Testis |
| RNASE3 | Bone marrow |
| RNASEH2B | Leukemia lymphoblastic MOLT 29 |
| RNASEL | Whole Blood |
| RNF10 | CD71 Early Erythroid |
| RNF121 | Subthalamic Nucleus |
| RNF123 | CD71 Early Erythroid |
| RNF125 | CD8 T cells |
| RNF14 | CD71 Early Erythroid |
| RNF141 | Testis Intersitial |
| RNF17 | Testis Intersitial |
| RNF170 | Thyroid |

FIG. 18AAAAL

| | |
|---|---|
| RNF185 | Superior Cervical Ganglion |
| RNF19A | CD71 Early Erythroid |
| RNF32 | Testis Intersitial |
| RNF40 | CD71 Early Erythroid |
| RNFT1 | Testis Leydig Cell |
| RNMTL1 | Testis |
| ROBO1 | Fetal brain |
| ROPN1 | Testis Intersitial |
| ROR1 | Adipocyte |
| RORB | Superior Cervical Ganglion |
| RORC | Liver |
| RP2 | Whole Blood |
| RPA4 | Superior Cervical Ganglion |
| RPAIN | Lymphoma burkitts Daudi |
| RPE | Leukemia promyelocytic HL68 |
| RPE65 | retina |
| RPGRIP1 | Testis Intersitial |
| RPGRIP1L | Superior Cervical Ganglion |
| RPH3AL | Pancreatic Islet |
| RPL10L | Testis |
| RPL3L | Skeletal Muscle |
| RPP38 | Testis Germ Cell |
| RPRM | Fetal brain |

FIG. 18AAAAM

| | |
|---|---|
| RPS6KA4 | Pons |
| RPS6KA6 | Appendix |
| RPS6KB1 | CD4 T cells |
| RPS6KC1 | Testis Intersitial |
| RRAD | Skeletal Muscle |
| RRAGB | Superior Cervical Ganglion |
| RRH | retina |
| RRN3 | CD56 NK Cells |
| RRP12 | CD33 Myeloid |
| RRP9 | X721 B lymphoblasts |
| RS1 | retina |
| RSAD2 | CD71 Early Erythroid |
| RSF1 | Uterus |
| RTDR1 | Testis |
| RTN2 | Skeletal Muscle |
| RUNX1T1 | Fetal brain |
| RUNX2 | Pons |
| RWDD2A | Testis Germ Cell |
| RXFP3 | Superior Cervical Ganglion |
| RYR2 | Prefrontal Cortex |
| S100A12 | Bone marrow |
| S100A2 | Bronchial Epithelial Cells |
| S100A3 | Colorectal adenocarcinoma |
| S100A5 | Liver |

FIG. 18AAAAN

| | |
|---|---|
| S100G | Uterus Corpus |
| S1PR5 | CD56 NK Cells |
| SAA1 | Salivary gland |
| SAA3P | Skin |
| SAA4 | Liver |
| SAC3D1 | Testis |
| SAG | retina |
| SAMHD1 | CD33 Myeloid |
| SAMSN1 | Leukemia chronic Myelogenous K591 |
| SAR1B | small intestine |
| SARDH | Liver |
| SATB2 | Fetal brain |
| SBNO1 | Appendix |
| SCAMP3 | Atrioventricular Node |
| SCAND2 | Superior Cervical Ganglion |
| SCAPER | Fetal brain |
| SCARA3 | Uterus Corpus |
| SCGB1D2 | Skin |
| SCGB2A2 | Skin |
| SCGN | Pancreatic Islet |
| SCIN | Trigeminal Ganglion |
| SCLY | Liver |
| SCN3A | Fetal brain |

FIG. 18AAAAO

| | |
|---|---|
| SCN4A | Skeletal Muscle |
| SCN5A | Heart |
| SCN8A | Superior Cervical Ganglion |
| SCNN1B | Lung |
| SCNN1D | Superior Cervical Ganglion |
| SCO2 | CD33 Myeloid |
| SCRIB | Heart |
| SCRT1 | Superior Cervical Ganglion |
| SCT | BDCA4 Dentritic Cells |
| SCUBE3 | Superior Cervical Ganglion |
| SCYL2 | BDCA4 Dentritic Cells |
| SCYL3 | BDCA4 Dentritic Cells |
| SDCCAG3 | Lymphoma burkitts Raji |
| SDF2 | Whole Blood |
| SDPR | Fetal lung |
| SDS | Liver |
| SEC14L3 | Trigeminal Ganglion |
| SEC14L4 | CD71 Early Erythroid |
| SEC22B | Placenta |
| SECTM1 | Whole Blood |
| SEL1L | Pancreas |
| SELE | retina |
| SELP | Whole Blood |
| SEMA3A | Appendix |

FIG. 18AAAAP

| | |
|---|---|
| SEMA3B | Placenta |
| SEMA3D | Trigeminal Ganglion |
| SEMA4G | Fetal liver |
| SEMA5A | Olfactory Bulb |
| SEMA7A | Superior Cervical Ganglion |
| SEMG1 | Prostate |
| SEMG2 | Prostate |
| SENP2 | Testis Intersitial |
| SEPHS1 | Leukemia lymphoblastic MOLT 30 |
| SERPINA10 | Liver |
| SERPINA7 | Fetal liver |
| SERPINB13 | Tongue |
| SERPINB3 | Trachea |
| SERPINB4 | Superior Cervical Ganglion |
| SERPINB8 | CD33 Myeloid |
| SERPINE1 | Cardiac Myocytes |
| SERPINF2 | Liver |
| SETD4 | Testis |
| SETD8 | CD71 Early Erythroid |
| SETMAR | Atrioventricular Node |
| SF3A3 | Leukemia chronic Myelogenous K592 |
| SFMBT1 | Testis Germ Cell |
| SFRP5 | retina |

FIG. 18AAAAQ

| | |
|---|---|
| SFTPA2 | Lung |
| SFTPD | Lung |
| SGCA | Heart |
| SGCB | Olfactory Bulb |
| SGPL1 | Colorectal adenocarcinoma |
| SGPP1 | Placenta |
| SGTA | Heart |
| SH2D1A | Leukemia lymphoblastic MOLT 31 |
| SH2D3C | Thymus |
| SH3BGR | Skeletal Muscle |
| SH3TC1 | Thymus |
| SH3TC2 | Placenta |
| SHANK1 | CD56 NK Cells |
| SHC2 | Pancreatic Islet |
| SHC3 | Prefrontal Cortex |
| SHH | Superior Cervical Ganglion |
| SHOX2 | Thalamus |
| SHQ1 | Leukemia lymphoblastic MOLT 32 |
| SHROOM2 | pineal night |
| SI | small intestine |
| SIAH1 | Placenta |
| SIAH2 | CD71 Early Erythroid |
| SIGLEC1 | Lymph node |

FIG. 18AAAAR

| | |
|---|---|
| SIGLEC5 | Superior Cervical Ganglion |
| SIGLEC6 | Placenta |
| SILV | retina |
| SIM1 | Superior Cervical Ganglion |
| SIM2 | Skeletal Muscle |
| SIRPB1 | Whole Blood |
| SIRT1 | CD19 Bcells neg. sel. |
| SIRT4 | Superior Cervical Ganglion |
| SIRT5 | Heart |
| SIRT7 | CD33 Myeloid |
| SIX1 | Pituitary |
| SIX2 | Pituitary |
| SIX3 | retina |
| SIX5 | Superior Cervical Ganglion |
| SKAP1 | CD8 T cells |
| SLAMF1 | X721 B lymphoblasts |
| SLC10A1 | Liver |
| SLC10A2 | small intestine |
| SLC12A1 | Kidney |
| SLC12A2 | Trachea |
| SLC12A6 | Testis Intersitial |
| SLC12A9 | CD14 Monocytes |
| SLC13A2 | Kidney |
| SLC13A3 | Kidney |

FIG. 18AAAAS

| | |
|---|---|
| SLC13A4 | pineal night |
| SLC14A1 | CD71 Early Erythroid |
| SLC15A1 | Superior Cervical Ganglion |
| SLC16A10 | Superior Cervical Ganglion |
| SLC16A4 | Placenta |
| SLC16A8 | retina |
| SLC17A1 | Superior Cervical Ganglion |
| SLC17A3 | Kidney |
| SLC17A4 | Superior Cervical Ganglion |
| SLC17A5 | Placenta |
| SLC18A1 | Skeletal Muscle |
| SLC18A2 | Uterus |
| SLC19A2 | Adrenal Cortex |
| SLC19A3 | Placenta |
| SLC1A5 | Colorectal adenocarcinoma |
| SLC1A6 | Cerebellum |
| SLC1A7 | Trigeminal Ganglion |
| SLC20A2 | Thyroid |
| SLC22A1 | Liver |
| SLC22A13 | Superior Cervical Ganglion |
| SLC22A18AS | Lymphoma burkitts Raji |
| SLC22A2 | Kidney |
| SLC22A3 | Prostate |
| SLC22A4 | CD71 Early Erythroid |

FIG. 18AAAAT

| | |
|---|---|
| SLC22A6 | Kidney |
| SLC22A7 | Liver |
| SLC22A8 | Kidney |
| SLC24A1 | retina |
| SLC24A2 | Ciliary Ganglion |
| SLC24A6 | Adrenal gland |
| SLC25A10 | Liver |
| SLC25A11 | Heart |
| SLC25A17 | X721 B lymphoblasts |
| SLC25A21 | Leukemia chronic Myelogenous K593 |
| SLC25A28 | BDCA4 Dentritic Cells |
| SLC25A31 | Testis |
| SLC25A37 | Bone marrow |
| SLC25A38 | CD71 Early Erythroid |
| SLC25A4 | Skeletal Muscle |
| SLC25A42 | Superior Cervical Ganglion |
| SLC26A2 | Colon |
| SLC26A3 | Colon |
| SLC26A4 | Thyroid |
| SLC26A6 | Leukemia lymphoblastic MOLT 33 |
| SLC27A2 | Kidney |
| SLC27A5 | Liver |
| SLC27A6 | Olfactory Bulb |

FIG. 18AAAAU

| | |
|---|---|
| SLC28A3 | Pons |
| SLC29A1 | CD71 Early Erythroid |
| SLC2A11 | pineal day |
| SLC2A14 | Colorectal adenocarcinoma |
| SLC2A2 | Fetal liver |
| SLC2A6 | CD14 Monocytes |
| SLC30A10 | Fetal liver |
| SLC31A1 | CD105 Endothelial |
| SLC33A1 | BDCA4 Dentritic Cells |
| SLC34A1 | Kidney |
| SLC35A3 | Colon |
| SLC35C1 | Colorectal adenocarcinoma |
| SLC35E3 | Prostate |
| SLC37A1 | X721 B lymphoblasts |
| SLC37A4 | Liver |
| SLC38A3 | Liver |
| SLC38A4 | Fetal liver |
| SLC38A6 | CD105 Endothelial |
| SLC38A7 | Prefrontal Cortex |
| SLC39A7 | Prostate |
| SLC3A1 | Kidney |
| SLC41A3 | Testis |
| SLC45A2 | retina |
| SLC47A1 | Adrenal Cortex |

FIG. 18AAAAV

| | |
|---|---|
| SLC4A1 | CD71 Early Erythroid |
| SLC4A3 | Heart |
| SLC5A1 | small intestine |
| SLC5A2 | Kidney |
| SLC5A4 | Superior Cervical Ganglion |
| SLC5A5 | Thyroid |
| SLC5A6 | Placenta |
| SLC6A11 | Skeletal Muscle |
| SLC6A12 | Kidney |
| SLC6A14 | Fetal lung |
| SLC6A15 | Bronchial Epithelial Cells |
| SLC6A20 | Trigeminal Ganglion |
| SLC6A4 | pineal night |
| SLC6A7 | Superior Cervical Ganglion |
| SLC6A9 | CD71 Early Erythroid |
| SLC9A1 | Placenta |
| SLC9A3 | Superior Cervical Ganglion |
| SLC9A5 | Prefrontal Cortex |
| SLC9A8 | CD33 Myeloid |
| SLCO2B1 | Liver |
| SLCO4C1 | Ciliary Ganglion |
| SLCO5A1 | X721 B lymphoblasts |
| SLFN12 | CD33 Myeloid |
| SLIT1 | Leukemia lymphoblastic |

FIG. 18AAAAW

| | MOLT 34 |
|---|---|
| SLIT3 | Adipocyte |
| SLITRK3 | Subthalamic Nucleus |
| SLMO1 | Superior Cervical Ganglion |
| SLURP1 | Tongue |
| SMC2 | Leukemia lymphoblastic MOLT 35 |
| SMCHD1 | Whole Blood |
| SMCP | Testis Intersitial |
| SMG6 | Appendix |
| SMR3A | Salivary gland |
| SMR3B | Salivary gland |
| SMURF1 | Testis |
| SMYD3 | Leukemia chronic Myelogenous K594 |
| SMYD5 | Pancreas |
| SNAPC1 | Testis Intersitial |
| SNAPC4 | Testis |
| SNCAIP | Uterus Corpus |
| SNIP1 | Globus Pallidus |
| SNX1 | Fetal Thyroid |
| SNX16 | Trigeminal Ganglion |
| SNX19 | Superior Cervical Ganglion |
| SNX2 | CD19 Bcells neg. sel. |
| SNX24 | Spinal Cord |

FIG. 18AAAAX

| | |
|---|---|
| SOAT1 | Adrenal gland |
| SOAT2 | Fetal liver |
| SOCS1 | Lymphoma burkitts Raji |
| SOCS2 | Leukemia chronic Myelogenous K595 |
| SOCS6 | Colon |
| SOD3 | Thyroid |
| SOHLH2 | X721 B lymphoblasts |
| SOS1 | Adipocyte |
| SOSTDC1 | retina |
| SOX1 | Superior Cervical Ganglion |
| SOX11 | Fetal brain |
| SOX12 | Fetal brain |
| SOX18 | Superior Cervical Ganglion |
| SOX5 | Testis Intersitial |
| SP140 | CD19 Bcells neg. sel. |
| SPA17 | Testis Intersitial |
| SPAG1 | Appendix |
| SPAG11B | Testis Leydig Cell |
| SPAG6 | Testis |
| SPANXB1 | Testis Seminiferous Tubule |
| SPAST | Fetal brain |
| SPATA2 | Testis |
| SPATA5L1 | Leukemia promyelocytic HL69 |

FIG. 18AAAAY

| | |
|---|---|
| SPATA6 | Testis Intersitial |
| SPC25 | Leukemia chronic Myelogenous K596 |
| SPCS3 | BDCA4 Dentritic Cells |
| SPDEF | Prostate |
| SPEG | Uterus |
| SPIB | Lymphoma burkitts Raji |
| SPINT3 | Testis Germ Cell |
| SPO11 | Trigeminal Ganglion |
| SPPL2B | CD54 |
| SPR | Liver |
| SPRED2 | Thymus |
| SRD5A1 | Fetal brain |
| SRD5A2 | Liver |
| SREBF1 | Adrenal Cortex |
| SRF | CD71 Early Erythroid |
| SRR | Superior Cervical Ganglion |
| SSH3 | Bronchial Epithelial Cells |
| SSR3 | Prostate |
| SSSCA1 | CD105 Endothelial |
| SST | Pancreatic Islet |
| SSTR1 | Atrioventricular Node |
| SSTR4 | Ciliary Ganglion |
| SSTR5 | Subthalamic Nucleus |

FIG. 18AAAAZ

| | |
|---|---|
| SSX2 | Superior Cervical Ganglion |
| SSX5 | Liver |
| ST3GAL1 | CD8 T cells |
| ST6GALNAC4 | CD71 Early Erythroid |
| ST7 | X721 B lymphoblasts |
| ST7L | Ovary |
| ST8SIA2 | Superior Cervical Ganglion |
| ST8SIA4 | Whole Blood |
| ST8SIA5 | Adrenal gland |
| STAB2 | Lymph node |
| STAC | Ciliary Ganglion |
| STAG3L4 | Appendix |
| STAM2 | Testis Intersitial |
| STARD13 | X721 B lymphoblasts |
| STARD5 | Uterus Corpus |
| STAT2 | BDCA4 Dentritic Cells |
| STAT5A | Leukemia lymphoblastic MOLT 36 |
| STBD1 | Pancreatic Islet |
| STC1 | Smooth Muscle |
| STEAP1 | Prostate |
| STEAP3 | CD71 Early Erythroid |
| STIL | Trigeminal Ganglion |
| STK11 | CD71 Early Erythroid |

FIG. 18AAAAAA

| | |
|---|---|
| STK16 | X721 B lymphoblasts |
| STMN3 | Amygdala |
| STON1 | Uterus |
| STRN | Ciliary Ganglion |
| STRN3 | Uterus |
| STS | Placenta |
| STX17 | Superior Cervical Ganglion |
| STX2 | CD8 T cells |
| STX3 | Whole Blood |
| STX6 | Whole Blood |
| STYK1 | Trigeminal Ganglion |
| SUCLG1 | Kidney |
| SULT1A3 | Ciliary Ganglion |
| SULT2A1 | Adrenal gland |
| SULT2B1 | Tongue |
| SUOX | Liver |
| SUPT3H | Testis Seminiferous Tubule |
| SUPV3L1 | Leukemia promyelocytic HL70 |
| SURF2 | Testis Germ Cell |
| SUV39H1 | CD71 Early Erythroid |
| SVEP1 | Placenta |
| SYCP1 | Testis Intersitial |
| SYCP2 | Testis Leydig Cell |

FIG. 18AAAAAB

| | |
|---|---|
| SYDE1 | Placenta |
| SYF2 | Skeletal Muscle |
| SYN3 | Skeletal Muscle |
| SYNGR4 | Testis |
| SYNPO2L | Heart |
| SYP | pineal night |
| SYT12 | Trigeminal Ganglion |
| T | X721 B lymphoblasts |
| TAAR3 | Superior Cervical Ganglion |
| TAAR5 | Superior Cervical Ganglion |
| TAC1 | Caudate nucleus |
| TAC3 | Placenta |
| TACR3 | Pancreas |
| TAF4 | Leukemia lymphoblastic MOLT 37 |
| TAF5L | CD71 Early Erythroid |
| TAF7L | Testis Germ Cell |
| TAL1 | CD71 Early Erythroid |
| TANC2 | Superior Cervical Ganglion |
| TAP2 | CD56 NK Cells |
| TARBP1 | CD55 |
| TAS2R1 | Globus Pallidus |
| TAS2R14 | Superior Cervical Ganglion |
| TAS2R7 | Superior Cervical Ganglion |

FIG. 18AAAAAC

| | |
|---|---|
| TAS2R9 | Subthalamic Nucleus |
| TASP1 | Superior Cervical Ganglion |
| TAT | Liver |
| TBC1D12 | Spinal Cord |
| TBC1D13 | Kidney |
| TBC1D16 | Adipocyte |
| TBC1D22A | CD19 Bcells neg. sel. |
| TBC1D22B | CD71 Early Erythroid |
| TBC1D29 | Dorsal Root Ganglion |
| TBC1D8B | Pituitary |
| TBCA | Superior Cervical Ganglion |
| TBCD | Leukemia lymphoblastic MOLT 38 |
| TBCE | CD56 |
| TBL1Y | Superior Cervical Ganglion |
| TBL2 | Testis |
| TBP | Testis Interstitial |
| TBRG4 | Lymphoma burkitts Raji |
| TBX10 | Skeletal Muscle |
| TBX19 | Pituitary |
| TBX21 | CD56 NK Cells |
| TBX3 | Adrenal gland |
| TBX4 | Temporal Lobe |
| TBX5 | Superior Cervical Ganglion |

FIG. 18AAAAAD

| | |
|---|---|
| TCHH | Placenta |
| TCL1B | Atrioventricular Node |
| TCL6 | Cardiac Myocytes |
| TCN2 | Kidney |
| TCP11 | Testis Intersitial |
| TDP1 | Testis Intersitial |
| TEAD3 | Placenta |
| TEAD4 | Colorectal adenocarcinoma |
| TEC | Liver |
| TECTA | Superior Cervical Ganglion |
| TESK2 | CD19 Bcells neg. sel. |
| TEX13B | Skeletal Muscle |
| TEX14 | Testis Seminiferous Tubule |
| TEX15 | Testis Seminiferous Tubule |
| TEX28 | Testis |
| TFAP2A | Placenta |
| TFAP2B | Skeletal Muscle |
| TFAP2C | Placenta |
| TFB1M | Leukemia promyelocytic HL71 |
| TFB2M | Leukemia chronic Myelogenous K597 |
| TFCP2L1 | Salivary gland |
| TFDP1 | CD71 Early Erythroid |
| TFDP3 | Superior Cervical Ganglion |

FIG. 18AAAAAE

| | |
|---|---|
| TFEC | CD33 Myeloid |
| TFF3 | Pancreas |
| TFR2 | Liver |
| TGDS | Pancreas |
| TGFB1I1 | Uterus |
| TGM2 | Placenta |
| TGM3 | Tongue |
| TGM4 | Prostate |
| TGM5 | Liver |
| TGS1 | CD105 Endothelial |
| THADA | CD4 T cells |
| THAP10 | Whole Brain |
| THAP3 | Lymphoma burkitts Raji |
| THBS3 | Testis |
| THG1L | CD105 Endothelial |
| THNSL2 | Liver |
| THRB | Superior Cervical Ganglion |
| THSD1 | Pancreas |
| THSD4 | Superior Cervical Ganglion |
| THSD7A | Placenta |
| THUMPD2 | Leukemia lymphoblastic MOLT 39 |
| TIMM22 | Whole Brain |
| TIMM50 | Skin |

FIG. 18AAAAAF

| | |
|---|---|
| TIMM8B | Heart |
| TIMP2 | Placenta |
| TLE3 | Whole Blood |
| TLE6 | CD71 Early Erythroid |
| TLL1 | Superior Cervical Ganglion |
| TLL2 | Heart |
| TLR3 | Testis Interstitial |
| TLR7 | BDCA4 Dentritic Cells |
| TLX3 | Cardiac Myocytes |
| TM4SF20 | small intestine |
| TM4SF5 | Liver |
| TM7SF2 | Adrenal gland |
| TMCC1 | Pancreas |
| TMCC2 | CD71 Early Erythroid |
| TMCO3 | Smooth Muscle |
| TMEM104 | Skin |
| TMEM11 | CD71 Early Erythroid |
| TMEM110 | Liver |
| TMEM121 | CD14 Monocytes |
| TMEM135 | Adipocyte |
| TMEM140 | Whole Blood |
| TMEM149 | BDCA4 Dentritic Cells |
| TMEM159 | Heart |
| TMEM186 | X721 B lymphoblasts |

FIG. 18AAAAAG

| | |
|---|---|
| TMEM187 | Lung |
| TMEM19 | Superior Cervical Ganglion |
| TMEM2 | Placenta |
| TMEM209 | Superior Cervical Ganglion |
| TMEM39A | Pituitary |
| TMEM45A | Skin |
| TMEM48 | X721 B lymphoblasts |
| TMEM53 | Liver |
| TMEM57 | CD71 Early Erythroid |
| TMEM62 | Cingulate Cortex |
| TMEM63A | CD4 T cells |
| TMEM70 | Skeletal Muscle |
| TMLHE | Superior Cervical Ganglion |
| TMPRSS2 | Prostate |
| TMPRSS3 | small intestine |
| TMPRSS5 | Olfactory Bulb |
| TMPRSS6 | Liver |
| TNFAIP6 | Smooth Muscle |
| TNFRSF10C | Whole Blood |
| TNFRSF10D | Cardiac Myocytes |
| TNFRSF11A | Appendix |
| TNFRSF11B | Thyroid |
| TNFRSF14 | Lymphoma burkitts Raji |
| TNFRSF25 | CD4 T cells |

FIG. 18AAAAAH

| | |
|---|---|
| TNFRSF4 | Lymph node |
| TNFRSF8 | X721 B lymphoblasts |
| TNFRSF9 | Ciliary Ganglion |
| TNFSF11 | Lymph node |
| TNFSF14 | X721 B lymphoblasts |
| TNFSF8 | CD4 T cells |
| TNFSF9 | Leukemia promyelocytic HL72 |
| TNIP2 | Lymphoma burkitts Raji |
| TNN | pineal night |
| TNNI1 | Skeletal Muscle |
| TNNI3 | Heart |
| TNNI3K | Superior Cervical Ganglion |
| TNNT1 | Skeletal Muscle |
| TNNT2 | Heart |
| TNP1 | Testis Intersitial |
| TNP2 | Testis Intersitial |
| TNR | Skeletal Muscle |
| TNS4 | Colorectal adenocarcinoma |
| TNXA | Adrenal Cortex |
| TNXB | Adrenal Cortex |
| TOM1L1 | Bronchial Epithelial Cells |
| TOMM22 | X721 B lymphoblasts |
| TOP3B | Leukemia chronic Myelogenous K598 |

FIG. 18AAAAAI

| | |
|---|---|
| TOX3 | Colon |
| TOX4 | Superior Cervical Ganglion |
| TP53BP1 | pineal night |
| TP73 | Skeletal Muscle |
| TPPP3 | Placenta |
| TPSAB1 | Lung |
| TRABD | BDCA4 Dentritic Cells |
| TRADD | CD4 T cells |
| TRAF1 | X721 B lymphoblasts |
| TRAF2 | Lymphoma burkitts Raji |
| TRAF3IP2 | Bronchial Epithelial Cells |
| TRAF6 | Leukemia chronic Myelogenous K599 |
| TRAK1 | CD19 Bcells neg. sel. |
| TRAK2 | CD71 Early Erythroid |
| TRDMT1 | Superior Cervical Ganglion |
| TRDN | Tongue |
| TREH | Kidney |
| TREML2 | Placenta |
| TRH | Hypothalamus |
| TRIM10 | CD71 Early Erythroid |
| TRIM13 | Testis Intersitial |
| TRIM15 | Pancreas |
| TRIM17 | Ciliary Ganglion |

FIG. 18AAAAAJ

| | |
|---|---|
| TRIM21 | Whole Blood |
| TRIM23 | Amygdala |
| TRIM25 | Placenta |
| TRIM29 | Tongue |
| TRIM31 | Skeletal Muscle |
| TRIM32 | Cerebellum |
| TRIM36 | Amygdala |
| TRIM46 | CD71 Early Erythroid |
| TRIM68 | CD56 NK Cells |
| TRIO | Fetal brain |
| TRIP10 | Skeletal Muscle |
| TRIP11 | Testis Intersitial |
| TRMT12 | CD105 Endothelial |
| TRMU | CD8 T cells |
| TRPA1 | Superior Cervical Ganglion |
| TRPC5 | Superior Cervical Ganglion |
| TRPM1 | retina |
| TRPM2 | BDCA4 Dentritic Cells |
| TRPM8 | Skeletal Muscle |
| TRPV4 | Superior Cervical Ganglion |
| TRRAP | Leukemia lymphoblastic MOLT 40 |
| TSGA10 | Testis Intersitial |
| TSHB | Pituitary |

FIG. 18AAAAAK

| | |
|---|---|
| TSKS | Testis Intersitial |
| TSPAN1 | Trachea |
| TSPAN15 | Olfactory Bulb |
| TSPAN32 | CD8 T cells |
| TSPAN5 | CD71 Early Erythroid |
| TSPAN9 | Heart |
| TSSC4 | Heart |
| TSTA3 | CD105 Endothelial |
| TTC15 | Testis Intersitial |
| TTC22 | Superior Cervical Ganglion |
| TTC23 | Lymphoma burkitts Raji |
| TTC27 | Leukemia chronic Myelogenous K600 |
| TTC28 | Fetal brain |
| TTC9 | Fetal brain |
| TTLL12 | CD105 Endothelial |
| TTLL4 | Testis |
| TTLL5 | Testis Intersitial |
| TTPA | Atrioventricular Node |
| TTTY9A | Superior Cervical Ganglion |
| TUBA4B | Lymphoma burkitts Raji |
| TUBA8 | Superior Cervical Ganglion |
| TUBAL3 | small intestine |
| TUBB4Q | Skeletal Muscle |

FIG. 18AAAAAL

| | |
|---|---|
| TUBD1 | Superior Cervical Ganglion |
| TUFM | Superior Cervical Ganglion |
| TUFT1 | Skin |
| TWSG1 | Smooth Muscle |
| TYR | retina |
| TYRP1 | retina |
| U2AF1 | Superior Cervical Ganglion |
| UAP1L1 | X721 B lymphoblasts |
| UBA1 | Superior Cervical Ganglion |
| UBE2D1 | Whole Blood |
| UBE2D4 | Liver |
| UBFD1 | CD105 Endothelial |
| UBQLN3 | Testis Intersitial |
| UCN | pineal night |
| UCP1 | Fetal Thyroid |
| UFC1 | Trigeminal Ganglion |
| UGT2A1 | Atrioventricular Node |
| UGT2B15 | Liver |
| UGT2B17 | Appendix |
| ULBP1 | Cerebellum |
| ULBP2 | Bronchial Epithelial Cells |
| UMOD | Kidney |
| UNC119 | Lymphoma burkitts Raji |
| UNC5C | Superior Cervical Ganglion |

FIG. 18AAAAAM

| | |
|---|---|
| UNC93A | Fetal liver |
| UNC93B1 | BDCA4 Dentritic Cells |
| UPB1 | Liver |
| UPF1 | Prostate |
| UPK1A | Prostate |
| UPK1B | Trachea |
| UPK3A | Prostate |
| UPK3B | Lung |
| UPP1 | Bronchial Epithelial Cells |
| UQCC | Lymphoma burkitts Raji |
| UQCRC1 | Heart |
| UQCRFS1 | Superior Cervical Ganglion |
| URM1 | Heart |
| UROD | CD71 Early Erythroid |
| USH2A | pineal day |
| USP10 | Whole Blood |
| USP12 | CD71 Early Erythroid |
| USP13 | Skeletal Muscle |
| USP18 | X721 B lymphoblasts |
| USP19 | Trigeminal Ganglion |
| USP2 | Testis Germ Cell |
| USP27X | Superior Cervical Ganglion |
| USP29 | Superior Cervical Ganglion |
| USP32 | Testis Intersitial |

FIG. 18AAAAAN

| | |
|---|---|
| USP6NL | Atrioventricular Node |
| UTRN | Testis Intersitial |
| UTS2 | CD56 NK Cells |
| UTY | Ciliary Ganglion |
| UVRAG | CD19 Bcells neg. sel. |
| VAC14 | Skeletal Muscle |
| VARS | X721 B lymphoblasts |
| VASH1 | pineal night |
| VASH2 | Fetal brain |
| VASP | Whole Blood |
| VAV2 | CD19 Bcells neg. sel. |
| VAV3 | Placenta |
| VAX2 | Superior Cervical Ganglion |
| VCPIP1 | CD33 Myeloid |
| VENTX | CD33 Myeloid |
| VGF | Pancreatic Islet |
| VGLL1 | Placenta |
| VGLL3 | Placenta |
| VILL | Colon |
| VIPR1 | Lung |
| VLDLR | Pancreatic Islet |
| VNN2 | Whole Blood |
| VNN3 | CD33 Myeloid |
| VPRBP | Testis Intersitial |

FIG. 18AAAAAO

| | |
|---|---|
| VPREB1 | CD57 |
| VPS13B | CD8 T cells |
| VPS33B | Testis |
| VPS45 | pineal day |
| VPS53 | Skin |
| VSIG4 | Lung |
| VSX1 | Superior Cervical Ganglion |
| VTCN1 | Trachea |
| WARS2 | X721 B lymphoblasts |
| WASL | Colon |
| WDR18 | X721 B lymphoblasts |
| WDR25 | Lung |
| WDR43 | Lymphoma burkitts Daudi |
| WDR55 | CD4 T cells |
| WDR5B | Superior Cervical Ganglion |
| WDR60 | Testis Intersitial |
| WDR67 | CD56 NK Cells |
| WDR70 | BDCA4 Dentritic Cells |
| WDR78 | Testis Seminiferous Tubule |
| WDR8 | Lymphoma burkitts Raji |
| WDR91 | X721 B lymphoblasts |
| WHSC1L1 | Ovary |
| WHSC2 | Lymphoma burkitts Raji |
| WIPI1 | CD71 Early Erythroid |

FIG. 18AAAAAP

| | |
|---|---|
| WISP1 | Uterus Corpus |
| WISP3 | Superior Cervical Ganglion |
| WNT11 | Uterus Corpus |
| WNT2B | retina |
| WNT3 | Superior Cervical Ganglion |
| WNT4 | Pancreatic Islet |
| WNT5A | Colorectal adenocarcinoma |
| WNT5B | Prostate |
| WNT6 | Colorectal adenocarcinoma |
| WNT7A | Bronchial Epithelial Cells |
| WNT7B | Skeletal Muscle |
| WNT8B | Skin |
| WRNIP1 | Trigeminal Ganglion |
| WT1 | Uterus |
| WWC3 | CD19 Bcells neg. sel. |
| XCL1 | CD56 NK Cells |
| XK | CD71 Early Erythroid |
| XPNPEP2 | Kidney |
| XPO4 | pineal day |
| XPO6 | Whole Blood |
| XPO7 | CD71 Early Erythroid |
| XRCC3 | Colorectal adenocarcinoma |
| YAF2 | Skeletal Muscle |
| YBX2 | Testis |

FIG. 18AAAAAQ

| | |
|---|---|
| YIF1A | Liver |
| YIPF6 | CD71 Early Erythroid |
| YWHAQ | Skeletal Muscle |
| YY2 | Uterus Corpus |
| ZAK | Dorsal Root Ganglion |
| ZAP70 | CD56 NK Cells |
| ZBED4 | Dorsal Root Ganglion |
| ZBTB10 | Superior Cervical Ganglion |
| ZBTB17 | Lymphoma burkitts Raji |
| ZBTB24 | Skin |
| ZBTB3 | Superior Cervical Ganglion |
| ZBTB33 | Superior Cervical Ganglion |
| ZBTB40 | CD4 T cells |
| ZBTB43 | CD33 Myeloid |
| ZBTB5 | CD19 Bcells neg. sel. |
| ZBTB6 | Superior Cervical Ganglion |
| ZBTB7B | Ovary |
| ZC3H12A | Smooth Muscle |
| ZC3H14 | Testis Interstitial |
| ZCCHC2 | Salivary gland |
| ZCWPW1 | Testis Germ Cell |
| ZDHHC13 | X721 B lymphoblasts |
| ZDHHC14 | Lymphoma burkitts Raji |
| ZDHHC18 | Whole Blood |

FIG. 18AAAAAR

| | |
|---|---|
| ZDHHC3 | Testis Interstitial |
| ZER1 | CD71 Early Erythroid |
| ZFHX4 | Smooth Muscle |
| ZFP2 | Superior Cervical Ganglion |
| ZFP30 | Ciliary Ganglion |
| ZFPM2 | Cerebellum |
| ZFR2 | Trigeminal Ganglion |
| ZFYVE9 | Cingulate Cortex |
| ZG16 | Colon |
| ZGPAT | Liver |
| ZIC3 | Cerebellum |
| ZKSCAN1 | Pancreas |
| ZKSCAN5 | CD19 Bcells neg. sel. |
| ZMAT5 | Liver |
| ZMYM1 | Superior Cervical Ganglion |
| ZMYND10 | Testis |
| ZNF124 | Uterus Corpus |
| ZNF132 | Skin |
| ZNF133 | CD58 |
| ZNF135 | CD59 |
| ZNF136 | CD8 T cells |
| ZNF14 | Trigeminal Ganglion |
| ZNF140 | Superior Cervical Ganglion |
| ZNF157 | Trigeminal Ganglion |

FIG. 18AAAAAS

| | |
|---|---|
| ZNF167 | Appendix |
| ZNF175 | Leukemia chronic Myelogenous K601 |
| ZNF177 | Testis Seminiferous Tubule |
| ZNF185 | Tongue |
| ZNF193 | Ovary |
| ZNF200 | Whole Blood |
| ZNF208 | Liver |
| ZNF214 | Superior Cervical Ganglion |
| ZNF215 | Dorsal Root Ganglion |
| ZNF223 | Ciliary Ganglion |
| ZNF224 | CD8 T cells |
| ZNF226 | pineal night |
| ZNF23 | CD71 Early Erythroid |
| ZNF235 | Superior Cervical Ganglion |
| ZNF239 | Testis Seminiferous Tubule |
| ZNF250 | Skin |
| ZNF253 | Superior Cervical Ganglion |
| ZNF259 | Testis |
| ZNF264 | CD4 T cells |
| ZNF267 | Whole Blood |
| ZNF273 | Skin |
| ZNF274 | CD19 Bcells neg. sel. |
| ZNF280B | Testis Intersitial |

FIG. 18AAAAAT

| | |
|---|---|
| ZNF286A | Superior Cervical Ganglion |
| ZNF304 | Superior Cervical Ganglion |
| ZNF318 | X721 B lymphoblasts |
| ZNF323 | Superior Cervical Ganglion |
| ZNF324 | Thymus |
| ZNF331 | Adrenal Cortex |
| ZNF34 | Fetal Thyroid |
| ZNF343 | Ciliary Ganglion |
| ZNF345 | Superior Cervical Ganglion |
| ZNF362 | Atrioventricular Node |
| ZNF385D | Superior Cervical Ganglion |
| ZNF391 | Testis Intersitial |
| ZNF415 | Testis Intersitial |
| ZNF430 | CD8 T cells |
| ZNF434 | Globus Pallidus |
| ZNF443 | Trigeminal Ganglion |
| ZNF446 | Superior Cervical Ganglion |
| ZNF45 | CD60 |
| ZNF451 | CD71 Early Erythroid |
| ZNF460 | Trigeminal Ganglion |
| ZNF467 | Whole Blood |
| ZNF468 | CD56 NK Cells |
| ZNF471 | Skeletal Muscle |
| ZNF484 | Atrioventricular Node |

FIG. 18AAAAAU

| | |
|---|---|
| ZNF507 | Fetal liver |
| ZNF510 | Appendix |
| ZNF516 | Uterus |
| ZNF550 | Temporal Lobe |
| ZNF556 | Ciliary Ganglion |
| ZNF557 | Ciliary Ganglion |
| ZNF587 | Superior Cervical Ganglion |
| ZNF589 | Superior Cervical Ganglion |
| ZNF606 | Fetal brain |
| ZNF672 | CD71 Early Erythroid |
| ZNF696 | Trigeminal Ganglion |
| ZNF7 | Skeletal Muscle |
| ZNF711 | Testis Germ Cell |
| ZNF717 | Appendix |
| ZNF74 | Dorsal Root Ganglion |
| ZNF770 | Skeletal Muscle |
| ZNF771 | Atrioventricular Node |
| ZNF780A | Superior Cervical Ganglion |
| ZNF79 | Leukemia lymphoblastic MOLT 41 |
| ZNF8 | Superior Cervical Ganglion |
| ZNF80 | Trigeminal Ganglion |
| ZNF804A | Lymphoma burkitts Daudi |
| ZNF821 | Testis Intersitial |

FIG. 18AAAAAV

| | |
|---|---|
| ZNHIT2 | Testis |
| ZP2 | Cerebellum |
| ZPBP | Testis Intersitial |
| ZSCAN16 | CD19 Bcells neg. sel. |
| ZSCAN2 | Skeletal Muscle |
| ZSWIM1 | Ciliary Ganglion |
| ZW10 | Superior Cervical Ganglion |
| ZXDB | Ciliary Ganglion |
| ZZZ3 | CD61 | ent application Ser. No. 17/497,358, filed Oct. 8, 2021, which is

METHODS FOR PROFILING AND QUANTITATING CELL-FREE RNA

CROSS REFERENCE

This application claims benefit and is a Continuation of application Ser. No. 17/497,358, filed Oct. 8, 2021, which is a Continuation of application Ser. No. 17/187,298, filed Feb. 26, 2021, which is a Continuation of application Ser. No. 16/373,996, filed Apr. 3, 2019, now abandon, which is a Continuation of application Ser. No. 15/377,894 filed Dec. 13, 2016, now U.S. Pat. No. 10,287,632 issued May 14, 2019, which is a Continuation of application Ser. No. 14/861,650 filed Sep. 22, 2015, now U.S. Pat. No. 10,240,200 issued Mar. 26, 2019, which is a Divisional of application Ser. No. 13/752,131 filed Jan. 28, 2013, now abandon, which claims benefit of U.S. Provisional Patent Application No. 61/591,642, filed on Jan. 27, 2012, which applications are incorporated herein by reference in their entirety.

TECHNICAL FIELD

The present invention relates the field of nucleic acid analysis from a biological sample containing genetic material. Specifically, methods of the invention relate to quantitating tissue-specific nucleic acids in a biological sample.

BACKGROUND

It is often challenging to gauge the health of organs within an individual's body. Physicians are often forced to use expensive imaging techniques or perform invasive biopsies for cancer screening to identify diagnostic biomarkers and monitor tumor initiation and progression. The invasive nature of biopsies makes them unsuitable for widespread screening of patients. In addition, many diagnostic biomarkers are only identified in cancer cell lines or from biopsy specimens obtained from patients with late-stage disease and metastasis.

The presence of circulating nucleic acids (DNA and RNA) detectable in the plasma and serum of cancer patients has been investigated for its potential use to serve as markers for diagnostic purposes, with the obvious benefit being a non-invasive diagnostic tool. It has been shown that markers within the plasma are identical to the ones found in the carcinogenic tissue of the patient. Circulating RNA is particularly of interest for use in early detection cancer screenings due to RNA markers close association with malignancy.

In addition to cancer detection, the discovery of fetal specific cell-free RNA present in maternal plasma has opened up new horizons on prenatal molecular diagnostics (see e.g., Poon et al., Clinical Chemistry, 46(11): 1832-1834 (2000)). Specifically, analysis of plasma RNA holds promise for noninvasive gene expression profiling of the fetus. However, only a handful of pregnancy specific cell-free RNA transcripts have been characterized to date. A comprehensive profiling of such RNA has not been performed.

A problem with analyzing cell-free RNA in non-maternal and maternal blood is the lack of suitable data to estimate the biological causes of the cell-free RNA present. For example, there lacks a reliable method for determining tissue origins of the cell-free RNA present in blood.

SUMMARY

The present invention provides methods for profiling the origin of the cell-free RNA to assess the health of an organ or tissue. Deviations in normal cell-free transcriptomes are caused when organ/tissue-specific transcripts are released in to the blood in large amounts as those organs/tissue begin to fail or are attacked by the immune system or pathogens. As a result inflammation process can occur as part of body's complex biological response to these harmful stimuli. The invention, according to certain aspects, utilizes tissue-specific RNA transcripts of healthy individuals to deduce the relative optimal contributions of different tissues in the normal cell-free transcriptome, with each tissue-specific RNA transcript of the sample being indicative of the apotopic rate of that tissue. The normal cell-free transcriptome serves as a baseline or reference level to assess tissue health of other individuals. The invention includes a comparative measurement of the cell-free transcriptome of a sample to the normal cell free transcriptome to assess the sample levels of tissue-specific transcripts circulating in plasma and to assess the health of tissues contributing to the cell-free transcriptome.

In addition to normal reference levels, methods of the invention also utilize reference levels for cell-free transcriptomes specific to other patient populations. Using methods of the invention one can determine the relative contribution of tissue-specific transcripts to the cell-free transcriptome of maternal subjects, fetus subjects, and/or subjects having a condition or disease.

By analyzing the health of tissue based on tissue-specific transcripts, methods of the invention advantageously allow one to assess the health of a tissue without relying on disease-related protein biomarkers. In certain aspects, methods of the invention assess the health of a tissue by comparing a sample level of RNA in a biological sample to a reference level of RNA specific to a tissue, determining whether a difference exists between the sample level and the reference level, and characterizing the tissue as abnormal if a difference is detected. For example, if a patient's RNA expression levels for a specific tissue differs from the RNA expression levels for the specific tissue in the normal cell-free transcriptome, this indicates that patient's tissue is not functioning properly.

In certain aspects, methods of the invention involve assessing health of a tissue by characterizing the tissue as abnormal if a specified level of RNA is present in the blood. The method may further include detecting a level of RNA in a blood sample, comparing the sample level of RNA to a reference level of RNA specific to a tissue, determining whether a difference exists between the sample level and the reference level, and characterizing the tissue as abnormal if the sample level and the reference level are the same.

The present invention also provides methods for comprehensively profiling fetal specific cell-free RNA in maternal plasma and deconvoluting the cell-free transcriptome of fetal origin with relative proportion to different fetal tissue types. Methods of the invention involve the use of next-generation sequencing technology and/or microarrays to characterize the cell-free RNA transcripts that are present in maternal plasma at different stages of pregnancy. Quantification of these transcripts allows one to deduce changes of these genes across different trimesters, and hence provides a way of quantification of temporal changes in transcripts.

Methods of the invention allow diagnosis and identification of the potential for complications during or after pregnancy. Methods also allow the identification of pregnancy-associated transcripts which, in turn, elucidates maternal and fetal developmental programs. Methods of the invention are useful for preterm diagnosis as well as elucidation of transcript profiles associated with fetal developmental pathways generally. Thus, methods of the invention are useful to characterize fetal development and are not limited to characterization only of disease states or complications associated with pregnancy. Exemplary embodiments of the methods are described in the detailed description, claims, and figures provided below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 depicts a listing of the top detected female pregnancy associated differentially expressed transcripts.

FIG. 4 depicts a ranking of the top 20 transcripts differentially expressed between pre-term and normal pregnancy.

FIG. 7A-7B outlines exemplary process steps for determining the relative tissue contributions to a cell-free transcriptome of a sample.

FIG. 8A-8B depicts the panel of selected fetal tissue-specific transcripts generated in Example 2.

FIG. 10A-10B illustrates relative expression of placental genes across maternal time points (first trimester, second trimester, third trimester, and post partum).

FIG. 13 illustrates the relative composition of different organs contribution towards a plasma adult cell free transcriptome.

FIG. 14 illustrates a decomposition of decomposition of organ contribution towards a plasma adult cell free transcriptome using RNA-seq data.

FIG. 15A-15D depicts a panel of 94 tissue-specific genes in Example 3 that were verified with qPCR.

FIG. 18A-18AAAAAV depicts a list of tissue-specific genes for Example 3 that was obtained using raw data from the Human U133A/GNF1H Gene Atlas and RNA-Seq Atlas databases.

DETAILED DESCRIPTION

Methods and materials described herein apply a combination of next-generation sequencing and microarray techniques for detecting, quantitating and characterizing RNA sequences present in a biological sample. In certain embodiments, the biological sample contains a mixture of genetic material from different genomic sources, i.e. pregnant female and a fetus.

Unlike other methods of digital analysis in which the nucleic acid in the sample is isolated to a nominal single target molecule in a small reaction volume, methods of the present invention are conducted without diluting or distributing the genetic material in the sample. Methods of the invention allow for simultaneous screening of multiple transcriptomes, and provide informative sequence information for each transcript at the single-nucleotide level, thus providing the capability for non-invasive, high throughput screening for a broad spectrum of diseases or conditions in a subject from a limited amount of biological sample.

In one particular embodiment, methods of the invention involve analysis of mixed fetal and maternal RNA in the maternal blood to identify differentially expressed transcripts throughout different stages of pregnancy that may be indicative of a preterm or pathological pregnancy. Differential detection of transcripts is achieved, in part, by isolating and amplifying plasma RNA from the maternal blood throughout the different stages of pregnancy, and quantitating and characterizing the isolated transcripts via microarray and RNA-Seq.

Methods and materials specific for analyzing a biological sample containing RNA (including non-maternal, maternal, maternal-fetus mixed) as described herein, are merely one example of how methods of the invention can be applied and are not intended to limit the invention. Methods of the invention are also useful to screen for the differential expression of target genes related to cancer diagnosis, progression and/or prognosis using cell-free RNA in blood, stool, sputum, urine, transvaginal fluid, breast nipple aspirate, cerebrospinal fluid, etc.

In certain embodiments, methods of the invention generally include the following steps: obtaining a biological sample containing genetic material from different genomic sources, isolating total RNA from the biological sample containing biological sample containing a mixture of genetic material from different genomic sources, preparing amplified cDNA from total RNA, sequencing amplified cDNA, and digital counting and analysis, and profiling the amplified cDNA.

Figure 17:
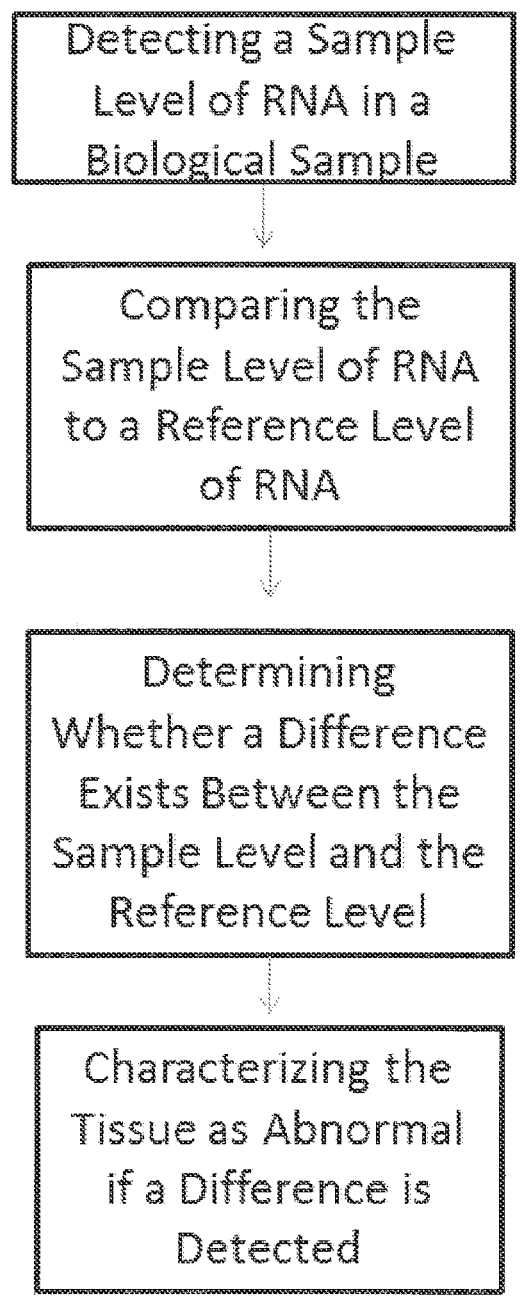
FIG. 17 depicts a flow-diagram of this method according to certain embodiments.

Methods of the invention also involve assessing the health of a tissue contributing to the cell-free transcriptome. In certain embodiments, the invention involves assessing the cell-free transcriptome of a biological sample to determine tissue-specific contributions of individual tissues to the cell-free transcriptome. According to certain aspects, the invention assesses the health of a tissue by detecting a sample level of RNA in a biological sample, comparing the sample level of RNA to a reference level of RNA specific to the tissue, and characterizing the tissue as abnormal if a difference is detected. This method is applicable to characterize the health of a tissue in non-maternal subjects, pregnant subjects, and live fetuses. FIG. 17 depicts a flow-diagram of this method according to certain embodiments.

In certain aspects, methods of the invention employ a deconvolution of a reference cell-free RNA transcriptome to determine a reference level for a tissue. Preferably, the reference cell-free RNA transcriptome is a normal, healthy transcriptome, and the reference level of a tissue is a relative level of RNA specific to the tissue present in the blood of healthy, normal individuals. Methods of the invention assume that apoptotic cells from different tissue types release their RNA into plasma of a subject. Each of these tissues expresses a specific number of genes unique to the tissue type, and the cell-free RNA transcriptome of a subject is a summation of the different tissue types. Each tissue may express one or more numbers of genes. In certain embodiments, the reference level is a level associated with one of the genes expressed by a certain tissue. In other embodiments, the reference level is a level associated with a plurality of genes expressed by a certain tissue. It should be noted that a reference level or threshold amount for a tissue-specific transcript present in circulating RNA may be zero or a positive number.

For healthy, normal subjects, the relative contributions of circulating RNA from different tissue types are relatively stable, and each tissue-specific RNA transcript of the cell-free RNA transcriptome for normal subjects can serve as a reference level for that tissue. Applying methods of the invention, a tissue is characterized as unhealthy or abnormal if a sample includes a level of RNA that differs from a reference level of RNA specific to the tissue. The tissue of the sample may be characterized as unhealthy if the actual level of RNA is statistically different from the reference level. Statistical significance can be determined by any method known in the art. These measurements can be used to screen for organ health, as diagnostic tool, and as a tool to measure response to pharmaceuticals or in clinical trials to monitor health.

If a difference is detected between the sample level of RNA and the reference level of RNA, such difference suggests that the associated tissue is not functioning properly. The change in circulating RNA may be the precursor to organ failure or indicate that the tissue is being attacked by the immune system or pathogens. If a tissue is identified as abnormal, the next step(s), according to certain embodiments, may include more extensive testing of the tissue (e.g. invasive biopsy of the tissue), prescribing course of treatment specific to the tissue, and/or routine monitoring of the tissue.

Methods of the invention can be used to infer organ health non-invasively. This non-invasive testing can be used to screen for appendicitis, incipient diabetes and pathological conditions induced by diabetes such as nephropathy, neuropathy, retinopathy etc. In addition, the invention can be used to determine the presence of graft versus host disease in organ transplants, particularly in bone marrow transplant recipients whose new immune system is attacking the skin, GI tract or liver. The invention can also be used to monitor the health of solid organ transplant recipients such as heart, lung and kidney. The methods of the invention can assess likelihood of prematurity, preeclampsia and anomalies in pregnancy and fetal development. In addition, methods of the invention could be used to identify and monitor neurological disorders (e.g. multiple sclerosis and Alzheimer's disease) that involve cell specific death (e.g. of neurons or due to demyelination) or that involve the generation of plaques or protein aggregation.

A cell-free transcriptome for purposes of determining a reference level for tissue-specific transcripts can be the cell-free transcriptome of one or more normal subjects, maternal subjects, subjects having a certain conditions and diseases, or fetus subjects. In the case of certain conditions, the reference level of a tissue is a level of RNA specific to the tissue present in blood of one or more subjects having a certain disease or condition. In such aspect, the method includes detecting a level of RNA in a blood, comparing the sample level of RNA to a reference level of RNA specific to a tissue, determining whether a difference exists between the sample level and the reference level, and characterizing the as abnormal if the sample level and the reference level are the same.

A deconvolution of a cell-free transcriptome is used to determine the relative contribution of each tissue type towards the cell-free RNA transcriptome. The following steps are employed to determine the relative RNA contributions of certain tissues in a sample. First, a panel of tissue-specific transcripts is identified. Second, total RNA in plasma from a sample is determined using methods known in the art. Third, the total RNA is assessed against the panel of tissue-specific transcripts, and the total RNA is considered a summation these different tissue-specific transcripts. Quadratic programming can be used as a constrained optimization method to deduce the relative optimal contributions of different organs/tissues towards the cell-free transcriptome of the sample.

One or more databases of genetic information can be used to identify a panel of tissue-specific transcripts. Accordingly, aspects of the invention provide systems and methods for the use and development of a database. Particularly, methods of the invention utilize databases containing existing data generated across tissue types to identify the tissue-specific genes. Databases utilized for identification of tissue-specific genes include the Human 133A/GNF1H Gene Atlas and RNA-Seq Atlas, although any other database or literature can be used. In order to identify tissue-specific transcripts from one or more databases, certain embodiments employ a template-matching algorithm to the databases. Template matching algorithms used to filter data are known in the art, see e.g., Pavlidis P, Noble W S (2001) Analysis of strain and regional variation in gene expression in mouse brain. *Genome Biol* 2:research0042.1-0042.15.

In certain embodiments, quadratic programming is used as a constrained optimization method to deduce relative optimal contributions of different organs/tissues towards the cell-free transcriptome in a sample. Quadratic programming is known in the art and described in detail in Goldfarb and A. Idnani (1982). Dual and Primal-Dual Methods for Solving Strictly Convex Quadratic Programs. In J. P. Hennart (ed.), Numerical Analysis, Springer-Verlag, Berlin, pages 226-239, and D. Goldfarb and A. Idnani (1983). A numerically stable dual method for solving strictly convex quadratic programs. Mathematical Programming, 27, 1-33.

Figure 7B:
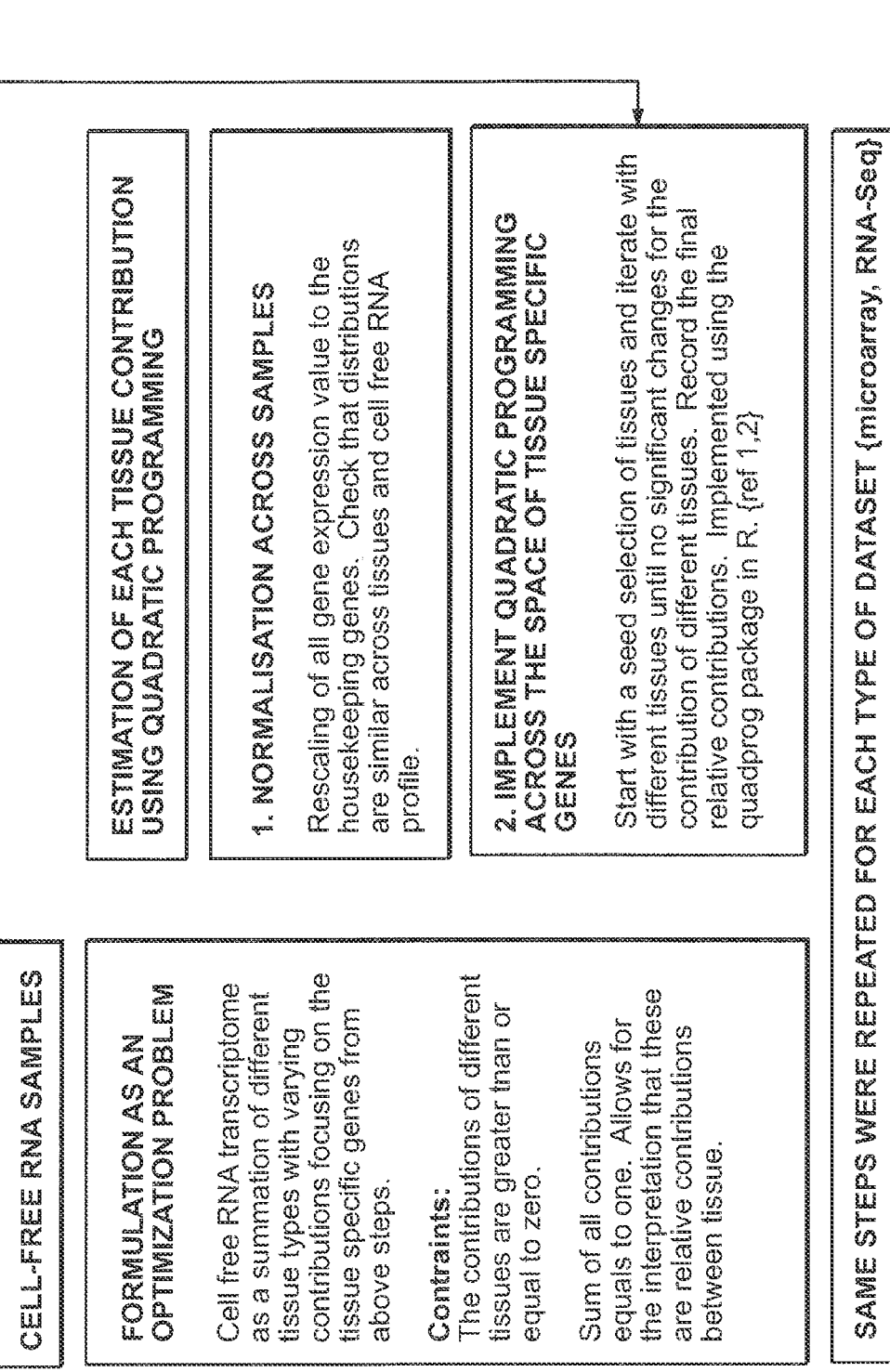

FIG. 7 outlines exemplary process steps for determining the relative tissue contributions to a cell-free transcriptome of a sample. Using information provided by one or more tissue-specific databases, a panel of tissue-specific genes is generated with a template-matching function. A quality control function can be applied to filter the results. A blood sample is then analyzed to determine the relative contribution of each tissue-specific transcript to the total RNA of the sample. Cell-free RNA is extracted from the sample, and the cell-free RNA extractions are processed using one or more quantification techniques (e.g. standard microarrays and RNA-sequence protocols). The obtained gene expression values for the sample are then normalized. This involves rescaling of all gene expression values to the housekeeping genes. Next, the sample's total RNA is assessed against the panel of tissue-specific genes using quadratic programming in order to determine the tissue-specific relative contributions to the sample's cell-free transcriptome. The following constraints are employed to obtain the estimated relative contributions during the quadratic programming analysis: a) the RNA contributions of different tissues are greater than or equal to zero, and b) the sum of all contributions to the cell-free transcriptome equals one.

Method of the invention for determining the relative contributions for each tissue can be used to determine the reference level for the tissue. That is, a certain population of subjects (e.g., maternal, normal, and cancerous) can be subject to the deconvolution process outlined in FIG. 7 to obtain reference levels of tissue-specific gene expression for that patient population. When relative tissue contributions are considered individually, quantification of each of these tissue-specific transcripts can be used as a measure for the reference apoptotic rate of that particular tissue for that particular population. For example, blood from one or more healthy, normal individuals can be analyzed to determine the relative RNA contribution of tissues to the cell-free RNA transcriptome for healthy, normal individuals. Each relative RNA contribution of tissue that makes up the normal RNA transcriptome is a reference level for that tissue.

According to certain embodiments, an unknown sample of blood can be subject to process outlined in FIG. 7 to determine the relative tissue contributions to the cell-free RNA transcriptome of that sample. The relative tissue contributions of the sample are then compared to one or more reference levels of the relative contributions to a reference cell-free RNA transcriptome. If a specific tissue shows a contribution to the cell-free RNA transcriptome in the sample that is greater or less than the contribution of the specific tissue in reference cell-free RNA transcriptome, then the tissue exhibiting differential contribution may be characterized accordingly. If the reference cell-free transcriptome represents a healthy population, a tissue exhibiting a differential RNA contribution in a sample cell-free transcriptome can be classified as unhealthy.

The biological sample can be blood, saliva, sputum, urine, semen, transvaginal fluid, cerebrospinal fluid, sweat, breast milk, breast fluid (e.g., breast nipple aspirate), stool, a cell or a tissue biopsy. In certain embodiments, the samples of the same biological sample are obtained at multiple different time points in order to analyze differential transcript levels in the biological sample over time. For example, maternal plasma may be analyzed in each trimester. In some embodiments, the biological sample is drawn blood and circulating nucleic acids, such as cell-free RNA. The cell-free RNA may be from different genomic sources is found in the blood or plasma, rather than in cells.

In a particular embodiment, the drawn blood is maternal blood. In order to obtain a sufficient amount of nucleic acids for testing, it is preferred that approximately 10-50 mL of blood be drawn. However, less blood may be drawn for a genetic screen in which less statistical significance is required, or in which the RNA sample is enriched for fetal RNA.

Methods of the invention involve isolating total RNA from a biological sample. Total RNA can be isolated from the biological sample using any methods known in the art. In certain embodiments, total RNA is extracted from plasma. Plasma RNA extraction is described in Enders et al., "The Concentration of Circulating Corticotropin-releasing Hormone mRNA in Maternal Plasma Is Increased in Preeclampsia," Clinical Chemistry 49: 727-731, 2003. As described there, plasma harvested after centrifugation steps is mixed Trizol LS reagent (Invitrogen) and chloroform. The mixture is centrifuged, and the aqueous layer transferred to new tubes. Ethanol is added to the aqueous layer. The mixture is then applied to an RNeasy mini column (Qiagen) and processed according to the manufacturer's recommendations.

In the embodiments where the biological sample is maternal blood, the maternal blood may optionally be processed to enrich the fetal RNA concentration in the total RNA. For example, after extraction, the RNA can be separated by gel electrophoresis and the gel fraction containing circulatory RNA with a size of corresponding to fetal RNA (e.g., <300 bp) is carefully excised. The RNA is extracted from this gel slice and eluted using methods known in the art.

Alternatively, fetal specific RNA may be concentrated by known methods, including centrifugation and various enzyme inhibitors. The RNA is bound to a selective membrane (e.g., silica) to separate it from contaminants. The RNA is preferably enriched for fragments circulating in the plasma, which are less than less 300 bp. This size selection is done on an RNA size separation medium, such as an electrophoretic gel or chromatography material.

Flow cytometry techniques can also be used to enrich for fetal cells in maternal blood (Herzenberg et al., PNAS 76: 1453-1455 (1979); Bianchi et al., PNAS 87: 3279-3283 (1990); Bruch et al., Prenatal Diagnosis 11: 787-798 (1991)). U.S. Pat. No. 5,432,054 also describes a technique for separation of fetal nucleated red blood cells, using a tube having a wide top and a narrow, capillary bottom made of polyethylene. Centrifugation using a variable speed program results in a stacking of red blood cells in the capillary based on the density of the molecules. The density fraction containing low-density red blood cells, including fetal red blood cells, is recovered and then differentially hemolyzed to preferentially destroy maternal red blood cells. A density gradient in a hypertonic medium is used to separate red blood cells, now enriched in the fetal red blood cells from lymphocytes and ruptured maternal cells. The use of a hypertonic solution shrinks the red blood cells, which increases their density, and facilitates purification from the more dense lymphocytes. After the fetal cells have been isolated, fetal RNA can be purified using standard techniques in the art.

Further, an agent that stabilizes cell membranes may be added to the maternal blood to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, *Ginkgo biloba* extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

An example of a protocol for using this agent is as follows: The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Methods of the invention also involve preparing amplified cDNA from total RNA. cDNA is prepared and indiscriminately amplified without diluting the isolated RNA sample or distributing the mixture of genetic material in the isolated RNA into discrete reaction samples. Preferably, amplification is initiated at the 3' end as well as randomly throughout the whole transcriptome in the sample to allow for amplification of both mRNA and non-polyadenylated transcripts. The double-stranded cDNA amplification products are thus optimized for the generation of sequencing libraries for Next Generation Sequencing platforms. Suitable kits for amplifying cDNA in accordance with the methods of the invention include, for example, the Ovation® RNA-Seq System.

Methods of the invention also involve sequencing the amplified cDNA. While any known sequencing method can be used to sequence the amplified cDNA mixture, single molecule sequencing methods are preferred. Preferably, the amplified cDNA is sequenced by whole transcriptome shotgun sequencing (also referred to herein as ("RNA-Seq"). Whole transcriptome shotgun sequencing (RNA-Seq) can be accomplished using a variety of next-generation sequencing platforms such as the Illumina Genome Analyzer platform, ABI Solid Sequencing platform, or Life Science's 454 Sequencing platform.

Methods of the invention further involve subjecting the cDNA to digital counting and analysis. The number of amplified sequences for each transcript in the amplified sample can be quantitated via sequence reads (one read per amplified strand). Unlike previous methods of digital analysis, sequencing allows for the detection and quantitation at the single nucleotide level for each transcript present in a biological sample containing a genetic material from different genomic sources and therefore multiple transcriptomes.

After digital counting, the ratios of the various amplified transcripts can compared to determine relative amounts of differential transcript in the biological sample. Where multiple biological samples are obtained at different time-points, the differential transcript levels can be characterized over the course of time.

Differential transcript levels within the biological sample can also be analyzed using via microarray techniques. The amplified cDNA can be used to probe a microarray containing gene transcripts associated with one or conditions or diseases, such as any prenatal condition, or any type of cancer, inflammatory, or autoimmune disease.

It will be understood that methods and any flow diagrams disclosed herein can be implemented by computer program instructions. These program instructions may be provided to a computer processor, such that the instructions, which execute on the processor, create means for implementing the actions specified in the flowchart blocks or described in methods for assessing tissue disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

The computer program instructions can be, stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

EXAMPLES

Example 1: Profiling Maternal Plasma Cell-Free RNA by RNA Sequencing—A Comprehensive Approach Overview:

The plasma RNA profiles of 5 pregnant women were collected during the first trimester, second trimester, post-partum, as well as those of 2 non-pregnant female donors and 2 male donors using both microarray and RNA-Seq.

Among these pregnancies, there were 2 pregnancies with clinical complications such as premature birth and one pregnancy with bi-lobed placenta. Comparison of these pregnancies against normal cases reveals genes that exhibit significantly different gene expression pattern across different temporal stages of pregnancy. Application of such technique to samples associated with complicated pregnancies may help identify transcripts that can be used as molecular markers that are predictive of these pathologies.

Study Design and Methods:

Subjects

Samples were collected from 5 pregnant women were during the first trimester, second trimester, third trimester, and post-partum. As a control, blood plasma samples were also collected from 2 non-pregnant female donors and 2 male donors.

Blood Collection and Processing

Blood samples were collected in EDTA tube and centrifuged at 1600 g for 10 min at 4° C. Supernatant were placed in 1 ml aliquots in a 1.5 ml microcentrifuge tube which were then centrifuged at 16000 g for 10 min at 4° C. to remove residual cells. Supernatants were then stored in 1.5 ml microcentrifuge tubes at −80° C. until use.

RNA Extraction and Amplification

The cell-free maternal plasma RNAs was extracted by Trizol LS reagent. The extracted and purified total RNA was converted to cDNA and amplified using the RNA-Seq Ovation Kit (NuGen). (The above steps were the same for both Microarray and RNA-Seq sample preparation).

The cDNA was fragmented using DNase I and labeled with Biotin, following by hybridization to Affymetrix GeneChip ST 1.0 microarrays. The Illumina sequencing platform and standard Illumina library preparation protocols were used for sequencing.

Data Analysis:

Correlation Between Microarray and RNA-Seq

The RMA algorithm was applied to process the raw microarray data for background correction and normalization. RPKM values of the sequenced transcripts were obtained using the CASAVA 1.7 pipeline for RNA-seq. The RPKM in the RNA-Seq and the probe intensities in the microarray were converted to log 2 scale. For the RNA-Seq data, to avoid taking the log of 0, the gene expressions with RPKM of 0 were set to 0.01 prior to taking logs. Correlation coefficients between these two platforms ranges were then calculated.

Differential Expression of RNA Transcripts Levels Using RNA-Seq

Differential gene expression analysis was performed using edgeR, a set of library functions which are specifically written to analyze digital gene expression data. Gene Ontology was then performed using DAVID to identify for significantly enriched GO terms.

Principle Component Analysis & Identification of Significant Time Varying Genes

Principle component analysis was carried out using a custom script in R. To identify time varying genes, the time course library of functions in R were used to implement empirical Bayes methods for assessing differential expression in experiments involving time course which in our case are the different trimesters and post-partum for each individual patients.

Results and Discussion

RNA-Seq Reveals that Pregnancy-Associated Transcripts are Detected at Significantly Different Levels Between Pregnant and Non-Pregnant Subjects.

A comparison of the transcripts level derived using RNA-Seq and Gene Ontology Analysis between pregnant and non-pregnant subjects revealed that transcripts exhibiting differential transcript levels are significantly associated with female pregnancy, suggesting that RNA-Seq are enabling observation of real differences between these two class of transcriptome due to pregnancy. The top rank significantly expressed gene is PLAC4 which has also been known as a target in previous studies for developing RNA based test for trisomy 21. A listing of the top detected female pregnancy associated differentially expressed transcripts is shown in FIG. 1.

Principle Component Analysis (PCA) on Plasma Cell Free RNA Transcripts Levels in Maternal Plasma Distinguishes Between Pre-Mature and Normal Pregnancy Using the plasma cell free transcript level profiles as inputs for Principle Component Analysis, the profile from each patient at different time points clustered into different pathological clusters suggesting that cell free plasma RNA transcript profile in maternal plasma may be used to distinguish between pre-term and non-preterm pregnancy.

Figure 2:
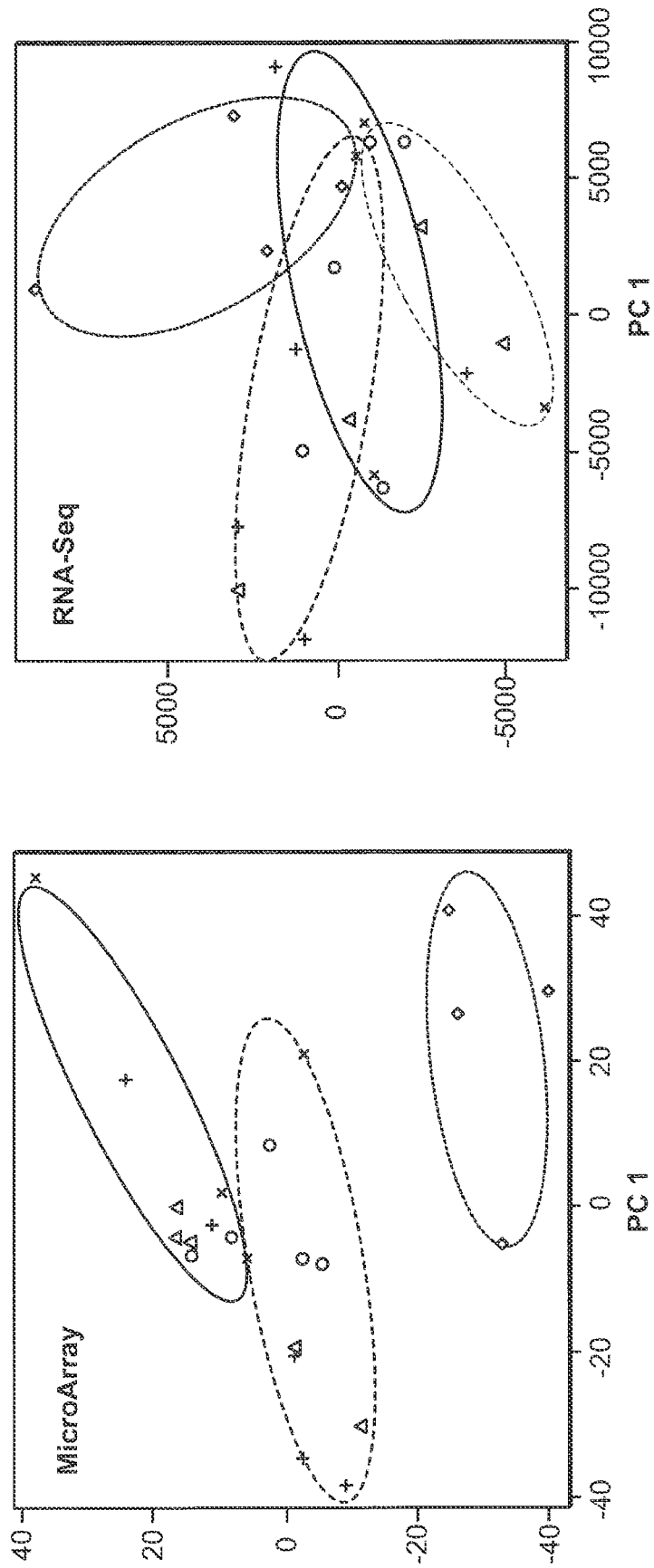
FIG. 2 shows plots of the two main principal components for cell free RNA transcript levels obtained in Example 1.

Plasma Cell free RNA levels were quantified using both microarray and RNA-Seq. Transcripts expression levels profile from microarray and RNA-Seq from each patient are correlated with a Pearson correlation of approximately 0.7. Plots of the two main principal components for cell free RNA transcript levels is shown in FIG. 2.

Figure 3A:
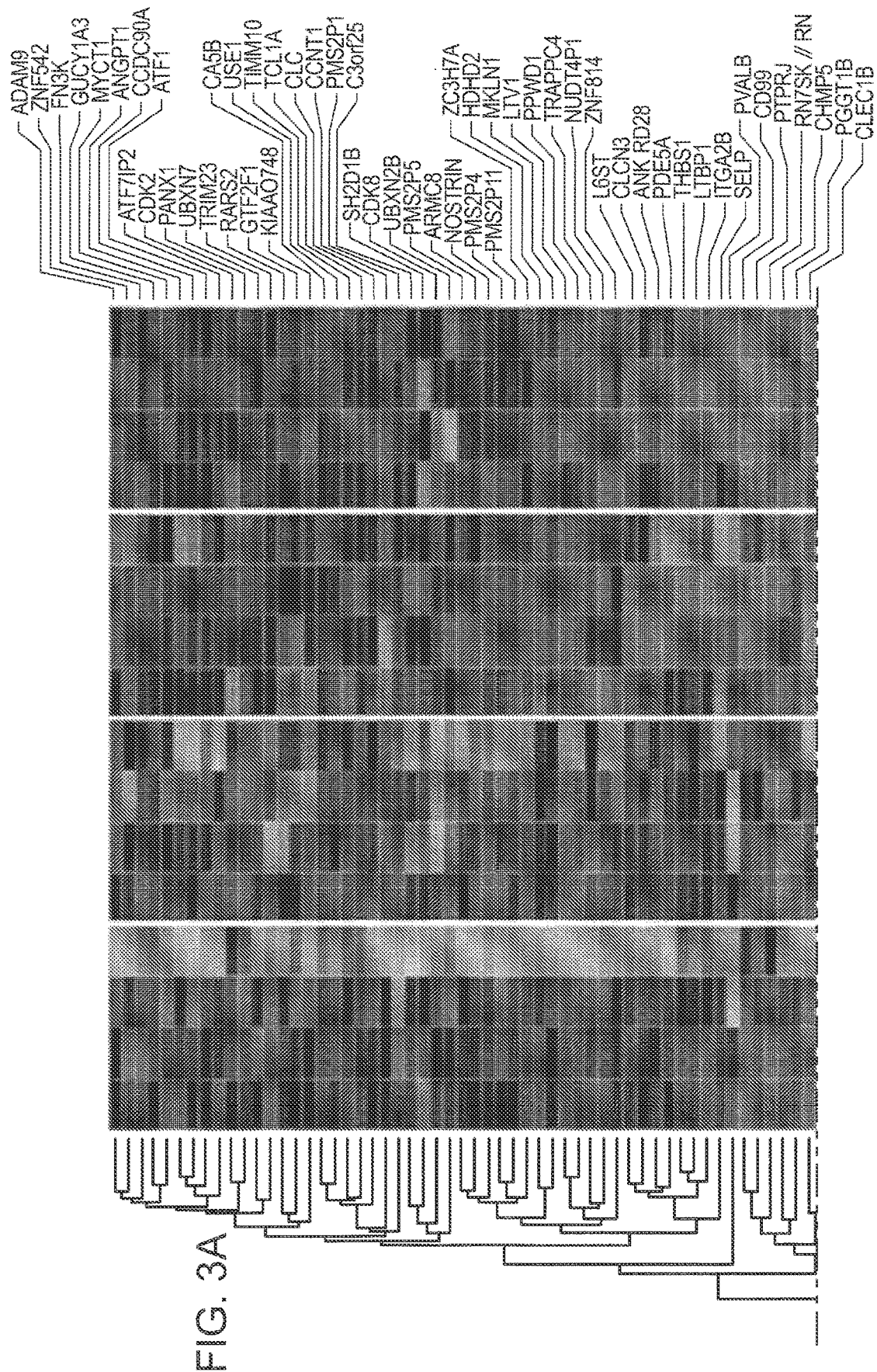
FIG. 3A-3B depicts a heatmap of the top 100 cell free transcript levels exhibiting different temporal levels in pre-term and normal pregnancy using microarrays.
Figure 3B:
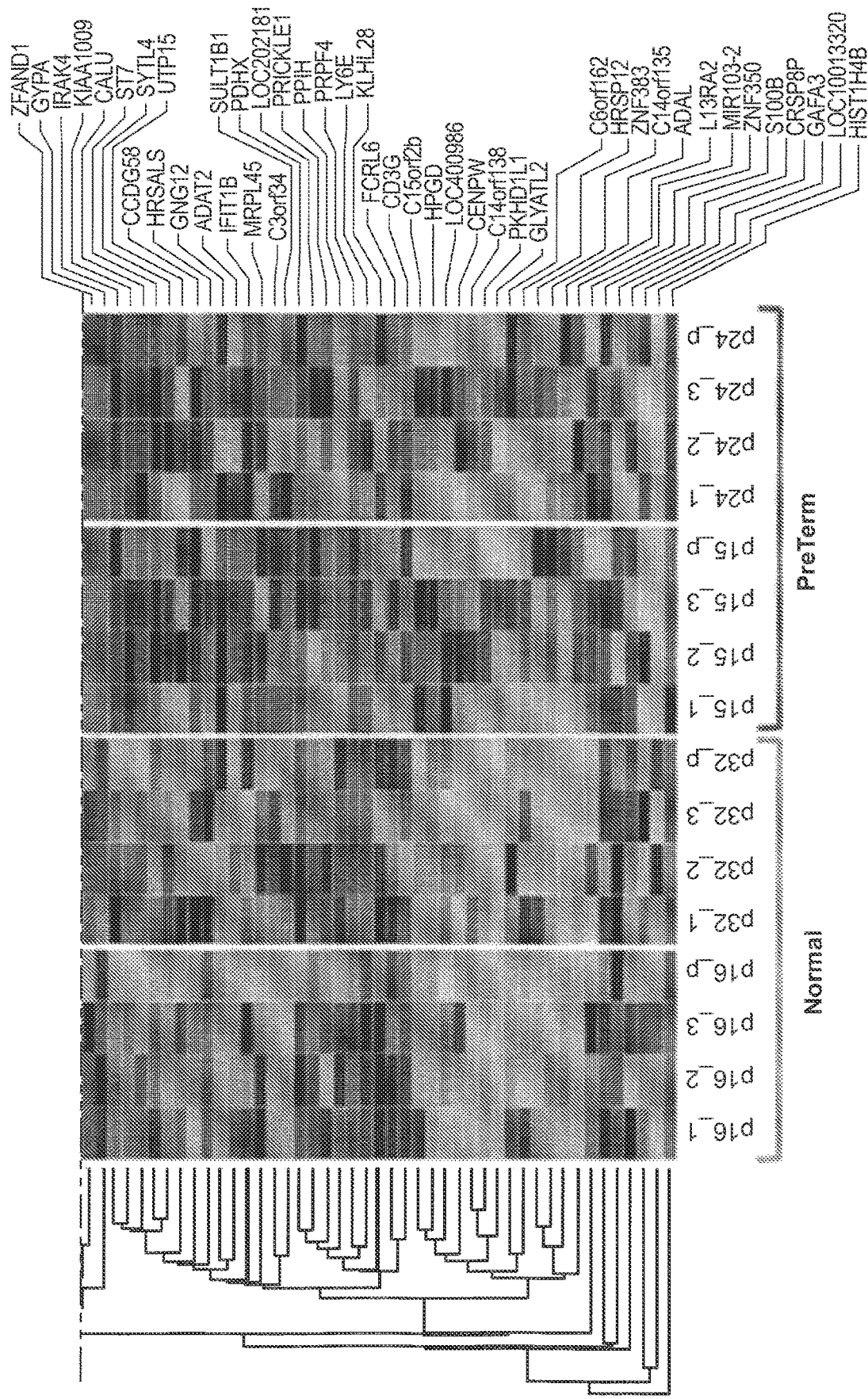
Figure 3C:
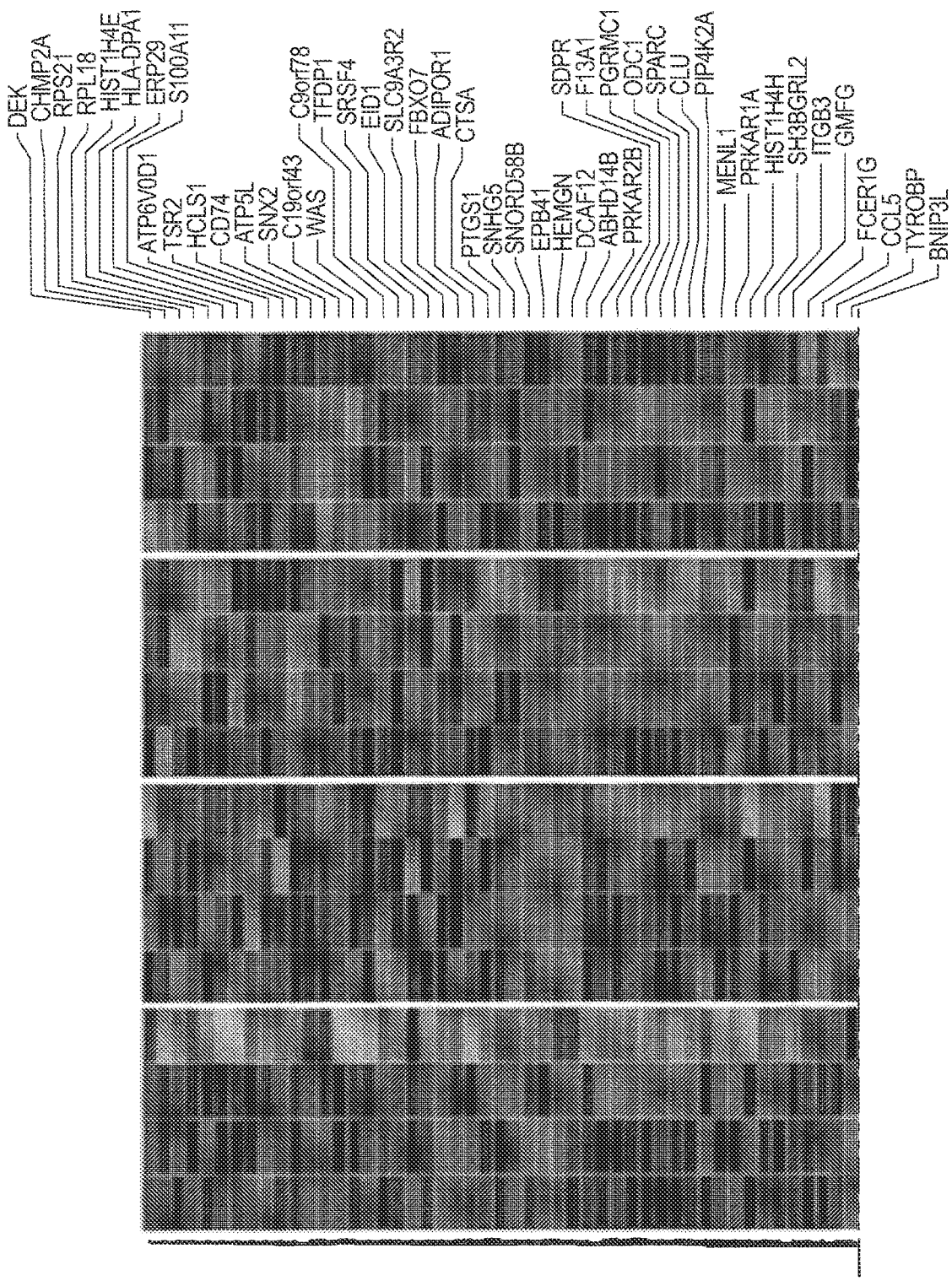
FIG. 3C-3D depicts heatmap of the top 100 cell free transcript levels exhibiting different temporal levels in pre-term and normal pregnancy using RNA-Seq.
Figure 3D:
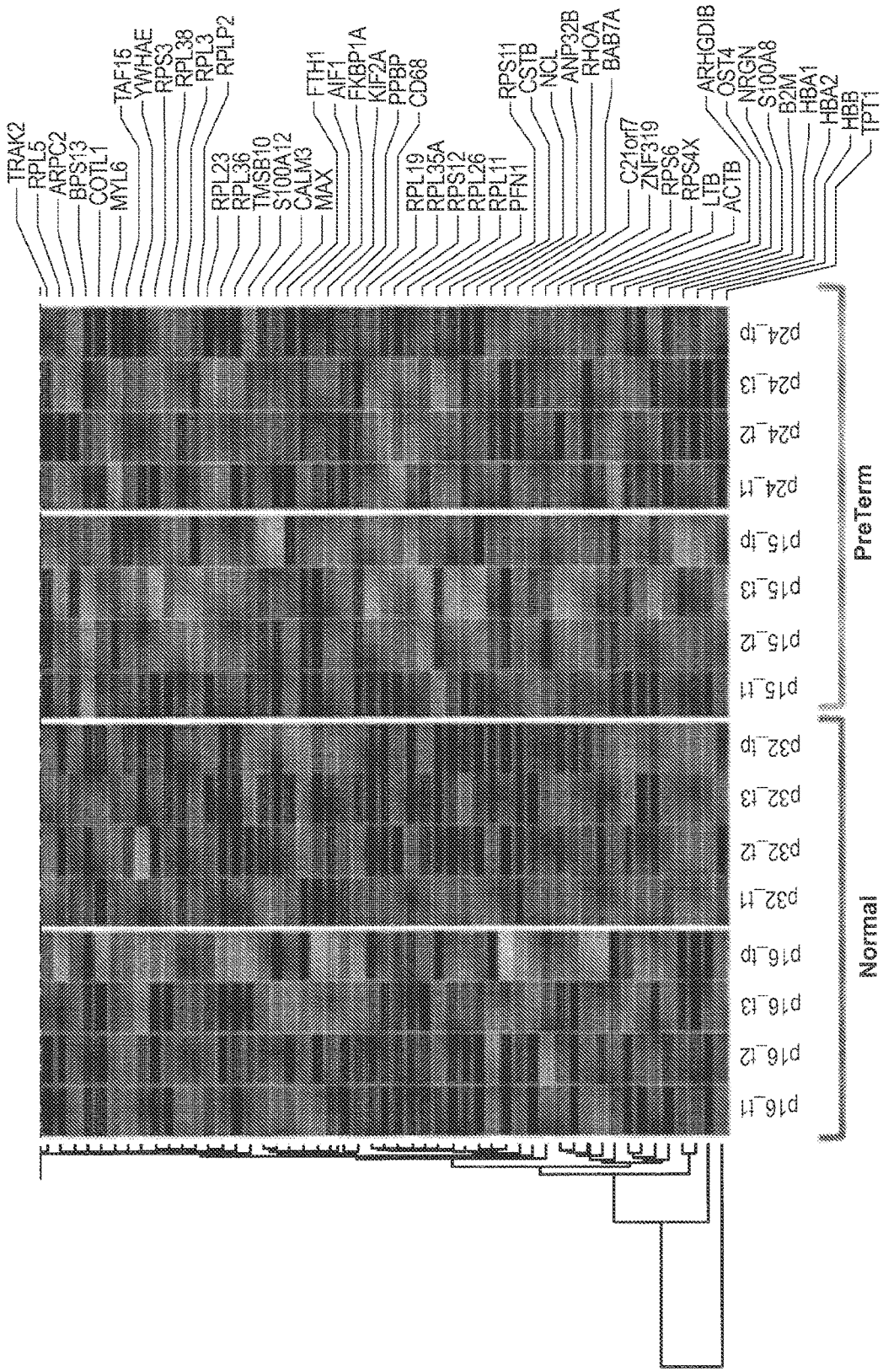

Identification of Cell Free RNA Transcripts in Maternal Plasma Exhibiting Significantly Different Time Varying Trends Between Pre-Term and Normal Pregnancy Across all Three Trimesters and Post-Partum A heatmap of the top 100 cell free transcript levels exhibiting different temporal levels in preterm and normal pregnancy using microarrays is shown in FIG. 3A. A heatmap of the top 100 cell free transcript levels exhibiting different temporal levels in preterm and normal pregnancy using RNA-Seq is shown in FIG. 3B.

Common Cell Free RNA Transcripts Identified by Microarray and RNA-Seq which Exhibit Significantly Different Time Varying Trends Between Pre-Term and Normal Pregnancy Across all Three Trimesters and Post Partum A ranking of the top 20 transcripts differentially expressed between pre-term and normal pregnancy is shown in FIG. 4. These top 20 common RNA transcripts were analyzed using Gene Ontology and were shown to be enriched for proteins that are attached (integrated or loosely bound) to the plasma membrane or on the membranes of the platelets (see FIG. 5).

Gene Expression Profiles for PVALB

Figures 5, 6:
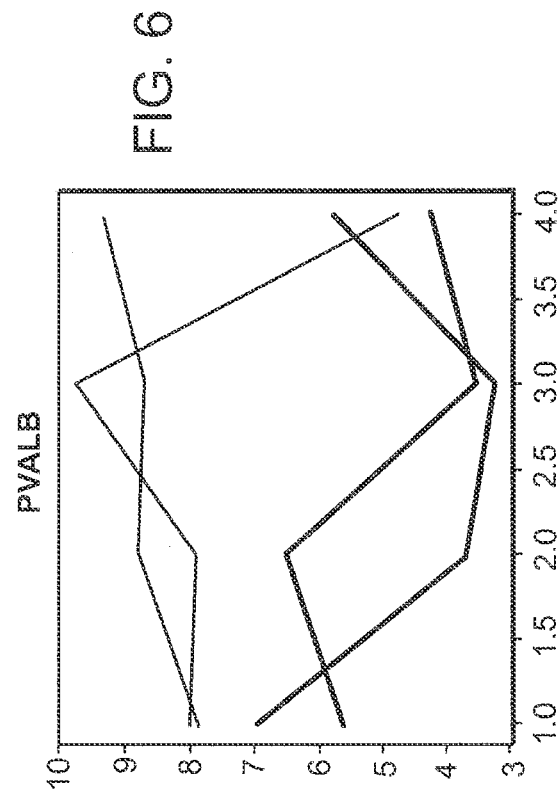
FIG. 5 depicts results of a Gene Ontology analysis on the top 20 common RNA transcripts of FIG. 4, showing those transcripts enriched for proteins that are attached (integrated or loosely bound) to the plasma membrane or on the membranes of the platelets.
FIG. 6 depicts that the gene expression profile for PVALB across the different trimesters shows the premature births [highlighted in blue] has higher levels of cell free RNA transcripts found as compared to normal pregnancy.

The protein encoded by PVALB gene is a high affinity calcium ion-binding protein that is structurally and functionally similar to calmodulin and troponin C. The encoded protein is thought to be involved in muscle relaxation. As shown in FIG. 6, the gene expression profile for PVALB across the different trimesters shows the premature births [highlighted in blue] has higher levels of cell free RNA transcripts found as compared to normal pregnancy.

Conclusion:

Results from quantification and characterization of maternal plasma cell-free RNA using RNA-Seq strongly suggest that pregnancy associated transcripts can be detected.

Furthermore, both RNA-Seq and microarray methods can detect considerable gene transcripts whose level showed differential time trends that has a high probability of being associated with premature births.

The methods described herein can be modified to investigate pregnancies of different pathological situations and can also be modified to investigate temporal changes at more frequent time points.

Example 2: Quantification of Tissue-Specific Cell-Free RNA Exhibiting Temporal Variation During Pregnancy Overview:

Cell-free fetal DNA found in maternal plasma has been exploited extensively for non-invasive diagnostics. In contrast, cell-free fetal RNA which has been shown to be similarly detected in maternal circulation has yet been applied widely as a form of diagnostics. Both fetal cell-free RNA and DNA face similar challenges in distinguishing the fetal from maternal component because in both cases the maternal component dominates. To detect cell-free RNA of fetal origin, focus can be placed on genes that are highly expressed only during fetal development, which are subsequently inferred to be of fetal in origin and easily distinguished from background maternal RNA. Such a perspective is collaborated by studies that has established that cell-free fetal RNA derived from genes that are highly expressed in the placenta are detectable in maternal plasma during pregnancy.

A significant characteristic that set RNA apart from DNA can be attributed to RNA transcripts dynamic nature which is well reflected during fetal development. Life begins as a series of well-orchestrated events that starts with fertilization to form a single-cell zygote and ends with a multicellular organism with diverse tissue types. During pregnancy, majority of fetal tissues undergoes extensive remodeling and contain functionally diverse cell types. This underlying diversity can be generated as a result of differential gene expression from the same nuclear repertoire; where the quantity of RNA transcripts dictate that different cell types make different amount of proteins, despite their genomes being identical. The human genome comprises approximately 30,000 genes. Only a small set of genes are being transcribed to RNA within a particular differentiated cell type. These tissue specific RNA transcripts have been identified through many studies and databases involving developing fetuses of classical animal models. Combining known literature available with high throughput data generated from samples via sequencing, the entire collection of RNA transcripts contained within maternal plasma can be characterized.

Fetal organ formation during pregnancy depends on successive programs of gene expression. Temporal regulation of RNA quantity is necessary to generate this progression of cell differentiation events that accompany fetal organ genesis. To unravel similar temporal dynamics for cell free RNA, the expression profile of maternal plasma cell free RNA, especially the selected fetal tissue specific panel of genes, as a function across all three trimesters during pregnancy and post-partum were analyzed. Leveraging high throughput qPCR and sequencing technologies capability for simultaneous quantification of cell free fetal tissue specific RNA transcripts, a system level view of the spectrum of RNA transcripts with fetal origins in maternal plasma was obtained. In addition, maternal plasma was analyzed to deconvolute the heterogeneous cell free transcriptome of fetal origin a relative proportion of the different fetal tissue types. This approach incorporated physical constraints regarding the fetal contributions in maternal plasma, specifically the fraction of contribution of each fetal tissues were required to be non-negative and sum to one during all three trimesters of the pregnancy. These constraints on the data set enabled the results to be interpreted as relative proportions from different fetal organs. That is, a panel of previously selected fetal tissue-specific RNA transcripts exhibiting temporal variation can be used as a foundation for applying quadratic programing in order to determine the relative tissue-specific RNA contribution in one or more samples.

When considered individually, quantification of each of these fetal tissue specific transcripts within the maternal plasma can be used as a measure for the apoptotic rate of that particular fetal tissue during pregnancy. Normal fetal organ development is tightly regulated by cell division and apoptotic cell death. Developing tissues compete to survive and proliferate, and organ size is the result of a balance between cell proliferation and death. Due to the close association between aberrant cell death and developmental diseases, therapeutic modulation of apoptosis has become an area of intense research, but with this comes the demand for monitoring the apoptosis rate of specific. Quantification of fetal cell-free RNA transcripts provide such prognostic value, especially in premature births where the incidence of apoptosis in various organs of these preterm infants has been have been shown to contribute to neurodevelopmental deficits and cerebral palsy of preterm infants.

Sample Collection and Study Design
Selection of Fetal Tissue Specific Transcript Panel To detect the presence of these fetal tissue-specific transcripts, a list of known fetal tissue specific genes was prepared from known literature and databases. The specificity for fetal tissues was validated by cross referencing between two main databases: TISGeD (Xiao, S.-J., Zhang, C. & Ji, Z.-L. TiSGeD: a Database for Tissue-Specific Genes. *Bioinformatics (Oxford, England)* 26, 1273-1275 (2010)) and BioGPS (Wu, C. et al. BioGPS: an extensible and customizable portal for querying and organizing gene annotation resources. *Genome biology* 10, R130 (2009); Su, A. I. et al. A gene atlas of the mouse and human protein-encoding transcriptomes. *Proceedings of the National Academy of Sciences of the United States of America* 101, 6062-7 (2004)). Most of these selected transcripts are associated with known fetal developmental processes. This list of genes was overlapped with RNA sequencing and microarray data to generate the panel of selected fetal tissue-specific transcripts shown in FIG. 8.

Subjects

Samples of maternal blood were collected from normal pregnant women during the first trimester, second trimester, third trimester, and post-partum. For positive controls, fetal tissue specific RNA from the various fetal tissue types were bought from Agilent. Negative controls for the experiments were performed with the entire process with water, as well as with samples that did not undergoes the reverse transcription process.

Blood Collection and Processing

At each time-point, 7 to 15 mL of peripheral blood was drawn from each subject. Blood was centrifuged at 1600 g for 10 mins and transferred to microcentrifuge tubes for further centrifugation at 16000 g for 10 mins to remove residual cells. The above steps were carried out within 24 hours of the blood draw. Resulting plasma is stored at−80 Celsius for subsequent RNA extractions.

RNA Extraction

Cell free RNA extractions were carried using Trizol followed by Qiagen's RNeasy Mini Kit. To ensure that there are no contaminating DNA, DNase digestion is performed after RNA elution using RNase free DNase from Qiagen. Resulting cell free RNA from the pregnant subjects was then processed using standard microarrays and Illumina RNA-seq protocols. These steps generate the sequencing library that we used to generate RNA-seq data as well as the microarray expression data. The remaining cell free RNA are then used for parallel qPCR.

Parallel qPCR of Selected Transcripts

Accurate quantification of these fetal tissue specific transcripts was carried out using the Fluidigm BioMark system (See e.g. Spurgeon, S. L., Jones, R. C. & Ramakrishnan, R. High throughput gene expression measurement with real time PCR in a microfluidic dynamic array. *PloS one* 3, e1662 (2008)). This system allows for simultaneous query of a panel of fetal tissue specific transcripts. Two parallel forms of inquiry were conducted using different starting source of material. One was using the cDNA library from the Illumina sequencing protocol and the other uses the eluted RNA directly. Both sources of material were amplified with evagreen primers targeting the genes of interest. Both sources, RNA and cDNA, were preamplified. cDNA is preamplifed using evagreen PCR supermix and primers. RNA source is preamplified using the CellsDirect One-Step qRT-PCR kit from Invitrogen. Modifications were made to the default One-Step qRT-PCR protocol to accommodate a longer incubation time for reverse transcription. 19 cycles of preamplification were conducted for both sources and the collected PCR products were cleaned up using Exonuclease I Treatment. To increase the dynamic range and the ability to quantify the efficiency of the later qPCR steps, serial dilutions were performed on the PCR products from 5 fold, 10 fold and 10 fold dilutions. Each of the collected maternal plasma from individual pregnant women across the time points went through the same procedures and was loaded onto 48×48 Dynamic Array Chips from Fluidigm to perform the qPCR. For positive control, fetal tissue specific RNA from the various fetal tissue types were bought from Agilent. Each of these RNA from fetal tissues went through the same preamplification and clean-up steps. A pool sample with equal proportions of different fetal tissues was created as well for later analysis to deconvolute the relative contribution of each tissue type in the pooled samples. All collected data from the Fluidigm BioMark system were pre-processed using Fluidigm Real Time PCR Analysis software to obtain the respective Ct values for each of the transcript across all samples. Negative controls of the experiments were performed with the entire process with water, as well as with samples that did not undergoes the reverse transcription process.

Figure 9A:
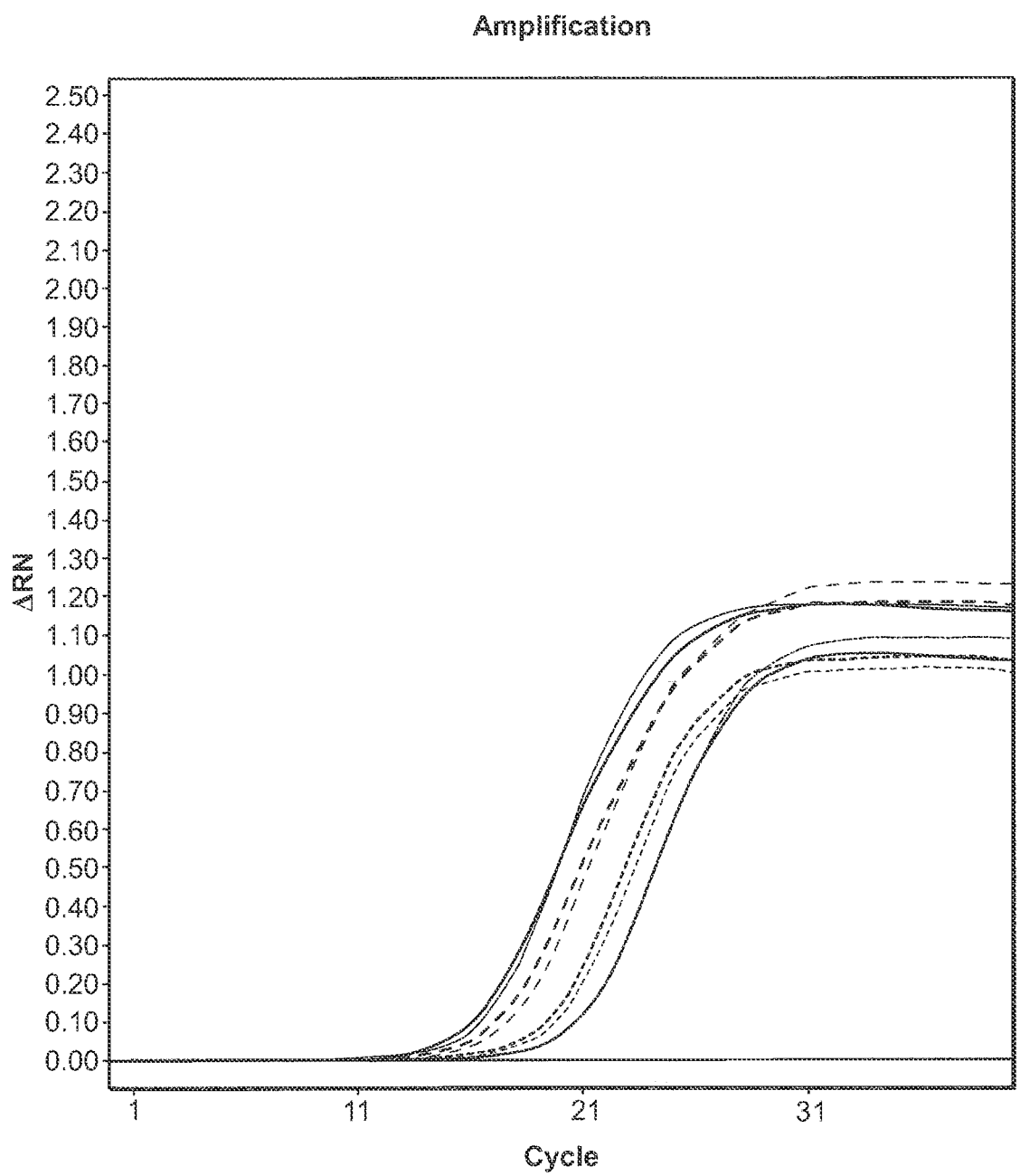
FIG. 9A-9B depict the raw data of parallel quantification of the fetal tissue-specific transcripts showing changes across maternal time-points (first trimester, second trimester, third trimester, and post partum) using the actual cell free RNA as well as the cDNA library of the same cell free RNA.
Figure 9B:
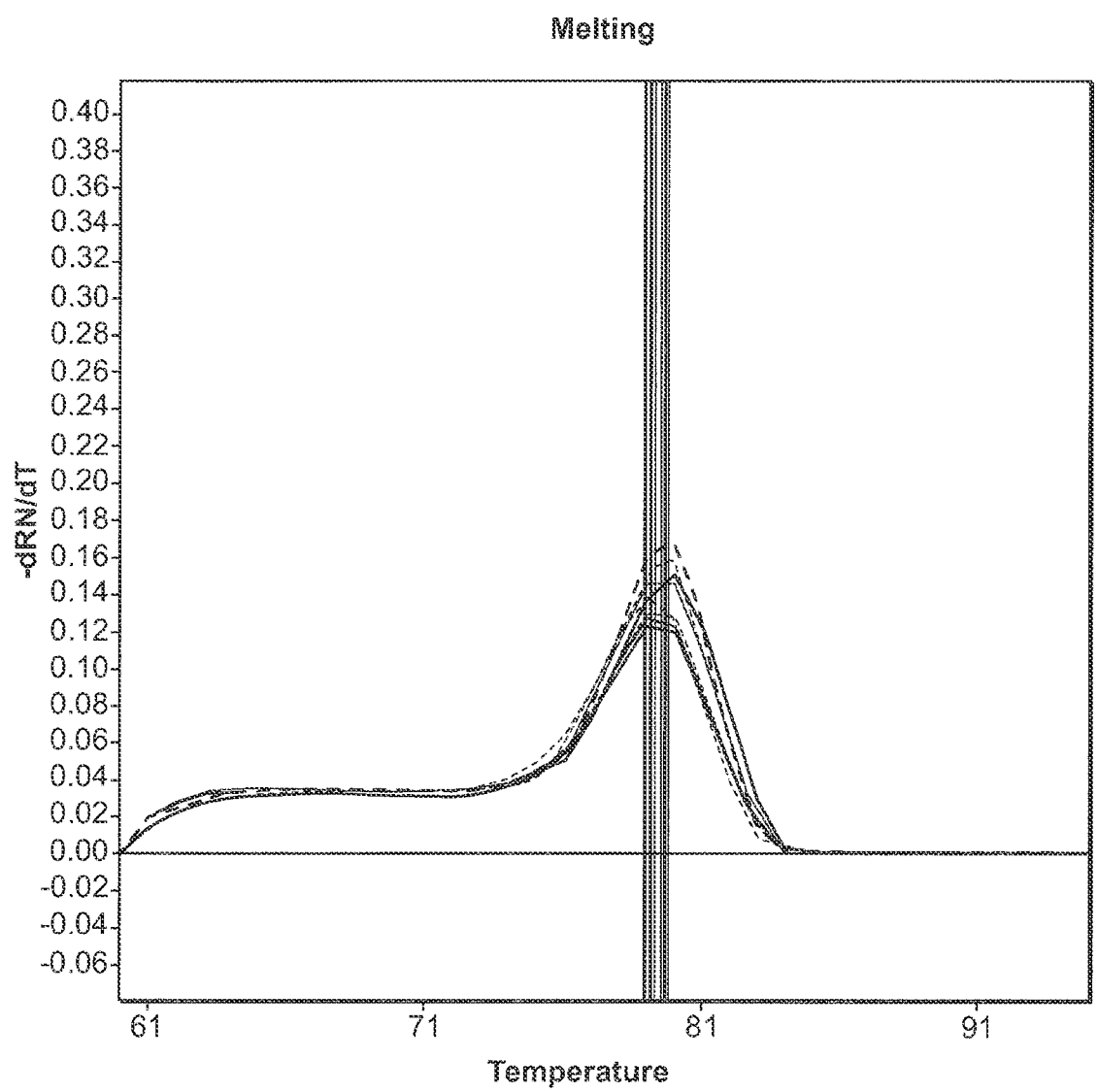

Data Analysis:

Fetal tissue specific RNA transcripts clear from the maternal peripheral bloodstream within a short period after birth. That is, the post-partum cell-free RNA transcriptome of maternal blood lacks fetal tissue specific RNA transcripts. As a result, it is expected that the quantity of these fetal tissue-specific transcripts to be higher before than after birth. The data of interest were the relative quantitative changes of the tissue specific transcripts across all three trimesters of pregnancy as compared to this baseline level after the baby is born. As described the methods, the fetal tissue-specific transcripts were quantified in parallel both using the actual cell-free RNA as well as the cDNA library of the same cell-free RNA. An example of the raw data obtained is shown in FIGS. 9A and 9B. The qPCR system gave a better quality readout using the cell-free RNA as the initial source. Focusing on the qPCR results from the direct cell-free RNA source, the analysis was conducted by comparing the fold changes level of each of these fetal tissue specific transcripts across all three trimesters using the post-partum level as the baseline for comparison. The Delta-Delta Ct method was employed (Schmittgen, T. D. & Livak, K. J. Analyzing real-time PCR data by the comparative CT method. *Nature Protocols* 3, 1101-1108 (2008)). Each of the transcript expression level was compared to the housekeeping genes to get the delta Ct value. Subsequently, to compare each trimesters to after birth, the delta-delta Ct method was applied using the post-partum data as the baseline.

Figure 10B:
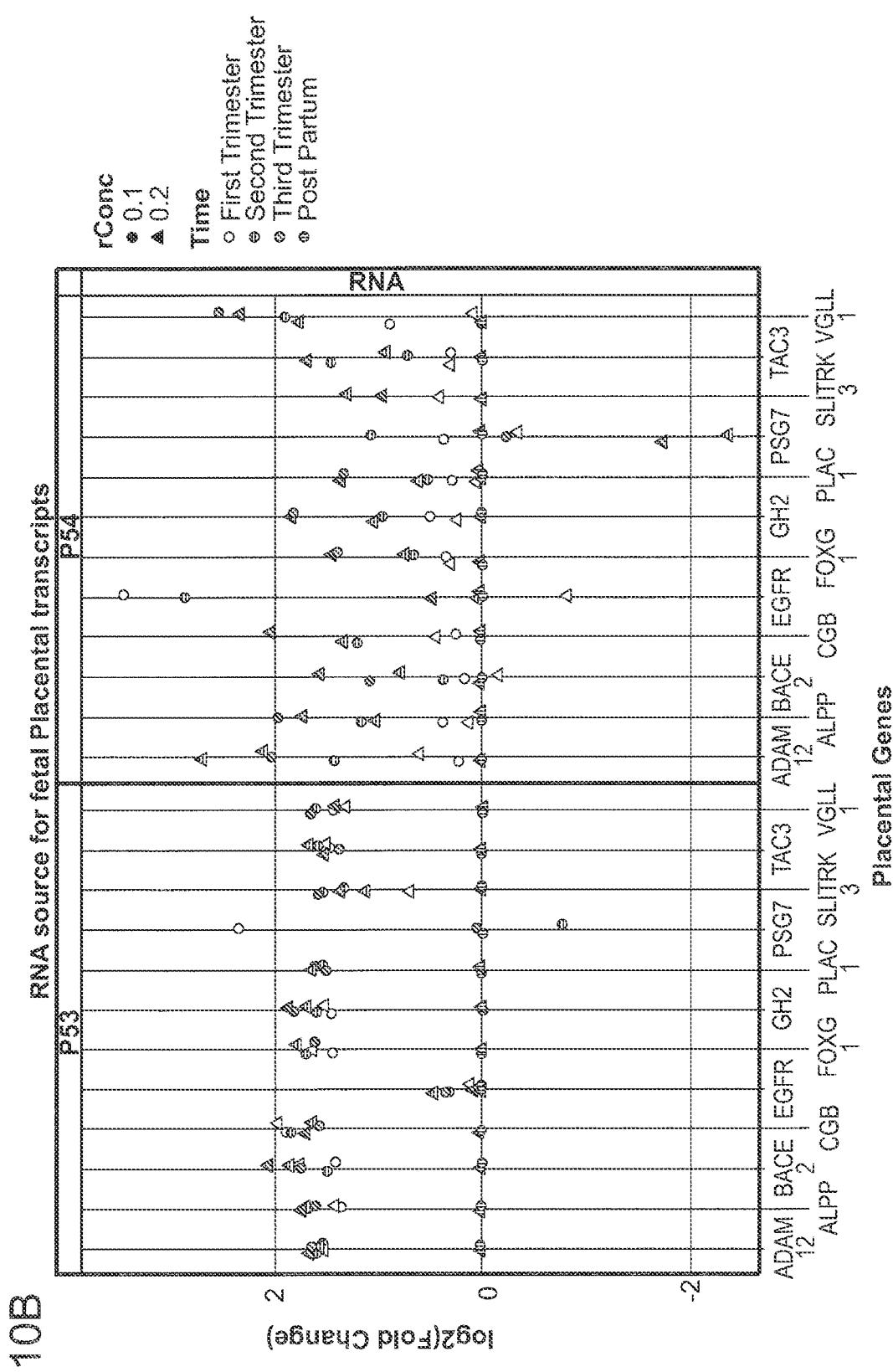
Figure 11A:
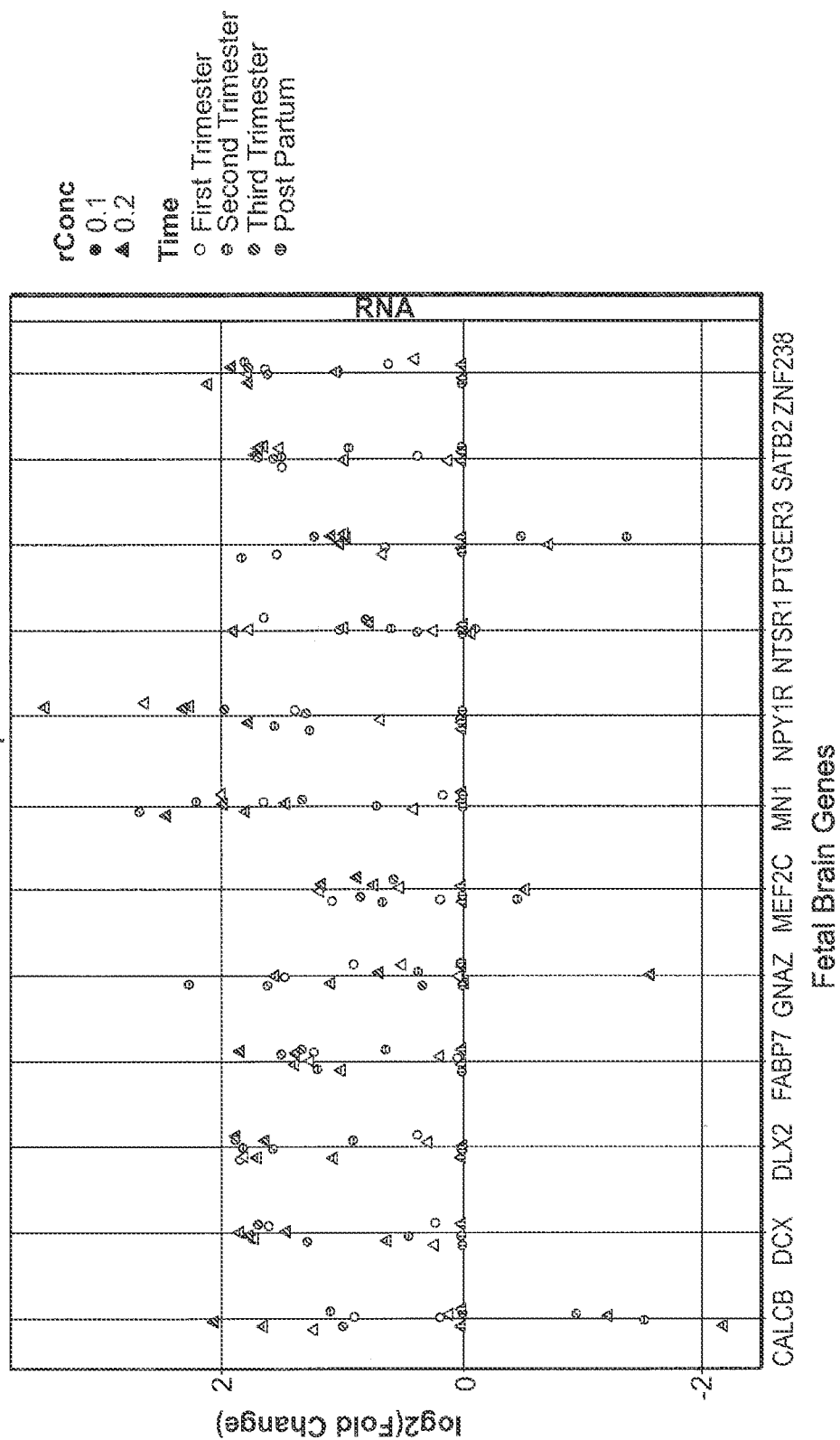
FIG. 11A-11B illustrates relative expression of fetal brain genes across maternal time points (first trimester, second trimester, third trimester, and post partum).
Figure 11B:
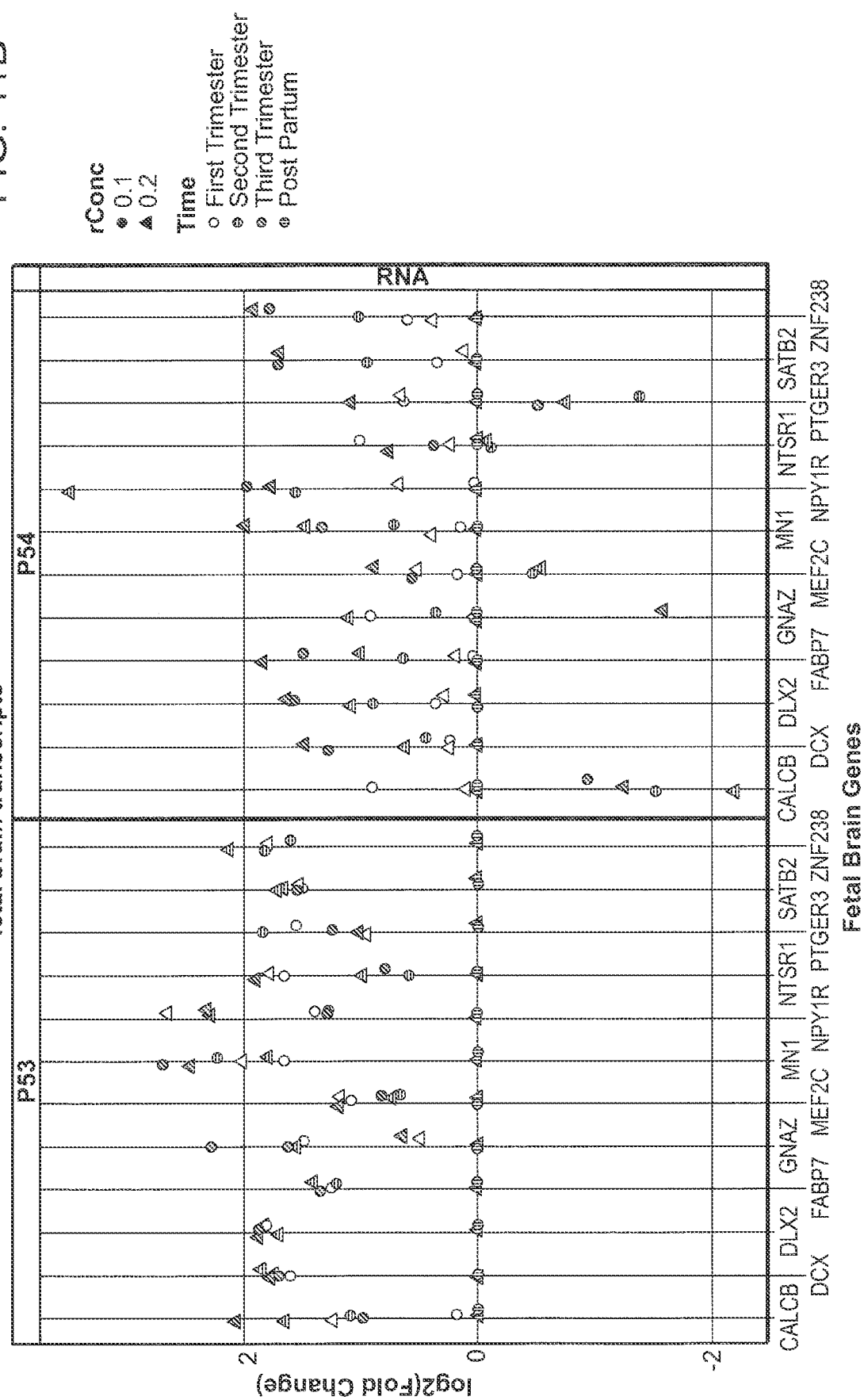
Figure 12A:
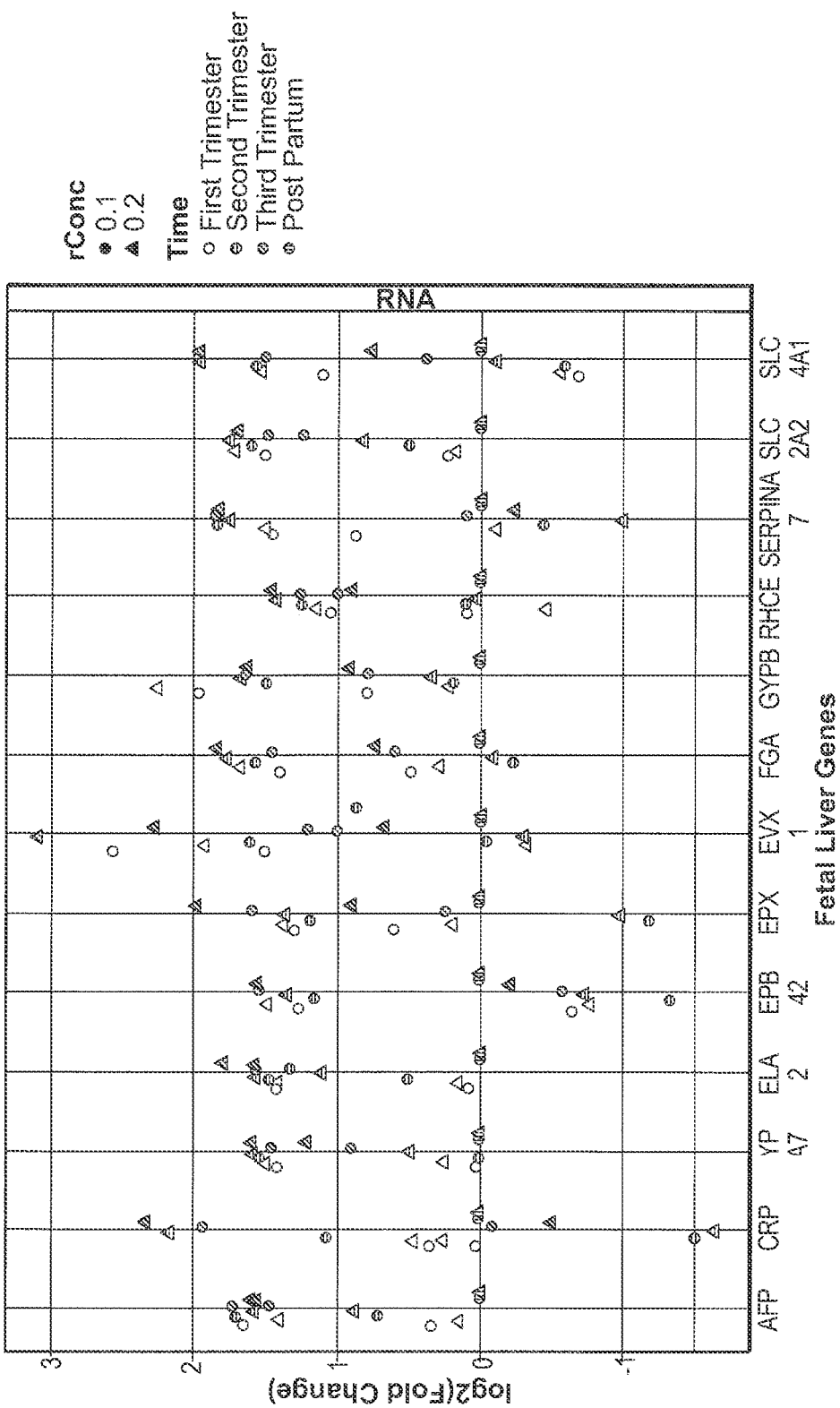
FIG. 12A-12B illustrates relative expression of fetal liver genes across maternal time points (first trimester, second trimester, third trimester, and post partum).
Figure 12B:
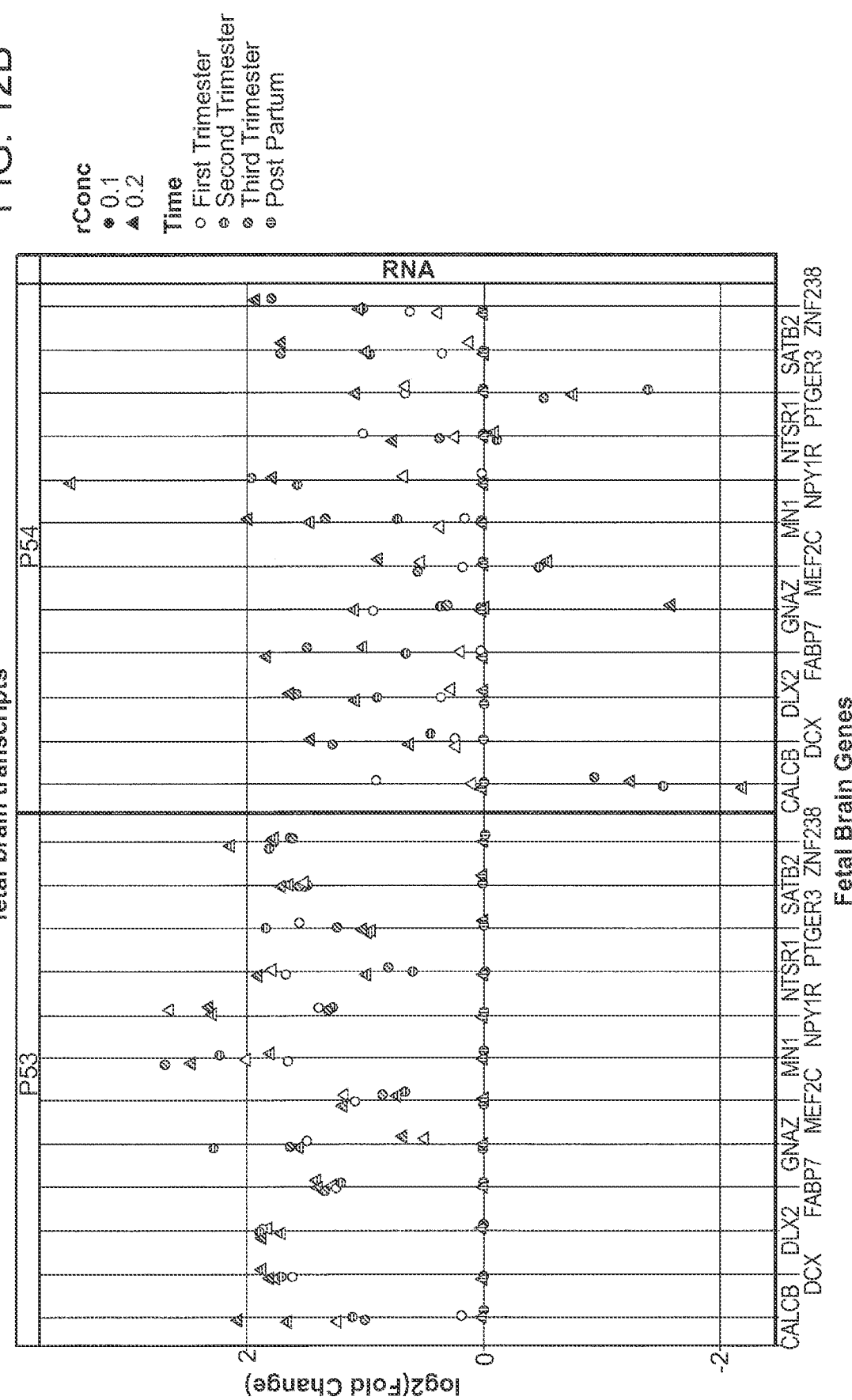

Results and Discussion:

As shown in FIGS. 10, 11, and 12, the tissue-specific transcripts are generally found to be at a higher level during the trimesters as compared to after-birth. In particular, the tissue-specific panel of placental, fetal brain and fetal liver specific transcripts showed the same bias, where these transcripts are typically found to exist at higher levels during pregnancy then compared to after birth. Between the different trimesters, a general trend showed that the quantity of these transcripts increase with the progression into pregnancy.

Biological Significance of Quantified Fetal Tissue-Specific RNA: Most of the transcripts in the panel were involved in fetal organ development and many are also found within the amniotic fluid. Once such example is ZNF238. This transcript is specific to fetal brain tissue and is known to be vital for cerebral cortex expansion during embryogenesis when neuronal layers are formed. Loss of ZNF238 in the central nervous system leads to severe disruption of neurogenesis, resulting in a striking postnatal small-brain phenotype. Using methods of the invention, one can determine whether ZNF238 is presenting in healthy, normal levels according to the stage of development.

Known defects due to the loss of ZNF238 include a striking postnatal small-brain phenotype: microcephaly, agenesis of the corpus callosum and cerebellar hypoplasia. Microcephaly can sometimes be diagnosed before birth by prenatal ultrasound. In many cases, however, it might not be evident by ultrasound until the third trimester. Typically, diagnosis is not made until birth or later in infancy upon finding that the baby's head circumference is much smaller than normal. Microcephaly is a life-long condition and currently untreatable. A child born with microcephaly will require frequent examinations and diagnostic testing by a doctor to monitor the development of the head as he or she grows. Early detection of ZNf238 differential expression using methods of the invention provides for prenatal diagnosis and may hold prognostic value for drug treatments and dosing during course of treatment.

Beyond ZNF238, many of the characterized transcripts may hold diagnostic value in developmental diseases involving apoptosis, i.e., diseases caused by removal of unnecessary neurons during neural development. Seeing that apoptosis of neurons is essential during development, one could extrapolate that similar apoptosis might be activated in neurodegenerative diseases such as Alzheimer's disease, Huntington's disease, and amyotrophic lateral sclerosis. In such a scenario, the methodology described herein will allow for close monitoring for disease progression and possibly an ideal dosage according to the progression.

Deducing relative contributions of different fetal tissue types: Differential rate of apoptosis of specific tissues may directly correlate with certain developmental diseases. That is, certain developmental diseases may increase the levels of a particular specific RNA transcripts being observed in the maternal transcriptome. Knowledge of the relative contribution from various tissue types will allow for observations of these types of changes during the progression of these diseases. The quantified panel of fetal tissue specific transcripts during pregnancy can be considered as a summation of the contributions from the various fetal tissues.

Expressing, $$Y_i = \sum_j \pi_i x_{ij} + \varepsilon$$

where Y is the observed transcript quantity in maternal plasma for gene i, X is the known transcript quantity for gene i in known fetal tissue j and E the normally distributed error. Additional physical constraints includes:

1. Summation of all fraction contributing to the observed quantification is 1, given by the condition: $\Sigma \pi_i = 1$
2. All the contribution from each tissue type has to greater than or equal zero. There is no physical meaning to having a negative contribution. This is given by $\pi_i \geq 0$, since $\pi$ is defined as the fractional contribution of each tissue types.

Consequently to obtain the optimal fractional contribution of each tissue type, the least-square error is minimized. The above equations are then solved using quadratic programming in R to obtain the optimal relative contributions of the tissue types towards the maternal cell free RNA transcripts. In the workflow, the quantity of RNA transcripts are given relative to the housekeeping genes in terms of Ct values obtained from qPCR. Therefore, the Ct value can be considered as a proxy of the measured transcript quantity. An increase in Ct value of one is similar to a two-fold change in transcript quantity, i.e. 2 raised to the power of 1. The process beings with normalizing all of the data in CT relative to the housekeeping gene, and is followed by quadratic programming.

As a proof of concept for the above scheme, different fetal tissue types (Brain, Placenta, Liver, Thymus, Lung) were mixed in equal proportions to generate a pool sample. Each fetal tissue types (Brain, Placenta, Liver, Thymus, Lung) along with the pooled sample were quantified using the same Fluidigm Biomark System to obtain the Ct values from qPCR for each fetal tissue specific transcript across all tissues and the pooled sample. These values were used to perform the same deconvolution. The resulting fetal fraction of each of the fetal tissue organs (Brain, Placenta, Liver, Thymus, Lung) was 0.109, 0.206, 0.236, 0.202 & 0.245 respectively.

Conclusion:

In summary, the panel of fetal specific cell free transcripts provides valuable biological information across different fetal tissues at once. Most particularly, the method can deduce the different relative proportions of fetal tissue-specific transcripts to total RNA, and, when considered individually, each transcript can be indicative of the apoptotic rate of the fetal tissue. Such measurements have numerous potential applications for developmental and fetal medicine. Most human fetal development studies have relied mainly on postnatal tissue specimens or aborted fetuses. Methods described herein provide quick and rapid assay of the rate of fetal tissue/organ growth or death on live fetuses with minimal risk to the pregnant mother and fetus. Similar methods may be employed to monitor major adult organ tissue systems that exhibit specific cell free RNA transcripts in the plasma.

Example 3: Deconvolution of Adult Cell-Free Transcriptome

Overview:

The plasma RNA profiles of 4 healthy, normal adults were analyzed. Based on the gene expression profile of different tissue types, the methods described quantify the relative contributions of each tissue type towards the cell-free RNA component in a donor's plasma. For quantification, apoptotic cells from different tissue types are assumed to release their RNA into the plasma. Each of these tissues expressed a specific number of genes unique to the tissue type, and the observed cell-free RNA transcriptome is a summation of these different tissue types.

Study Design and Methods:

To determine the contribution of tissue-specific transcripts to the cell-free adult transcriptome, a list of known tissue-specific genes was prepared from known literature and databases. Two database sources were utilized: Human U133A/GNF1H Gene Atlas and RNA-Seq Atlas. Using the raw data from these two database, tissue-specific genes were identified by the following method. A template-matching process was applied to data obtained from the two databases for the purpose of identifying tissue-specific gene. The list of tissue specific genes identified by the method is given in FIG. 18. The specificity and sensitivity of the panel is constrained by the number of tissue samples in the database. For example, the Human U133A/GNF1H Gene Atlas dataset includes 84 different tissue samples, and a panel's specificity from that database is constrained by the 84 sample sets. Similarly, for the RNA-seq atlas, there are 11 different tissue samples and specificity is limited to distinguishing between these 11 tissues. After obtaining a list of tissue-specific transcripts from the two databases, the specificity of these transcripts was verified with literature as well as the TisGED database.

The adult cell-free transcriptome can be considered as a summation of the tissue-specific transcripts obtained from the two databases. To quantitatively deduce the relative proportions of the different tissues in an adult cell-free transcriptome, quadratic programming is performed as a constrained optimization method to deduce the relative optimal contributions of different organs/tissues towards the cell free-transcriptome. The specificity and accuracy of this process is dependent on the table of genes provided in Figure X and the extent by which that they are detectable in RNA-seq and microarray.

Subjects: Plasma samples were collected from 4 healthy, normal adults.

Initial Results:

Deconvolution of our adult cell-free RNA transcriptome from microarray using the above methods revealed the relative contributions of the different tissue and organs are tabulated in FIG. 13.

FIG. 13 shows that the normal cell free transcriptome for adults is consistent across all 4 subjects. The relative contributions between the 4 subjects do not differ greatly, suggesting that the relative contributions from different tissue types are relatively stable between normal adults. Out of the 84 tissue types available, the deduced optimal major contributing tissues are from whole blood and bone marrow.

An interesting tissue type contributing to circulating RNA is the hypothalamus. The hypothalamus is bounded by specialized brain regions that lack an effective blood-brain barrier; the capillary endothelium at these sites is fenestrated to allow free passage of even large proteins and other molecules which in our case we believed that RNA transcripts from apoptotic cells in that region could be released into the plasma cell free RNA component.

The same methods were performed on the subjects using RNA-seq. The results described herein are limited due to the amount of tissue-specific RNA-Seq data available. However, it is understood that tissue-specific data is expanding with the increasing rate of sequencing of various tissue rates, and future analysis will be able to leverage those datasets. For RNA-seq data (as compared to microarray), whole blood nor the bone marrow samples are not available. The cell free transcriptome can only be decomposed to the available 11 different tissue types of RNA-seq data. Of which, only relative contributions from the hypothalamus and spleen were observed, as shown in FIG. 14.

Figure 16:
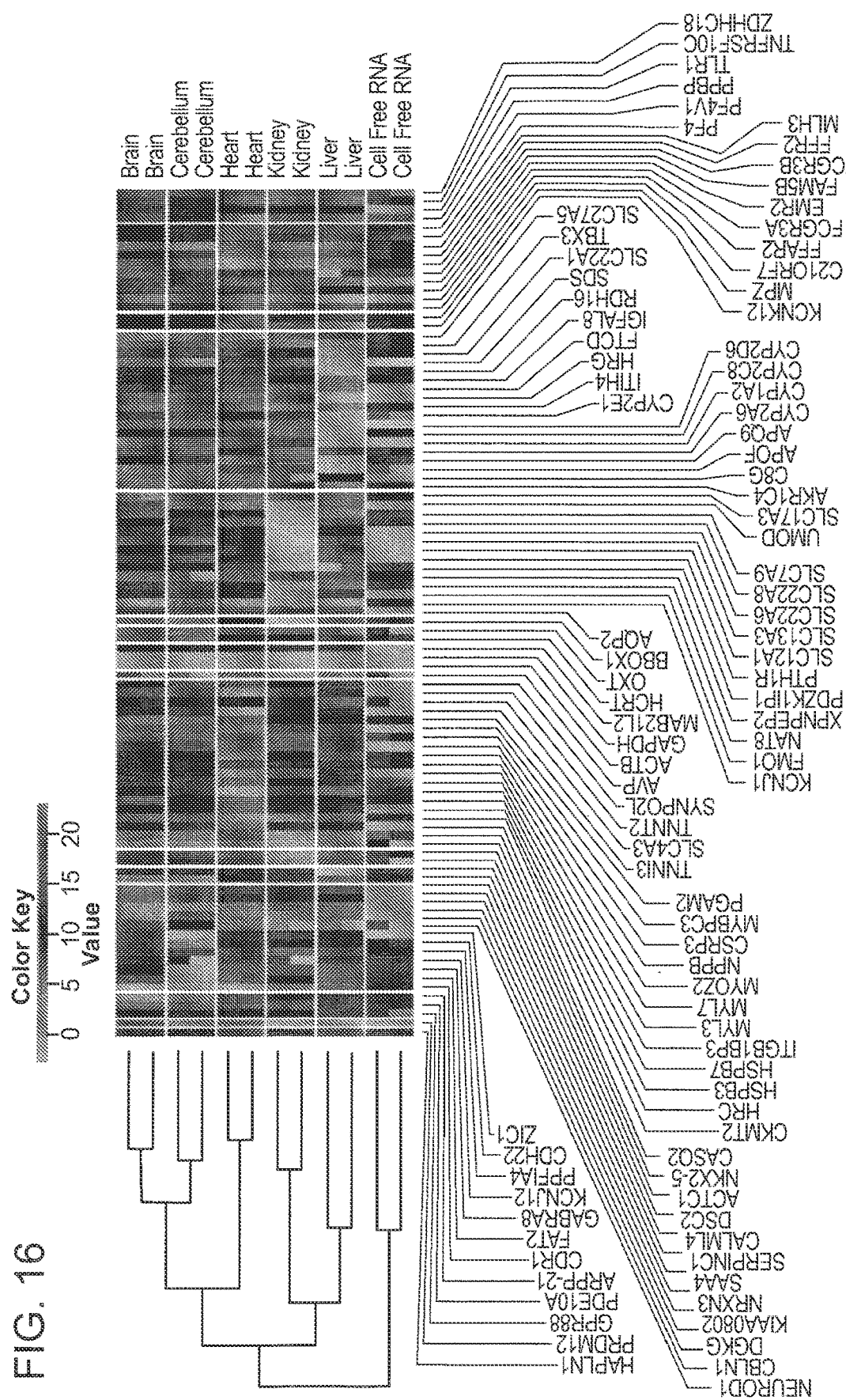
FIG. 16 shows a heat map of the tissue specific transcripts of FIG. 15, being detectable in the cell free RNA.

A list of 94 tissue-specific genes (as shown in FIG. 15) was further selected for verification with qPCR. The Fluidigm BioMark Platform was used to perform the qPCR on RNA derived from the following tissues: Brain, Cerebellum, Heart, Kidney, Liver and Skin. Similar qPCR workflow was applied to the cell free RNA component as well. The delta Ct values by comparing with the housekeeping genes: ACTB was plotted in the heatmap format in FIG. 16, which shows that these tissue specific transcripts are detectable in the cell free RNA.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method comprising:
   (a) obtaining a blood plasma sample from a subject, wherein the obtaining comprises adding a cell-membrane stabilizing agent to a blood sample and depleting cells from the blood sample;
   (b) preparing complementary deoxyribonucleic acid (cDNA) from cell-free messenger ribonucleic acid (mRNA) in the blood plasma sample to produce prepared cDNA;
   (c) amplifying the prepared cDNA to produce double-stranded cDNA;
   (d) sequencing the double-stranded cDNA to produce sequence information;
   (e) determining, using the sequence information, levels of cell-free mRNA associated with a gene selected from the group consisting of: ABHD8, CHST10, CLCN6, FBXL15, GPR17, KIF5A, KLHL26, NELL1, PIAS4, PPP2R2D, RAB33A, RAC3, RAPGEFL1, THAP10, and TIMM22; and
   (f) determining a contribution of the levels of cell-free mRNA associated with the gene to the blood plasma sample relative to an expression level of a reference gene expressed in blood plasma.

2. The method of claim 1, wherein the levels of cell-free mRNA associated with the gene are derived at least in part from whole brain tissue.

3. The method of claim 1, wherein (c) comprises amplifying the prepared cDNA indiscriminately.

4. The method of claim 1, further comprising (g) characterizing the gene as abnormal if a difference is detected between the levels of cell-free mRNA associated with the gene and the expression level of the reference gene expressed in blood plasma.

5. The method of claim 1, wherein (a) comprises a first centrifugation at greater than or equal to 1600×g to separate cells from the blood sample to produce a first supernatant.

6. The method of claim 5, wherein (a) comprises a second centrifugation at greater than or equal to 16,000×g to separate residual cells from the first supernatant to produce a second supernatant.

7. The method of claim 1, wherein (b) is performed without diluting the cell-free mRNA.

8. The method of claim 1, wherein (b) is performed without separating the blood plasma sample into separate reaction vessels.

9. The method of claim 1, wherein the cell-free mRNA comprises unbound cell-free mRNA.

* * * * *